US008680244B2

(12) United States Patent
Doms et al.

(10) Patent No.: US 8,680,244 B2
(45) Date of Patent: Mar. 25, 2014

(54) METHOD FOR THE PRODUCTION OF ANTIBODIES THAT BIND TO MULTIPLE MEMBRANE SPANNING PROTEINS

(75) Inventors: Robert Doms, Berwyn, PA (US); Joseph Rucker, Philadelphia, PA (US); Trevor L Hoffman, Irvine, CA (US); Paul Bates, Swarthmore, PA (US); James A Hoxie, Berwyn, PA (US); Michael J Endres, Painesville, OH (US); John Balliet, Norristown, PA (US); Dennis L Kolson, Secane, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/421,559

(22) Filed: Mar. 15, 2012

(65) Prior Publication Data

US 2012/0195882 A1    Aug. 2, 2012

Related U.S. Application Data

(60) Division of application No. 12/720,398, filed on Mar. 9, 2010, now Pat. No. 8,158,130, which is a continuation of application No. 10/032,311, filed on Dec. 21, 2001, now Pat. No. 7,763,258, which is a continuation-in-part of application No. 09/006,678, filed on Jan. 13, 1998, now abandoned.

(60) Provisional application No. 60/257,988, filed on Dec. 22, 2000, provisional application No. 60/047,226, filed on May 20, 1997.

(51) Int. Cl.
*C07K 16/00* (2006.01)

(52) U.S. Cl.
USPC ..................................................... 530/388.22

(58) Field of Classification Search
None
See application file for complete search history.

(56) References Cited

U.S. PATENT DOCUMENTS

| 6,261,558 | B1 * | 7/2001 | Barbas et al. ...................... 506/1 |
| 7,790,446 | B2 | 9/2010 | Silla et al. |
| 2002/0183247 | A1 | 12/2002 | Doms |
| 2004/0014033 | A1 | 1/2004 | Hunt |
| 2011/0076760 | A1 | 3/2011 | Silla et al. |

FOREIGN PATENT DOCUMENTS

| EP | 1851319 | 11/2007 |
| WO | 96/16087 | 5/1996 |
| WO | 01/02551 | 1/2001 |

OTHER PUBLICATIONS

Goodman, S. R., ed., 2008, Cell Membranes, in Medical Cell Biology, Third Edition, Elsevier Press, China, pp. 36-38.*
Rosenbaum, D. M., et al., May 2009, The structure and function of G-protein-coupled receptors, Nature 459:356-363.*
Suomalainen, M., and H. Garoff, Aug. 1994, Incorporation of homologous and heterologous proteins into the envelope of Moloney murine leukemia virus (M-MuLV), J. Virol. 68(8):4879-4889.*
Schnell, M. J., et al., Oct. 1996, Foreign glycoproteins expressed from recombinant vesicular stomatitis viruses are incorporated efficiently into virus particles, Proc. Natl. Acad. Sci. USA 93:11359-11365.*
Hoxie et al., "Nonrandom Association of Cellular Antigens with HTLV-III Virions, Human Immunology", vol. 18, pp. 39-52(1987).
Ott, "Cellular Proteins in HIV Virions", Medical Virology, vol. 7, pp. 167-180 (1997).
Young et al., "Efficient Incorporation of Human CD4 Protein into Avian Leukosis Virus Particles", Science, vol. 250, pp. 1421-1423(1990).
Schnell et al., "Foreign Glycoproteins Expressed from Recombinant Vesicular Stomatitis Viruses are Incorporated Efficiently into Virus Particles", P.N. AS, vol. 93, pp. 11359-11365 (1996).
Sanguinetti, M.C. et al., "A mechanistic link between an inherited and an acquired cardiac arrhythmia: HERG encodes the IKr potassium channel", Cell, 1995, 81(2):299-307.
Meyer, A. et al., "Cloning and characterization of a novel murine macrophage inflammatory protein-1 alpha receptor", J. Biol. Chem., 1996, 271(24):14445-14451.
Wang, H. et al., Modulation of ecotropic murine retroviruses by N-linked glycosylation of the cell surface receptor/amino acid transporter, J. Virol., 1996, 70(10):6884-6891.
Ohtsuka, N. et al., "Difference in virus-binding activity of two distinct receptor proteins for mouse hepatitis virus", J. Gen. Vir., 1996, 77:1683-1692.
Narayan, P., et al., Expression of functional lutropin/choriogonadotropin receptor in the baculovirus system, Molecular and Cellular Endocrinology, 1996;117:95-100.
Margljlies, B. J., Identification of the Human Cytomegalovirus G Protein-Coupled Receptor Homologue Encoded by UL33 in infected Cells and Enveloped Virus Particles, Virology; 1996, 225:111-125.
Office Action Mailed Aug. 6, 2008 for U.S. Appl. No. 10/901,399, entitled "Lipoparticles comprising proteins, methods of making, and using the same."
Mills et al. HIV p24-specific helper T cell clones from immunized primates recognize highly conserved regions of HIV-1. Journal of Immunology, vol. 144,1677-1683 (1990).
Office Action Mailed Mar. 28, 2007 for U.S. Appl. No. 10/901,399, entitled "Lipoparticles comprising proteins, methods of making, and using the same."

(Continued)

*Primary Examiner* — Jeffrey S. Parkin
(74) *Attorney, Agent, or Firm* — Pepper Hamilton LLP

(57) ABSTRACT

Enveloped virus vectors are described which comprise a cellular virus receptor protein and which are capable of fusing with a cell which comprises a viral envelope protein to which the cellular virus receptor protein is cognate. Enveloped virus vectors comprising a plurality of cellular virus receptor proteins are also described. Methods for making the enveloped virus vectors are described, as are methods of using the enveloped virus vectors. The invention further relates to a lipoparticle comprising a membrane spanning protein, and the lipoparticle can be attached to a sensor surface. The invention relates to methods of producing and using the lipoparticle to, inter alia, assess protein binding interactions.

13 Claims, 12 Drawing Sheets

(56) References Cited

OTHER PUBLICATIONS

Hoffman TL. et al "A biosensor assay for studying ligand-membrane receptor interactions: Binding of antibodies and HIV-1 Env to chemokine receptors" PNAS 2000, 97; 11215-11220.
Seifert R. et al. "GPCR-G alpha fusion proteins: molecular analysis of receptor-G-protein coupling". Trends Pharmacol Sci. Sep. 1999; 20(9):383-9).
Milligan G et al. "Chimaeric G alpha proteins: their potential use in drug discovery". Trends Pharmacol Sci. Mar. 1999; 20(3):118-124.
Martinez X. et al. "CD4-Independent protective cytotoxic T cells induced in early life by a non-replicative delivery system based on virus-like particles" Virology 305,428-435 (2003).
McEwen DP et al. "Fluorescent BODIPY-GTP analogs: real-time measurement of nucleotide binding to G proteins". Anal Biochem. Apr. 1, 2001;291(1):109-17.
Aiken et al., "Nef induces CD4 endocytosis: requirement for a critical dileucine motif in the membrane-proximal CD4 cytoplasmic domain," 1994, Cell 76:853-864.
Albritton et al., "A putative murine ecotropic retrovirus receptor gene encodes a multiple membrane-spanning protein and confers susceptibility to virus infection," 1989, Cell 57:659-666.
Alkhatib et al., "CC CKR5: a RANTES, MIP-1alpha, MIP-1beta receptor as a fusion cofactor for macrophage-tropic HIV-1," 1996, Science 272:1955-1958.
Baik et al., "HIV and SIV gp120 binding does not predict coreceptor function," 1999, Virology 259:267-273.
Balliet et al., "Efficient infection mediated by viral receptors incorporated into retroviral particles," 1998, J. Virol. 72:671-676.
Baltimore, "Gene therapy. Intracellular immunization," 1988, Nature 335(6189):395-396.
Bastiani et al., "Host cell-dependent alterations in envelope components of human immunodeficiency virus type 1 virions," 1997, J. Virol. 71:3444-3450.
Bates et al., "A receptor for subgroup A Rous sarcoma virus is related to the low density lipoprotein receptor," 1993, Cell 74:1043-1051.
Bates, "Chemokine receptors and HIV-1: an attractive pair?" 1996, Cell 86:1-3.
Benson et al., "Downregulation of cell-surface CD4 expression by simian immunodeficiency virus Nef prevents viral super infection," 1993, J. Exp. Med. 177:1561-1566.
Berger et al., "Chemokine receptors as HIV-1 coreceptors: roles in viral entry, tropism, and disease," 1999, Annu. Rev. Immunol. 17:657-700.
Berson et al., "A seven-transmembrane domain receptor involved in fusion and entry of T-cell-tropic human immunodeficiency virus type 1 strains," 1996, J. Virol. 70:6288-6295.
Bevec et al., "Inhibition of human immunodeficiency virus type 1 replication in human T cells by retroviral-mediated gene transfer of a dominant-negative Rev trans-activator," 1992, Proc. Natl. Acad. Sci. USA 89:9870-9874.
Biasolo et al., "A new antisense tRNA construct for the genetic treatment of human immunodeficiency virus type 1 infection," 1996, J. Virol. 70:2154-2161.
Brady et al., "Specific ablation of human immunodeficiency virus Tat-expressing cells by conditionally toxic retroviruses," 1994, Proc. Natl. Acad. Sci. USA 91:365-369.
Brelot et al., "Role of the first and third extracellular domains of CXCR-4 in human immunodeficiency virus coreceptor activity," 1997, J. Virol. 71:4744-4751.
Bubbers et al.,"Selective incorporation of H-2 antigenic determinants into Friend virus particles," 1977, Nature. 266:458-459.
Burns et al., "Vesicular stomatitis virus G glycoprotein pseudotyped retroviral vectors: concentration to very high titer and efficient gene transfer into mammalian and nonmammalian cells," 1993, Proc. Natl. Acad. Sci. U.S.A. 90:8033-8037.
Calafat et al., "Specific selection of host cell glycoproteins during assembly of murine leukaemia virus and vesicular stomatitis virus: presence of Thy-1 glycoprotein and absence of H-2, Pgp-1 and T-200 glycoproteins on the envelopes of these virus particles," 1983, J. Gen. Virol. 64:1241-1253.
Canziani et al., "Exploring biomolecular recognition using optical biosensors," 1999, Methods 19:253-269.
Caruso et al., "Selective killing of CD4+ cells harboring a human immunodeficiency virus-inducible suicide gene prevents viral spread in an infected cell population," 1992, Proc. Natl. Acad. Sci. USA 89:182-186.
Chabot et al., "N-linked glycosylation of CXCR4 masks coreceptor function for CCR5-dependent human immunodeficiency virus type 1 isolates," 2000 J. Virol. 74:4404-4413.
Chen et al., "Genetically divergent strains of simian immunodeficiency virus use CCR5 as a coreceptor for entry," 1997, J. Virol. 71:2705-2714.
Choe et al.,"The beta-chemokine receptors CCR3 and CCR5 facilitate infection by primary HIV-1 isolates," 1996, Cell 85:1135-1148.
Coffin, "HIV population dynamics in vivo: implications for genetic variation, pathogenesis, and therapy," 1995, Science 267:483-489.
Collman et al., "Infection of monocyte-derived macrophages with human immunodeficiency virus type 1 (HIV-1). Monocyte-tropic and lymphocyte-tropic strains of HIV-1 show distinctive patterns of replication in a panel of cell types," 1989, J. Exp. Med. 170:1149-1163.
Connolly et al., "A soluble form of a receptor for subgroup A avian leukosis and sarcoma viruses (ALSV-A) blocks infection and binds directly to ALSV-A," 1994, J. Virol. 68:2760-2764.
Connor et al., "Vpr is required for efficient replication of human immunodeficiency virus type-1 in mononuclear phagocytes," 1995, Virology 206:935-944.
Connor et al., "Change in coreceptor use correlates with disease progression in HIV-1-infected individuals," 1997, J. Exp. Med. 185:621-628.
Crise et al., "CD4 is retained in the endoplasmic reticulum by the human immunodeficiency virus type 1 glycoprotein precursor," 1990, J. Virol. 64:5585-5593.
Curiel et al.,"Long-term inhibition of clinical and laboratory human immunodeficiency virus strains in human T-cell lines containing an HIV-regulated diphtheria toxin A chain gene," 1993, Hum. Gene Ther. 4:741-747.
Dalgleish et al., "The CD4 (T4) antigen is an essential component of the receptor for the AIDS retrovirus," 1984, Nature 312:763-767.
Doranz et al., "Use of a gp120 binding assay to dissect the requirements and kinetics of human immunodeficiency virus fusion events", 1999, J. Virol. 73:10346-10358.
Doranz et al., "Identification of CXCR4 domains that support coreceptor and chemokine receptor functions", 1999, J. Virol. 73:2752-2761.
Doranz, "A dual-tropic primary HIV-1 isolate that uses fusin and the beta-chemokine receptors CKR-5, CKR-3, and CKR-2b as fusion cofactors", 1996, Cell 85:1149-1158.
Dragic et al., "HIV-1 entry into CD4+ cells is mediated by the chemokine receptor CC-CKR-5", 1996, Nature 381:667-673.
D'Souza et al., "Chemokines and HIV-1 second receptors. Confluence of two fields generates optimism in AIDS research", 1996, Nature Med. 2:1293-1300.
Duan et al., 1994, "Potent inhibition of human immunodeficiency virus type 1 replication by an intracellular anti-Rev single-chain antibody", Proc. Natl. Acad. Sci. USA 91:5075-5079.
Edinger et al., 1997, "Differential utilization of CCR5 by macrophage and T cell tropic simian immunodeficiency virus strains", Proc. Natl. Acad. Sci. USA 94:4005-4010.
Endres et al., "CD4-independent infection by HIV-2 is mediated by fusin/CXCR4", 1996, Cell 87:745-756.
Endres et al., "Targeting of HIV- and SIV-infected cells by CD4-chemokine receptor pseudotypes", 1997, Science 278:1462-1462.
Etemad-Moghadam et al., "Envelope glycoprotein determinants of increased fusogenicity in a pathogenic simian-human immunodeficiency virus (SHIV-KB9) passaged in vivo", 2000, J. Virol. 74:4433-4440.
Evan et al., "Isolation of monoclonal antibodies specific for human c-myc proto-oncogene product", 1985, Mol. Cell. Biol. 5:3610-3616.

(56) References Cited

OTHER PUBLICATIONS

Feng et al., HIV-1 entry cofactor: functional cDNA cloning of a seven-transmembrane, G protein-coupled receptor, 1996, Science 272:872-877.
Freed et al., "Mutational analysis of the cleavage sequence of the human immunodeficiency virus type 1 envelope glycoprotein precursor gp160", 1989, J. Virol. 63:4670-4675.
Friedman et al., "Expression of a truncated viral trans-activator selectively impedes lytic infection by its cognate virus", 1988, Nature, 335:452-454.
Garcia et al., "Serine phosphorylation-independent downregulation of cell-surface CD4 by nef", 1991, Nature 350:508-511.
Gartner et al., "The role of mononuclear phagocytes in HTLV-III/LAV infection", 1986, Science 233:215-219.
Gilbert et al., "The receptor for the subgroup A avian leukosis-sarcoma viruses binds to subgroup A but not to subgroup C envelope glycoprotein", 1994, J. Virol. 68:5623-5628.
Green et al., "A surface plasmon resonance study of albumin adsorption to PEO-PPO-PEO triblock copolymers", 1998, J. Biomed. Mater. Res. 42:165-171.
Hanafusa, 1977, "Cell transformation by RNA tumor viruses", In: Comprehensive Virology, vol. 10, Fraenkel-Conrat et al., eds., Plenum Press, New York, pp. 401-483.
He et al., "Neuropilin is a receptor for the axonal chemorepellent Semaphorin III", 1997, Cell 90:739-751.
He et al., "CCR3 and CCR5 are co-receptors for HIV-1 infection of microglia", 1997, Nature 385:645-649.
Henriksson et al., "Incorporation of wild-type and C-terminally truncated human epidermal growth factor receptor into human immunodeficiency virus-like particles: insight into the processes governing glycoprotein incorporation into retroviral particles", 1999, J. Virol. 73:9294-9302.
Hernandez et al., "Virus-cell and cell-cell fusion", 1996, Annu. Rev. Cell Dev. Biol. 12:627-661.
Heusch et al., "Intracellular immunization against SIVmac utilizing a hairpin ribozyme", 1996, Virology 216:241-244.
Ho et al., "Rapid turnover of plasma virions and CD4 lymphocytes in HIV-1 infection", 1995, Nature 373:123-126.
Hoffman et al., "Chemokines and coreceptors in HIV/SIV-host interactions", 1998, AIDS 12, Suppl. A, S17-S26.
Hoffman et al., "Stable exposure of the coreceptor-binding site in a CD4-independent HIV-1 envelope protein", 1999, Proc. Natl. Acad. Sci. USA 96:6359-6364.
Jabbar et al., "Intracellular interaction of human immunodeficiency virus type 1 (ARV-2) envelope glycoprotein gp160 with CD4 blocks the movement and maturation of CD4 to the plasma membrane", 1990, J. Virol. 64:6297-6304.
Jones et al., "Assembly of gag-beta-galactosidase proteins into retrovirus particles", 1990, J. Virol. 64:2265-2279.
Kemble et al., "Lipid-anchored influenza hemagglutinin promotes hemifusion, not complete fusion", 1994, Cell 76:383-391.
Kim et al., "Transport of cationic amino acids by the mouse ecotropic retrovirus receptor", 1991, Nature 352:725-728.
Klatzmann et al., "T-lymphocyte T4 molecule behaves as the receptor for human retrovirus LAV", 1984, Nature 312:767-771.
Koppel et al., "A 70 amino acid region within the semaphorin domain activates specific cellular response of semaphorin family members", 1997, Neuron 19:531-537.
Kuhmann et al., "Cooperation of multiple CCR5 coreceptors is required for infections by human immunodeficiency virus type 1", 2000 J. Virol. 74:7005-7015.
Kwong et al., "Structure of an HIV gp120 envelope glycoprotein in complex with the CD4 receptor and a neutralizing human antibody", 1998, Nature 393:648-659.
Labranche et al., "A single amino acid change in the cytoplasmic domain of the simian immunodeficiency virus transmembrane molecule increases envelope glycoprotein expression on infected cells", 1995, J. Virol. 69:5217-5227.
Layne et al., "HIV requires multiple gp120 molecules for CD4-mediated infection", 1990, Nature 346:277-279.
Lee et al., "Overexpression of RRE-derived sequences inhibits HIV-1 replication in CEM cells", 1992, New Biol. 4:66-74.
Lee et al., "Inhibition of human immunodeficiency virus type 1 in human T cells by a potent Rev response element decoy consisting of the 13-nucleotide minimal Rev-binding domain", 1994, J. Virol. 68:8254-8264.
Lee et al., "Epitope mapping of CCR5 reveals multiple conformational states and distinct but overlapping structures involved in chemokine and coreceptor function", 1999, J. Biol. Chem. 274:9617-9626.
Levy-Mintz et al., "Intracellular expression of single-chain variable fragments to inhibit early stages of the viral life cycle by targeting human immunodeficiency virus type 1 integrase", 1996, J. Virol. 70:8821-8832.
Littman et al., "The isolation and sequence of the gene encoding T8: a molecule defining functional classes of T lymphocytes", 1985, Cell 40:237-246.
Lo et al., "Inhibition of replication of HIV-1 by retroviral vectors expressing tat-antisense and anti-tat ribozyme RNA", 1992, Virology 190:176-183.
Lodish et al., "Specific incorporation of host cell surface proteins into budding vesicular stomatitis virus particles", 1980, Cell 19:161-169.
Maddon et al., "The T4 gene encodes the AIDS virus receptor and is expressed in the immune system and the brain", 1986, Cell 47:333-348.
Malim et al., "Stable expression of transdominant Rev protein in human T cells inhibits human immunodeficiency virus replication", 1992, J. Exp. Med. 176:1197-1201.
Marasco et al., "Design, intracellular expression, and activity of a human anti-human immunodeficiency virus type 1 gp120 single-chain antibody", 1993, Proc. Natl. Acad. Sci. USA 90:7889-7893.
Marcon et al., "Utilization of C-C chemokine receptor 5 by the envelope glycoproteins of a pathogenic simian immunodeficiency virus, SIVmac239", 1997, J. Virol. 71:2522-2527.
Mariani et al., "CD4 down-regulation by nef alleles isolated from human immunodeficiency virus type 1-infected individuals", 1993, Proc. Natl. Acad. Sci. USA 90:5549-5553.
Notice of Allowance dated Jul. 7, 2013 from U.S. Appl. No. 10/901,399, filed Jul. 28, 2004.
Deng et al., 1996, Nature 381:661-666.
Dickinson et al., 1996, Nature 382:697-700.
Dolter et al., 1993, J. Virol. 67:189-195.
Doranz et al., 1996, Cell 85:1149-1158.
Markgren et al., 1998, Anal. Biochem. 265:340-350.
McCune et al., 1988, Cell 53:55-67.
Melikyan et al., 1995, J. Cell Biol. 131:679-691.
Michaels, 1998, Analytical Chemistry 70:1242-1248.
Mirzabekov et al., 2000, Nature Biotechnology 18:649-654.
Montefiori et al., 1994, Virol. 205:82-92.
Moscovici et al., 1977, Cell 11:95-103.
Myszka et al., 1999 J. Mol. Recognit. 12:390-408.
Myszka et al., 1999, J. Mol. Recognit. 12:279-284.
Nabel et al., 1994, Hum. Gene Ther. 5:79-92.
Naldini et al., 1996, Science 272:263-267.
Nguyen et al., 2000, J. Virol. 74:3264-3272.
Pelchen-Matthews et al., 1989, EMBO J. 8:3641-3649.
Perez et al., 1987, J. Virol. 61:1609-1614.
Rich et al., 2000, Curr. Opin. Biotechnol. 11:54-61.
Rong et. al., 1995, J. Virol. 69:4847-4853.
Rong et al., 1997, J. Virol. 71:3458-3465.
Salamon et al., 1994, Biochemistry 33:13706-13711.
Salamon et al., 1997, Biophys J. 73:2791-2197.
Salamon et al., 1998, Biophys J. 75:1874-1885.
Salzwedel et al., 1993, J. Virol. 67:5279-5288.
Sarver et al., 1990, Science 247:1222-1225.
Sauter et al., 1996, J. Cell Bid. 132:795-811.
Schnell et al., 1996, Proc. Natl. Acad. Sci. USA 93:11359-11365.
Schnell et al., 1997, Cell 90:849-857.
Schubert et al., 1992, J. Virol. 66:1579-1589.
Sczakiel et al., 1992, J. Virol 66:5576-5581.
Shaheen et al., 1996, J. Virol. 70:3392-3400.
Simmons et al., 1996, J. Virol. 70:8355-8360.
Soneoka et al., 1995, Nucl. Acids Res. 23:628-633.

(56) References Cited

OTHER PUBLICATIONS

Spear et al., 1995, J. Immunol. 155:4376-4381.
Strandh et al., 1998, J. Mol. Recognit. 11:188-190.
Sullenger et al., 1990, Cell 63:601-608.
Suomalainen et al., 1994, J. Virol. 68:4879-4889.
Tamayo et al., 2001, Ultramicroscopy. 86:167-173.
Thali et al., 1993, J. Virol. 67:3978-3988.
Vogt et al., 1977, Annu. Rev. Genet. 11:203-238.
Walt, 2000, Science 287:451-452.
Wei et al., 1995, Nature 373:117-122.
Weiss et al., 1993, J. Virol. 67:7060-7066.
Weiss, 1996, Science 272:1885-1886.
Wu et al., 2001, Nature Biotechnol. 19:856-860.
Yamada et al., 1994, Gene Therapy 1:38-45.
Young et al., 1990, Science 250:1421-1423.
Zhang et al., 2000, J. Virol. 74:4634-4644.
Doranz et al., 1997, J. Exp. Med. 186:1395-1400.

* cited by examiner

NORMAL INFECTION

RECEPTOR PSEUDOTYPE INFECTION

METHOD FOR THE PRODUCTION OF ANTIBODIES THAT BIND TO MULTIPLE MEMBRANE SPANNING PROTEINS

CROSS-REFERENCE TO RELATED APPLICATIONS

This application is a divisional of U.S. patent application Ser. No. 12/720,398, filed on Mar. 9, 2010, allowed, which is a continuation of U.S. patent application Ser. No. 10/032,311, filed on Dec. 21, 2001, issued as U.S. Pat. No. 7,763,258, issued on Jul. 27, 2010, which claims benefit of U.S. Provisional Patent Application Ser. No. 60/257,988, filed on Dec. 22, 2000, abandoned. This application is a continuation-in-part of U.S. patent application Ser. No. 09/006,678, filed on Jan. 13, 1998, abandoned, which claims benefit of Ser. No. 60/047,226, filed on May 20, 1997, abandoned, each of which is incorporated herein by reference in its entirety.

GOVERNMENT SUPPORT

This invention was made with U.S. Government support (NIH Grants No. CA63531, T32-A107325, HL 07439, and R01 40880) and the U.S. Government may therefore have certain rights in the invention.

BACKGROUND OF THE INVENTION

Infection of a host cell by an enveloped virus is initiated by binding of at least one viral envelope protein to a cognate cellular virus receptor protein on the cell surface. The viral envelope protein binds to the receptor and mediates fusion of the viral envelope and the host cell membrane. The presence or absence on a cell of a cognate cellular virus receptor protein is a primary determinant of the host range and the tissue tropism of a virus.

Although an enveloped virus preferentially incorporates its own viral envelope protein(s) into the envelope during virus assembly, the tropism of a number of enveloped viruses may be altered when a different viral envelope glycoprotein is incorporated into the envelope during virus assembly by a process called phenotypic mixing or pseudotyping. Virus pseudotypes may be formed by co-infection of a cell by two different enveloped viruses or may be generated experimentally by expressing a viral envelope protein encoded by one virus in a cell infected, with another virus. Pseudotype formation in vivo has been postulated to enhance or alter the pathologic potential of an enveloped virus.

In addition to other viral envelope proteins, enveloped viruses may also incorporate a number of host surface proteins, including cellular virus receptor proteins, into their envelopes (Bubbers et al., 1977, Nature 266:458-459; Lodish et al., 1980, Cell 19:161469; Calafat et al., 1983, J. Gen. Virol. 64:12414253). For example, class I and class II major histocompatibility complex proteins, ICAM-1, ICAM-2, ICAM-3, CR3, CR4, CD43, CD44, CD55, CD59, CD63 and CD71 have been identified in the viral envelope of human immunodeficiency virus, HIV-1 (Bastiani et al., 1997, J. Virol. 71:3444-3450). Similarly, CD55 and CD59 have been identified in human cytomegalovirus virions and also in human T cell leukemia virus virions (Spear et al., 1995, J. Immunol. 155:4376-4381). The measles cellular virus receptor, CD46, has been reported in the envelope of HIV-1 (Montefiori et al., 1994, Virol. 205:82-92). In addition, transient high level expression in cultured cells of CD4, the primary cellular receptor for HIV-1, causes CD4 to partition into the envelope of a number of viruses, including retroviruses, herpesviruses, and rhabdoviruses (Dolter et al., 1993, J. Virol. 67:189-195; Schnell et al., 1996, Proc. Natl. Acad. Sci. USA 93:11359-11365; Schubert et al., 1992, J. Virol. 66:1579-1589; Young et al., 1990, Science 250:1421-1423). A number of factors influence the efficiency of cellular protein uptake by enveloped viruses including the surface density of the cellular protein, the location of the cellular protein within a cellular membrane, and the structural configuration of the cellular protein (Young et al., 1990, Science 250:1421-1423; Suomalainen et al., 1994, J. Virol. 68:4879-4889). Although there have been several reports of incorporating cellular virus receptor proteins into viruses, the structural and functional integrity of these proteins was not suggested, tested, used, or demonstrated previously (Montefiori et al., 1994, Virol. 205:82-92; Dolter et al., 1993, J. Virol. 67:189-195; Schnell et al., 1996, Proc. Natl. Acad. Sci. USA 93:11359-11365; Schubert et al., 1992, J. Virol. 66:15794589; Young et al., 1990, Science 250:1421-1423).

Intracellular immunization as a method of gene therapy has been proposed as a potential treatment for AIDS (Friedman et al., 1988, Science 335:452-454; Baltimore, 1988, Science 335:395-396). It has been proposed that the immune system of an AIDS patient may be reconstituted with hematopoietic stem cells that have been rendered resistant to viral infection by the introduction of a gene or a plurality of genes which protect the cell against HIV infection. Numerous intracellular antagonists of HIV replication have been developed which exhibit potent antiviral properties in vitro including trans-dominant mutants (Bevec et al., 1992, Proc. Natl. Acad. Sci. USA 89:9870-9874; Malim et al., 1992, J. Exp. Med. 176:1197-1201; Bahner. et al., 1993, J. Virol. 67:3199-3207; Nabel et al., 1994, Hum. Gene Then 5:79-92), molecular decoys (Sullenger et al., 1990, Cell 63:601-608; Lee et al., 1992, New Biol. 4:66-74; Lee et al., 1994, J. Virol. 68:8254-8264), intracellular antibodies (Marasco et al., 1993, Proc. Natl. Acad. Sci. USA 90:7889-7893; Duan et al., 1994, Proc. Natl. Acad. Sci. USA 91:5075-5079; Shaheen et al., 1996, J. Virol. 70:3392-3400; Levy-Mintz et al., 1996, J. Virol. 70:8821-8832), anti-sense RNA (Lo et al., 1992, Virology 190:176-183; Sczakiel et al., 1992, J. Virol. 66:5576-5581; Biasolo et al., 1996, J. Virol. 70:2154-2161), ribozymes (Sarver et al., 1990, Science 247:1222-1225; Yamada et al., 1994, Gene Therapy 1:38-45; Heusch et al., 1996, Virology 216:241-244), and other antagonists (Caruso et al., 1992, Proc. Natl. Acad. Sci. USA 89:182-186; Curiel et al., 1993, Hum. Gene Ther. 4:741-747; Brady et al., 1994, Proc. Natl. Acad. Sci. USA 91:365-369).

CD4 has long been known as the cell-surface protein necessary for HIV binding to and entry into cells (Dalgleish et al., 1984. Nature 312:763-767; Klatzmann et al., 1984, Nature 312:767-771; Maddon et al., 1986, Cell 47:333-348). Hence, CD4 is a cellular virus receptor protein for HIV. Recently, chemokine receptors have been shown to also be components of the HIV receptor complex and are important determinants of HIV-1 tropism (Bates, 1996, Cell 86:1-3; D'Souza et al., 1996, Nature Med. 2:1293-1300; Weiss, 1996, Science 272; 1885-1886). HIV envelope proteins interact with CD4 and chemokine receptors present on the surface of a cell, resulting in binding of the virus to the cell followed by virus-mediated fusion of the viral envelope and the cell membrane. Initial binding of the HIV envelope protein, gp120, to CD4 triggers one or more conformational changes in one or more HIV viral envelope glycoproteins. Subsequent interaction of an HIV envelope protein with a chemokine receptor on the surface of the cell causes exposure of the viral gp41 fusion peptide to the cell membrane, and ultimately results in fusion of the viral envelope and cell membrane (Collman et al., 1989, J. Exp. Med. 170:1149-1163).

Chemokine receptors are seven transmembrane-spanning G-protein coupled receptors and are divided into two classes, the CC-class and the CXC-class of chemokine receptors. These two classes of chemokine receptors differ in their tissue distribution, their ligand specificity, and their capacity to specifically interact with particular viruses, including particular isolates of HIV and SIV. CCR5 is a chemokine receptor in the CC-class and CXCR4 is a chemokine receptor in the CXC-class.

The ability of HIV-1 to infect T-cells is well known. T-cell tropic strains of HIV-1 undergo envelope-mediated fusion with and enter into T-cells only if the T-cells express both CXCR4 and CD4 (Berson et al., 1996, J. Virol. 70:6288-6295; Feng et al., 1996, Science 272:872-877).

Macrophages and other mononuclear phagocytes are an important reservoir for virus replication in HIV-infected individuals and are suspected to be a major source of ongoing virus replication in patients receiving anti-retroviral therapy (Gartner et al., 1986, Science 233:215-219; Ho et al., 1995, Nature 373:123-126; Wei et al., 1995, Nature 373:117-122; Coffin, 1995, Science 267:483-489). Macrophage-tropic strains of HIV-1 undergo envelope mediated fusion with and enter into macrophages only if the macrophages express both CCR5 and CD4 (Choe et al., 1996, Cell 85:1135-1148; Doranz et al., 1996, Cell 85:1149-1158; Deng et al., 1996, Nature 381:661-666; Dragic et al., 1996, Nature 381:667-673; Alkhatib et al., 1996, Science 272:1955-1958). Similarly, SW undergoes envelope mediated fusion with and enters into cells only if the cells express both CCR5 and CD4, although other unidentified cellular virus receptor proteins have been also implicated in SIV infection (Chen et al., 1997, J. Virol. 71:2705-2714; Edinger et al., 1997, Proc. Natl. Acad. Sci. USA 94:4005-4010; Marcon et al., 1997, J. Virol. 71:2522-2527). Many primary isolates of HIV-1 are capable of undergoing envelope mediated fusion with and entering into cells which express CD4 and at least one chemokine receptor, including, but not limited to, CXCR4 and CCR5 (Choe et al., 1996, Cell 85:1135-1148; Doranz et al., 1996, Cell 85:1149-1158; Simmons et al., 1996, J. Virol. 70:8355-8360; Connor et al., 1997, J. Exp. Med. 185:621-628; He et al., 1997, Nature 385:645-649). Therefore, expression of chemokine receptors or other cellular virus receptor proteins on the surface of cells appears to be a major determinant of enveloped viral tropism.

Young et al. have demonstrated that CD4 is efficiently incorporated into the envelopes of retroviral particles. However, these particles failed to enter cells expressing HIV envelope glycoproteins (Young et al., 1990, Science 250:1421-1423). Recently, Schnell et al. reported that CD4 may be packaged into vesicular stomatitis virus (Schnell et al., 1996, Proc. Natl. Acad. Sci. USA 93:11359-11365). Thus, to date, production of virus particles comprising host cell receptors or other surface proteins while preserving the biological function of the molecule, has not been achieved.

Ligand interactions with membrane proteins are responsible for a multitude of cell adhesion, signaling, and regulatory events. This diversity of functions makes membrane proteins, such as seven transmembrane domain (7™) receptors, important drug targets. Proteins that span the membrane multiple times present a unique set of challenges for ligand binding studies because they require a lipid environment to maintain native structure. Whereas detergent conditions can occasionally be found that allow native structure to be maintained in solution, this is an empirical and frequently time-consuming process. As a result, ligand binding studies involving 7™ and many other membrane proteins typically involve using whole cells or vesicles derived from cell membranes, where the protein of interest is a minor component.

Interactions between the HIV-1 envelope (Env) protein and its receptors underscore both the strengths and weaknesses of cell-surface binding assays. HIV-1 Env mediates virus entry by sequentially binding to CD4 and a coreceptor, with these interactions triggering conformational changes in Env that lead to membrane fusion (Berger et al., 1999, AMU. Rev. Immunol. 17:657-700). R5 virus strains that are responsible for virus transmission use the 7™ chemokine receptor CCR5 in conjunction with CD4 to enter cells, X4 virus strains that tend to evolve years after infection use the related CXCR4 receptor, and intermediate dual-tropic R5X4 virus strains can use both receptors. Binding of the soluble gp120 subunit of Env to CD4 is readily detected, and gp120 proteins from some R5 virus strains bind to CCR5 with high affinity (Doranz et al., 1999, J. Virol. 73:10346-10358 and Doranz et al., 1999, J. Virol. 73:10346-10358). However, direct binding of X4 gp120 proteins to CXCR4 has been difficult to measure, as has binding of R5X4 gp120 proteins to either CXCR4 or CCR5 (Doranz et al., 1999, J. Virol. 73:2752-2761, Balk et al., 1999, Virology 259:267-273 and Etemad-Moghadam et al., 2000, J. Virol. 74:4433-4440). Interactions between Env and alternative coreceptors such as CCR3 and STRL33 also cannot be measured using standard binding techniques (Baik et al., 1999, Virology 259:267-273). As virus receptor interactions can be the targets of neutralizing antibodies and small molecule inhibitors (reviewed in ref 1), improved assays to measure these binding events are needed.

An approach that in principle would make it possible to monitor low affinity but functionally important Env-coreceptor interactions would be to use microfluidic devices, e.g., biosensors (optical and SPR biosensors), and other analytical instruments that detect interactions between molecules, preferably in real-time. The most commonly used optical biosensors (Biacore, Uppsala, Sweden) are based on surface plasmon resonance, which measures changes in refractive index at the sensor surface (Cauziani et al., 1999, Methods 19:253-269 and Rich et al., 2000, Curr. Opin. Biotechnol. 11:54-61). With this technique, one protein is tethered to the biosensor surface, and changes in refractive index that occur upon exposure to its binding partner are monitored. However, a general method for attaching intact membrane proteins to this instrument does not exist. Membrane proteins can span the membrane multiple times, can form homo- or hetero-oligomers in the membrane, and removal from the lipid bilayer can destroy tertiary or quaternary structure. Thus, despite the importance of membrane proteins in biological processes, to date, there is no method to study the complex interaction between these molecules and molecules that specifically interact with them using powerful techniques such as, but not limited to, using optical biosensors.

To date, there are a limited number of therapies directed against HIV infection in humans, each having a variable success rate, generally concomitant with the emergence of strains of HIV which are resistant to the therapy. There remains an acute need for the development of anti-HIV therapies to which the virus cannot develop resistance. The present invention satisfies this need.

Further, there is long-felt need for assays for the study of cell membrane protein-protein interactions, and the present invention also satisfies this need.

SUMMARY OF THE INVENTION

The invention includes an isolated lipoparticle comprising a multiple membrane spanning protein wherein the protein is not CD63. In one aspect, the protein is capable of binding with a ligand under conditions wherein the ligand would bind with an otherwise identical protein present on a cell membrane.

In another aspect, the lipoparticle is a virus.

In yet another aspect, the virus is a membrane-enveloped virus.

In a further aspect, the membrane-enveloped virus is a retrovirus.

In an even further aspect, the virus is selected from the group consisting of a murine leukemia virus, a human immunodeficiency virus, a rabies virus, a Rous sarcoma virus, and a vesicular stomatitis virus.

In another aspect, the protein is selected from the group consisting of a G-protein coupled receptor, a transporter protein, and an ion channel protein.

In one aspect, the protein is selected from the group consisting of CCR5, CXCR4, MCAT-1, CXCR2, CXCR3, mu-opioid receptor, and KCNH2 potassium channel protein.

The invention includes a composition comprising an isolated lipoparticle attached to a sensor surface, the lipoparticle further comprising a membrane spanning protein.

In one aspect, the protein is selected from the group consisting of a transport protein, a G-protein coupled receptor, an ion channel protein, a type I membrane protein, and a type II membrane protein.

In another aspect, the G-protein coupled receptor is selected from the group consisting of a mu-opioid receptor, a CXCR2, CXCR3, CXCR4, a CCR5, a CCR8, a XCR1, and a CX3CR1.

In yet another aspect, the ion channel protein is selected from the group consisting of KCNH2 potassium channel protein, Kv1.3 potassium channel protein, and CFTR protein.

In a further aspect, the transporter protein is selected from a group consisting of a glucose transporter protein and an amino acid transporter protein.

In another aspect, the type I membrane protein is selected from the group consisting of CD4, Tva, and neuropilin-2.

In yet another aspect, the type II membrane protein comprises DC-specific ICAM-3 grabbing nonintegrin (DC-SIGN).

In one aspect, the lipoparticle is a virus.

In another aspect, the virus is a membrane-enveloped virus.

In yet another aspect, the membrane-enveloped virus is a retrovirus.

In a further aspect, the virus is selected from the group consisting of a murine leukemia virus, a human immunodeficiency virus, a rabies virus, a Rous sarcoma virus, and a vesicular stomatitis virus.

In another aspect, the lipoparticle further comprises a plastic bead core to form a proteoliposome.

In yet another aspect, the sensor comprises a microfluidic device.

In a further aspect, the microfluidic device is a biosensor.

In another aspect, the biosensor is an optical biosensor.

In a further aspect, the optical biosensor measures surface plasmon resonance (SPR).

In yet another aspect, the surface is located on a biosensor chip.

In another aspect, the biosensor chip is selected from the group consisting of a gold coated biosensor chip, a gold and dextran coated biosensor chip, and a derivatized gold biosensor chip.

The invention also includes a method of assessing the binding interaction of a membrane spanning protein with a ligand. The method comprises (a) producing a lipoparticle comprising a membrane spanning protein; (b) attaching the lipoparticle to a substrate; (c) contacting the protein present on the lipoparticle with a ligand of the protein; and (d) detecting any change in the substrate compared with any change in an otherwise identical substrate wherein the protein present on the lipoparticle is not contacted with the ligand, wherein detecting a change in the substrate wherein the protein present on the lipoparticle is contacted with the ligand compared with the otherwise identical substrate wherein the protein present on the lipoparticle is not contacted with the ligand assesses the binding interaction of the protein with the ligand.

In one aspect, the detecting in (d) is performed using a microfluidic device and the substrate is a sensor surface.

In another aspect, the microfluidic device is a biosensor device.

In yet another aspect, the biosensor device comprises a microchannel or a microwell.

In a further aspect, the biosensor is an optical biosensor.

In yet a further aspect, the optical biosensor is a surface plasmon resonance biosensor device.

The invention includes a method of identifying a potential ligand of a membrane protein. The method comprises (a) attaching a lipoparticle comprising a membrane protein to a surface; (b) contacting the protein with a test ligand; and (c) comparing the surface comprising the lipoparticle comprising the protein contacted with the test ligand with an otherwise identical surface comprising an otherwise identical lipoparticle comprising a protein not contacted with the test ligand, wherein a difference between the surface comprising the lipoparticle comprising a protein contacted with the test ligand compared with the otherwise identical surface comprising the otherwise identical lipoparticle comprising the protein not contacted with the test ligand is an indication that the ligand is a potential ligand of the protein.

The invention includes a ligand identified by this method.

In one aspect, the comparing in (c) is performed using a microfluidic device.

In another aspect, the microfluidic device is a biosensor device.

In yet another aspect, the protein is selected from a multiple membrane spanning protein and a single membrane spanning protein.

In another aspect, the multiple membrane spanning protein is selected from the group consisting of a G-coupled protein receptor (GCPR), a transporter, and an ion channel.

In a further aspect, the single membrane spanning protein is selected from the group consisting of a type I membrane protein and a type H membrane protein.

in another aspect, the test ligand is selected from the group consisting of a protein and a chemical compound.

In yet another aspect, the protein is an antibody.

The invention includes a method of identifying a compound that affects binding between a ligand and a membrane protein receptor. The method comprises (a) attaching a lipoparticle comprising a membrane protein to a surface; (b) contacting the protein with a known ligand under conditions wherein the protein specifically binds with the ligand; (c) contacting the lipoparticle of (b) with a test compound; and (d) comparing the surface comprising the lipoparticle contacted with the test compound with an otherwise identical surface comprising an otherwise identical lipoparticle not contacted with the test compound, wherein a difference between the surface comprising the lipoparticle contacted with the test compound compared with the otherwise identical surface comprising the otherwise identical lipoparticle not contacted with the test compound is an indication that the test compound affects between the ligand and the membrane protein receptor.

The invention includes a kit for assessing the binding interaction of a membrane spanning protein with a ligand. The kit comprising a lipoparticle comprising a membrane spanning protein and a substrate, the kit further comprising an applicator, and an instructional material for the use thereof.

In one aspect, the kit further comprises a ligand of the protein.

The invention includes a kit for identifying a potential ligand of a membrane protein. The kit comprises a lipoparticle comprising a membrane protein and a surface, the kit further comprises an applicator, and an instructional material for the use thereof.

In one aspect, the kit further comprises a test ligand.

The invention also includes a kit for identifying a compound that affects binding between a ligand and a membrane protein receptor. The kit comprises a lipoparticle comprising a membrane protein and a surface. The kit further comprises an applicator, and an instructional material for the use thereof.

In one aspect, the kit further comprises a test compound.

In another aspect, the kit further comprises a known ligand of the membrane protein.

BRIEF DESCRIPTION OF THE DRAWINGS

FIG. 2, comprising

FIG. 3, comprising FIGS. 1A and 3B, is a pair of bar graphs depicting the results of experiments in which enveloped virus vectors were contacted with CEMx174 cells treated with α-CD4#19 antibody, which antibody binds specifically to CD4. In FIG. 3B, the enveloped virus vector used in each experiment was pre-incubated with one of two antibodies as in Panel A (striped bars), or the vector was not preincubated with an antibody and one of the two antibodies was added sixteen hours after the vector and cells were mixed (solid bars).

FIG. 5, comprising In FIG. 5A, an antibody which specifically binds to MLV Gag protein was used to visualize Gag protein. In FIG. 5B, an antibody which specifically binds to Tva protein was used to visualize Tva protein.

FIG. 6, comprising FIGS. 6A and 613, is a pair of graphs depicting the inhibitory effects of a protein on the ability of MLV(Tva) to fuse with 3T3EnvA cells. The graph in FIG. 6A depicts results obtained using anti-Tva, an antibody which specifically binds to Tva and which interferes with the interaction between Tva and EnvA. The graph in FIG. 6B depicts the results using sTva, a soluble form of Tva. "% inhibition" refers to the decrease in the number of cells which fused with the enveloped virus vector, which decrease was observed in the presence of the indicated concentration of the indicated compound, relative to when the compound was not present.

FIGS. 8A and 8B, is an image of Western blots of MLV pseudotypes. FIG. 8A is an image of a Western blot demonstrating that MLV particles were produced by cotransfection of 293T cells with plasmids expressing MLV gag and either the indicated receptor constructs or an empty pcDNA3vector (MLV-pcDNA3). Purified MLV-pcDNA3, MLV-CCR5, MLV-CXCR4, and MLV-CD4 particles were analyzed by Western blot using antibodies against the various receptors and the MLV gag protein as indicated. FIG. 8B is an image depicting a Western blot where fractions from an equilibrium density gradient containing MLV-CCR5 were analyzed by SDS-PAGE and Western blot using antibodies to CCR5 (Upper panel) and MLV-gag (Lower panel). Densities of each fraction are indicated (in g/ml), and a CCR5 standard was run in the far right lane to control for expression.

FIGS. 9A through 9F, are graphs depicting antibody binding to chemokine receptor pseudotypes. FIG. 9A depicts equivalent amounts of MLV-CXCR4 and MLV-pcDNA3 were attached to a Biacore F1 chip. Binding of 333 nM 12G5 (anti-CXCR4 antibody) and 666 nM CTC8 (anti-CCR5 antibody) to MLV-CXCR4 and MLV-pcDNA3 is demonstrated. Binding was measured for 120 seconds before washing with PBS running buffer for an additional 120 seconds to measure dissociation. Regeneration pulses are indicated by bars. Instrument noise between the regeneration pulses is due to changes in flowrate and the injections of the regeneration buffer, which lead to immediate shifts in the signal baseline. The slower changes in signal reflect binding of proteins to the sensor surface. FIG. 9B depicts an assay wherein equivalent amounts of MLV-CCR5 and MLV-pcDNA3 were attached to a Biacore F1 chip, and the binding of 400 nM CTC8 or 800 nM 12G5 to MLV-CCR5 and MLV-pcDNA3 is shown. A single regeneration pulse (bar) was used to strip bound antibody. FIG. 9C depicts data from six sequential injections of 166 nM 12G5 to MLV-pcDNA3 and MLV-CXCR4 are overlayed. In all cases, and in all subsequent figures, the sensorgrams show subtracted data, in which the signal obtained from the control surface is subtracted from the signal obtained from the surface bearing receptor-positive particles. Binding was measured for 60 seconds. Regeneration conditions were similar to those used in FIG. 9A.

FIG. 9D depicts subtracted data from the binding of 5 nM12G5 to MLV-CXCR4 and MLV-pcDNA3 which is shown in green. After regeneration, binding in the presence of the CXCR4 inhibitor ALX40-4C (at 4 mM) is shown in red, whereas binding of the antibody following washout of the inhibitor is shown in blue. FIG. 9E Subtracted data for serial injections of 111 nM 12G5 to MLV-CXCR4 and MLV-pcDNA3 at different flow rates are shown. Regeneration conditions were similar to those used in A. FIG. 9F Subtracted data from binding of serial dilutions of CTC8 to MLV-CCR5 and MLV-pcDNA3 are shown.

FIGS. 11A-11C, is a graph depicting HIV-1 gp120 binding to MLV-CXCR4. FIG. 11A Equivalent amounts of MLV-pcDNA3 and MLV-CXCR4 were attached to a Biacore C1 chip, and the binding of 400 mM 8×gp120 was measured to both surfaces in a running buffer of DMEM with 0.1% Pluronic F127. Binding was measured for 120 seconds and dissociation for 300 seconds. Two brief regeneration pulses with pH 9/NaCl were used to strip gp120 from the surface. The signal from the pcDNA3 control surface was subtracted in B and C. FIG. 11B is an image demonstrating the ability of mAb 17b, which binds to the conserved coreceptor binding site in Env, to block 8× binding to CXCR4 was measured. Subtracted data for the association phase of 150 mM 8× to MLV-CXCR4 and MLV-pcDNA3 are shown (8×). Association of 750 nM 17b alone and 150 nM 8× prebound to 750 nM 17b is also shown. These experiments were performed using a Biacore F1 chip in PBS running buffer. Regeneration was achieved previously herein in FIG. 8A, supra. FIG. 11C, this is an image depicting subtracted data for binding of serial dilutions of 8×gp120 to MLV-CXCR4 and MLV-pcDNA3.

FIGS. 12A and 12B, depicts binding of collapsin-1 to MLV-NP-1 pseudotypes. FIG. 12A is an image of a western blot depicting MIL-NP-1, MLV-Plx-2, MLV-CCR5, and MLV-CXCR4 preparations blotted with an antibody against the myc epitope, which was present on the C terminus of the NP-1 and Plx-2 constructs, Equivalent amounts of MLV gag were present in these samples. FIG. 12B is a graph depicting equivalent amounts of MLV-CCR5 and NP-1 attached to a Biacore C1 chip, and binding of 200 nM collapsin-1 was measured to both surfaces in PBS running buffer. The sensorgram shows the MLV-CCR5 signal subtracted from the MLV-NP-1 surface. Collapsin-1 was injected for 150 seconds, and the arrow indicates the beginning of the wash step. A brief pulse with 2 M $MgCl_2$ was sufficient to regenerate the surface following binding.

DETAILED DESCRIPTION OF THE INVENTION

Figure 1:
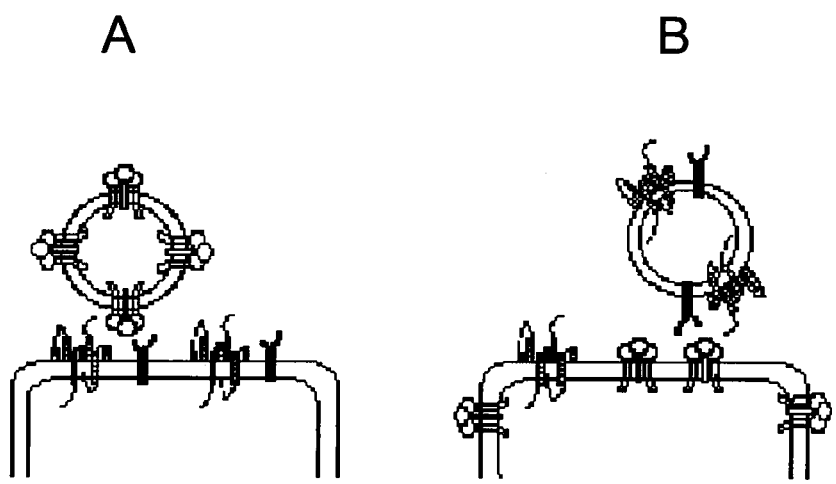
FIG. 1 is a pair of diagrams depicting the location of viral envelope proteins and cellular virus receptor proteins on the surfaces of viruses and cells. In Panel A, a diagram of the envelope of a virus having a viral envelope protein embedded in the envelope thereof is depicted along with a diagram of a cell membrane having at least two different cellular virus receptor proteins embedded therein. In Panel B, there is depicted a diagram of an enveloped virus vector of the invention, wherein the envelope of the vector comprises two different cellular virus receptor proteins. Also in Panel B, there is depicted a diagram of a cell membrane having a viral envelope protein embedded therein.

The invention relates to an enveloped virus vector which comprises a cellular virus receptor protein and which is capable of fusing with a cell which comprises a viral envelope protein to which the cellular virus receptor protein is cognate. In certain embodiments, the enveloped virus vector comprises a plurality of cellular virus receptor proteins.

The invention also relates to methods of making the enveloped virus vector of the invention including, but not limited to, a method involving a producer cell which comprises a cellular virus receptor protein and a method involving a producer cell which does not normally comprise a cellular virus receptor protein.

The invention further relates to methods of using the enveloped virus vector of the invention including, but not limited to, a method of directing delivery of a composition to a cell, particularly to an enveloped virus-infected cell, a method of altering a property such as the host range or tissue tropism of an enveloped virus, a method of rendering a cell susceptible to fusion with an enveloped virus or an enveloped virus vector, a method of producing a cellular virus receptor protein, a method of identifying a viral envelope protein, a method of identifying a cellular virus receptor protein, and a method of identifying a composition capable of affecting the interaction between a viral envelope protein and a cellular virus receptor protein which is cognate thereto.

The invention also relates to methods of using the enveloped virus of the invention to assess protein-protein binding interactions using methods such as, but not limited to, microfluidics-based assays. The enveloped virus vector, also referred to herein as a lipoparticle, allows presentation of a cell membrane protein while preserving its biological function, such that the interaction of the protein with its cognate ligand can be studied.

The Enveloped Virus Vector of the Invention

Infection of a host cell by an enveloped virus involves the interaction of at least one virus-encoded viral envelope protein, which is located on the outer surface of the viral envelope, with at least one cognate cell-encoded cellular virus receptor protein, which is associated with the outer surface of the host cell outer membrane. The invention relates to the discovery that an enveloped virus vector comprising a cognate cellular virus receptor protein is capable of fusing with a cell comprising a viral envelope protein.

The enveloped virus vector of the invention is a virus-like particle which comprises a protein, wherein the biological activity or function, conformation, or both, of the protein are retained compared with the activity, function or conformation of the protein present in its native state in a membrane. For instance, where the protein is a cellular virus receptor protein, the enveloped virus vector is capable of binding to and fusing with a target cell which comprises a viral envelope protein to which the cellular virus receptor protein is cognate.

The ability of the cellular virus receptor protein to interact with molecules in the solvent in which the vector is suspended, when the cellular virus receptor protein is a component of the vector, is analogous to the ability of the cellular virus receptor protein to interact with molecules in the extracellular solvent when the cellular virus receptor protein is expressed on the surface of a cell. Likewise, the ability of the membrane protein of the lipoparticle is analogous to the ability of the membrane protein to interact with a molecule when the membrane protein is expressed on the surface of a cell.

This is so, even where the lipoparticle is attached to a support, such as, but not limited to, a sensor chip.

Moreover, the enveloped virus vector, also referred to herein as a lipoparticle, comprises, in essence, an exterior lipid bilayer comprising a membrane protein. Thus, the lipoparticles of the invention comprise a simple membrane in which a protein of interest can be embedded while maintaining the normal structure, function, or both, of the protein. That is, the membrane protein may not retain a detectable function in a lipoparticle since this is partly determined by intracellular pathways that may or may not be present inside the lipoparticle. Preferably, however, the membrane protein maintains its structure compared with the native protein when present in the membrane. As exemplified herein, the membrane protein when present in a lipoparticle can mediate virus fusion thereby also maintaining its function as mediating membrane fusion because no intracellular proteins are needed for fusion. The same would not be the case for, e.g., GCPR signaling, because intracellular G-proteins and downstream pathways may be necessary for the protein to function as it does when present in its native form in the membrane. A "lipoparticle," as that term is used herein, means a small particle of about a nanometer to about one micrometer, comprising a lipid bilayer further comprising a protein where the protein can interact with a cognate ligand essentially as it would otherwise interact with the ligand when the protein is present in an intact membrane. The lipoparticle does not encompass cell membrane vesicles, which are typically produced using empirical methods and which are usually heterogeneous in size. The lipoparticle of the invention is, preferably, dense, spherical and/or homogeneous in size.

The data disclosed herein demonstrate, for the first time, that complex cell membrane proteins, which can, but need not, span the lipid bilayer many times, can be presented in the context of a relatively simple lipid bilayer of, for example, a virus vector particle and yet, surprisingly, the protein retains its biological structure, function, or both. That is, the data disclosed herein demonstrate that seven transmembrane domain proteins, such as chemokine receptors, can be embedded in a virus vector, i.e., a lipoparticle, and can mediate fusion of the virus vector with a cell where the cell expresses a cognate binding partner that binds with the transmembrane protein. This discovery makes it possible not only to use the virus vector to deliver a substance of interest to a cell expressing any target protein for which a cognate receptor is known, but also makes possible the study of complex protein-protein interactions between a membrane protein and its cognate ligand(s).

The lipoparticle allows the stable presentation of structurally intact complex membrane proteins within a particulate format that is suitable for gene delivery, microfluidics, biosensors, and antigen presentation. That is, because the structure of complex membrane proteins can be maintained using the lipoparticle, the present invention includes methods of using lipoparticles comprising a membrane protein of interest as an immunogenic vector for production of antibodies that specifically bind with the membrane protein. The antibodies produced by this method can bind with the protein in its native structure and thus can provide a method for producing antibodies that can for instance, inhibit protein function by steric blocking of important sites on the protein and/or antibodies that can affect protein, function by allosteric effect.

The enveloped virus vector of the invention can comprise one more cellular virus receptor proteins. Although the Examples described herein disclose enveloped virus vectors which comprise one or two cellular virus receptor proteins, one skilled in the art is enabled by the teaching provided herein to produce an enveloped virus vector comprising any number of cellular virus receptor proteins in the envelope thereof. Indeed, one skilled in the art, based on the disclosure provided herein, would appreciate that the invention encompasses any membrane protein and any protein typically present in a membrane can be inserted into the lipoparticles of the invention thereby presenting the protein in its native conformation and/or preserving it's binding affinity of a cognate ligand or binding partner.

Indeed, the data disclosed herein demonstrate that, surprisingly, complex cell membrane protein can, within the context of a simple virally derived lipid bilayer, can form complexes and can interact such that function of the protein is conserved. More specifically, the data demonstrate that CD4 and a chemokine receptor present on the lipoparticle can interact and bind with the viral env when the cell membrane proteins are present on a viral membrane. These unexpected results demonstrate that the lipoparticle can comprise multiple membrane proteins wherein the proteins can form homo- and/or heterodimers, or otherwise interact, substantially as they would otherwise do in the context of the membrane where they are typically found. Thus, the present invention includes a lipoparticle comprising at least one multiple membrane spanning protein and can further comprise additional membrane components that can interact with the protein in a manner substantially similar to the interaction of these components in an intact membrane.

It is known in the art that enveloped virus particles can be produced which are missing one or more of the ordinary components of such particles, such as a portion of the genome of the enveloped virus (Volt et al., 1977, Annu. Rev. Genet, 11:203-238; Hanafusa, 1977, In: *Comprehensive Virology*, vol. 10, Fraenkel-Conrat et al., eds., Plenum Press, New York, pp. 401.483). Such virus particles are referred to herein as defective. Enveloped virus vectors comprising such a defective virus particle and a cellular virus receptor protein are included in the present invention. It is contemplated that the omission of one or more components of such particles provides an opportunity to substitute an additional component in place of the missing component. In addition, numerous viruses known in the art that are able to accommodate the presence of an additional component without deletion of a component of the virus. By way of example, the additional component may be a nucleic acid, an antisense nucleic acid, a gene, a protein, a peptide, Vpr protein, an enzyme, an intracellular antagonist of HIV, a radionuclide, a cytotoxic compound, an antiviral agent, an imaging agent, and the like.

The enveloped virus vector of the invention may comprise additional components beyond those specifically recited herein. The suitability of the enveloped virus vector of the invention for specifically targeting cells of one or more particular phenotypes renders the vector an appropriate vehicle for delivering these additional components to such cells, the additional component being any one or combination of those recited herein.

Similarly, the lipoparticles of the invention can be used to assess the binding of the protein presented in the lipid bilayer of the particle with a test component and or to assess the effect of a test compound on the binding of the protein with a cognate ligand. This is because, as more fully set forth elsewhere herein, the protein embedded in the lipoparticle retains its ability to bind with its cognate ligand(s) and because the protein, now present in a lipoparticle, can be used in assays where soluble proteins or whole cells cannot be used, such as assays where the protein of interest must be bound to a support or substrate, including, but not limited to, an assay using a microfluidic device, e.g., a biosensor assay.

However, the present invention is not limited to any particular assay. Rather, the present invention encompasses any assay where the protein of interest is a membrane component and where study of the binding of the protein with a ligand requires, or is facilitated by, presenting the protein in the context of a lipid bilayer and/or attaching the protein to a support or solid substrate. Such assays include, but are not limited to, assays using a microfluidic device, e.g., an optical biosensor, PATIR-FTIR spectroscopy, which is a type of biosensor using total internal reflection Fourier-transform infrared spectroscopy (1998, Chem. Phys. Lipids 96:69-80), CPRW Biosensor (Coupled plasmon-waveguide resonance (CPWR) spectroscopy as described in Salamon et al. (1997, Biophys J. 73:2791-2197) and Salmon et al. (1998, Biophys J. 75:1874-1885), Multipole Coupling Spectroscopy (MCS) as described in Signature Biosciences, www.signaturebio.com, Fiber optic biosensors (Illumina) as described in Walt (2000, Science 287:451-452) and Dickinson et al. (1996, Nature 382:697-700), Michaels (1998, Analytical Chemisty 70:12424248), Lab-on-a-chip microfluidics (manufactured by, e.g., Caliper and Aclara) as described in Sundberg et al. (Current Opin. in Biotech. 11:47-53), and Bousse et al. (1999, Electrokinetic Microfluidic Systems, SPIE Microfluidic Devices and Systems II 3877:2-8, 9/20/99-9/21/99), Microchannels (Gyros' microchannels etched into a Compact Disc-based device) as described in www.gyros.com, Microcantilevers (Protiveris) as described in Tamayo et al., 2001, Ultramicroscopy. 86:167473), Wu et al. (2001, Nature Biotechnol. 19:856-860), Confocal microscopy and nanowell detection as described in Hunt et al. (International Publication No. WO 01/02551), and Microwell binding assays. The aforementioned, as well as similar assays known in the art or to be developed in the future, are encompassed in the invention.

As more fully set forth elsewhere herein, the lipoparticle of the invention, comprising a membrane protein of interest, can be used in a wide variety of applications as would be appreciated by the skilled artisan once armed with the teachings disclosed herein. More particularly, the lipoparticle can be used in assays relating to, for example, but not limited to, drug screening, peptide screening, agonist versus antagonist discrimination, ADMET studies, structure-activity relationships studies, vaccine development, food testing, chemical sensing, light sensing, content release, monoclonal antibody production, fusion studies, phage display methods, ligand "fishing" or identification, protein interaction mapping, various diagnostics, and production of artificial cells, among many others. Such uses would be understood by the skilled artisan to be encompassed in the invention based upon the disclosure provided herein.

The combination of the enveloped virus vector of the invention with a pharmaceutically acceptable carrier is specifically contemplated as a method for providing the enveloped virus vector of the invention to a human.

The pharmaceutical compositions useful for practicing the invention may be administered to deliver a dose of between 1 nanograms per kilogram per day and 100 milligrams per kilogram per day of the enveloped virus vector.

Pharmaceutical compositions that are useful in the methods of the invention may be administered systemically in oral solid formulations, ophthalmic, suppository, aerosol, topical, intravenous, or other similar formulations. In addition to the enveloped virus vector, such pharmaceutical compositions may contain pharmaceutically acceptable carriers and other ingredients known to enhance and facilitate enveloped virus vector administration. Other possible formulations, such as nanoparticles and liposomes may also be used to administer an enveloped virus vector according to the methods of the invention.

It is contemplated that the enveloped virus vector may be used to deliver an additional component to a cell for therapeutic, diagnostic, or prophylactic purposes. By way of example, the methods described herein may be used to generate an enveloped virus vector wherein the luciferase gene present in NL-R⁻E⁻luc provirus used in Example 1 is replaced, using methods well known in the art, with a gene encoding a protein having cytotoxic or therapeutic properties. The resulting enveloped virus vector may be used to selectively kill or treat, respectively, HIV-infected cells in a patient to whom the resulting enveloped virus vector is administered.

As demonstrated by the specific embodiments described herein, one skilled in the art may use the methods described herein to construct a wide variety of enveloped virus vectors, each having an envelope which comprises at least one cellular virus receptor protein. By way of example, cells infected with RSV express EnvA, a viral envelope protein of RSV, on their surface. An enveloped virus vector having an envelope which comprises Tva, the cellular virus receptor protein which is cognate to EnvA, may be used to infect cells which are infected with RSV. Similarly, an enveloped virus vector having an envelope which comprises CD4 and CCR5 may be used to infect cells which are infected with HIV.

In one embodiment, the enveloped virus vector is designed to specifically target cells infected with a particular enveloped virus. In this embodiment, the cellular virus receptor protein of the enveloped virus vector is cognate to a viral envelope protein of the particular enveloped virus. The particular enveloped virus may be any enveloped virus, including, but not limited to, a retrovirus, a herpesvirus, a rhabdovirus, human immunodeficiency virus (HIV), simian immunodeficiency virus (Sly), vesicular stomatitis virus, Rous sarcoma virus (RSV), murine leukemia virus (MLV), and the like. The cellular virus receptor protein may be selected from the group consisting of CD4, CCR5, CXCR4, ICAM-1, ICAM-2, ICAM-3, CR3, CR4, CD43, CD44, CD46, CD55, CD59, CD63, CD71, a chemokine receptor, Tva, and MCAT-1. The cellular virus receptor protein is preferably CD4, CCR5, CXCR4, Tva, or MCAT-1. As described herein, the enveloped virus may further comprise an additional component selected from the group consisting of a nucleic acid, an antisense nucleic acid, a gene, a protein, a peptide, Vpr protein, an enzyme, an intracellular antagonist of HIV, a radionucleotide, a cytotoxic compound, an antiviral agent, and an imaging agent.

In some instances, it is desirable to have an enveloped virus vector of the invention which comprises a plurality of cellular virus receptor proteins. For example, it may be desirable to target more than one type of cell, each different type of cell being susceptible to infection by a different enveloped virus. It may also be desirable to specifically target cells which express more than a one viral envelope protein on the surface thereof, or wherein more than one cellular virus receptor protein is necessary for attachment of an enveloped virus to and fusion of the envelope of the virus with the outer membrane of the cell. Or the proteins form a complex, quaternary structure (e.g. homo- or hetero-oligomers) that is useful for drug discovery targeting.

Thus, the enveloped virus vector of the invention includes, but is not limited to, an enveloped virus vector, as described herein, comprising a plurality of cellular virus receptor proteins. If a first cellular virus receptor protein is cognate to a first viral envelope protein and the second cellular virus receptor protein is cognate to a second viral envelope protein, then an enveloped virus vector comprising a first cellular virus receptor protein and a second cellular virus receptor protein may be used to target a cell which comprises the first viral envelope protein, a cell which comprises the second viral envelope protein, or both of these cells. The vector may also be used to target cells which comprise both the first viral envelope protein and the second viral envelope protein.

In one embodiment, each of the plurality of viral envelope proteins is a retroviral envelope protein. In another embodiment, each of the plurality of viral envelope proteins is a different viral envelope protein which is expressed by a single retrovirus, preferably HIV or SIV. In another embodiment, each of the plurality of cellular virus receptor proteins is selected from the group consisting of CD4, CCR5, CXCR4, ICAM-1, ICAM-2, ICAM-3, CR3, CR4, CD43, CD44, CD46, CD55, CD59, CD63, CD71, a chemokine receptor, Tva, and MCAT-1. In one aspect, the enveloped virus vector comprises CD4 and a chemokine receptor. In another aspect, the enveloped virus vector comprises CD4 and CCR5. In yet another aspect, the enveloped virus vector comprises CD4 and CXCR4. Other embodiments of the enveloped virus vector of the invention include, but are not limited to, those in which the enveloped virus vector further comprises a replication-deficient HIV-1 virion, preferably an NL-$R^-E^-$luc virion, and those in which the enveloped virus vector comprises an additional component selected from the group consisting of a nucleic acid, an antisense nucleic acid, a gene, a protein, a peptide, Vpr protein, an enzyme, an intracellular antagonist of HIV, a radionucleotide, a cytotoxic compound, an antiviral agent, and an imaging agent.

In another aspect, the enveloped virus vector/lipoparticle of the invention, comprises a membrane cellular protein of interest. Preferably, a lipoparticle comprises a multiple membrane spanning protein that spans the lipid bilayer at least twice. The skilled artisan would understand, based upon the disclosure provided herein, that the invention encompasses a wide plethora of such complex proteins which traverse a membrane multiple times. To date, methods to incorporate such complex membrane spanning peptides in a simple bilayer have not resulted in proteins where the function, structure, or both, of the peptide are maintained relative to the function and/or structure of the membrane protein in its natural state, e.g., in vivo. Further, the invention provides a novel system comprising a lipid bilayer where one or more such proteins can interact to form, e.g., homo and/or heterodimers, or otherwise interact with other membrane proteins or itself similarly to such interactions in the native membrane where the proteins typically reside.

The skilled artisan would appreciate, based upon the disclosure provided herein, that multiple membrane spanning protein include, but are not limited to, G-protein couple receptors (GPCRs) (also known as 7-transmembrane receptors, 7™) that span the membrane seven times, e.g., CCR5, CXCR4, CCR3, mu-opioid receptor, as well as transporters (proteins that transport molecules such as, but not limited to, amino acids or carbohydrates, across a membrane), ion channels, and the like. However, CD63, a multiple membrane spanning protein that has been previously identified to be present as, without wishing to be bound by any particular theory, a contaminant associated with a virus membrane, is not encompassed in the invention.

In another aspect, the invention includes a composition comprising a lipoparticle comprising a single membrane spanning protein. Membrane proteins that span the membrane once include, but are not limited to, CD4 (receptor for HIV and classic immunological modulator), neuropilin-1 (a VEGF receptor subtype), plexin-2 (involved in Rho/Rae signaling pathways), Tva (a receptor for Rous sarcoma virus, RSV, having homology to LDL-receptor), and the like. The lipoparticle is attached to a sensor surface, where a "sensor surface" is any substrate where a change in a property of the substrate mediated by the contacting of the surface with a molecule or compound is detected and can be compared to the surface in the absence of such contacting.

While the sensor surface can be a biosensor chip as exemplified herein, the sensor surface is not limited to such a chip. Instead, the skilled artisan would appreciate, based on the disclosure provided herein, that a sensor surface of the invention includes not only any biosensor chip that is disclosed herein (e.g., a Biacore C1 chip, a F1 chip, and the like), known in the art, or to be developed in the future. Such sensor surfaces include, but are not limited to, a glass substrate comprising a coating of e.g., gold, which can further comprise, for instance, a dextran matrix. However, the invention is not limited to any particular sensor surface. The important feature of such a surface is that a change in a characteristic of the sensor surface e.g., its refractive index, can be detected, preferably by an instrument connected to the sensor surface, such that data or information from the sensor can be assessed thus detecting the change, or lack of change, of the characteristic of the surface.

As noted elsewhere herein, the invention encompasses a lipoparticle comprising a variety of membrane proteins, including combinations of proteins, which can form complexes when present in the lipoparticle. Such complexes include, but are not limited to, complexes of proteins that function together, e.g., CD4 and CCR5, CD4 and CXCR4, and the like. The lipoparticle can comprise MCAT-1, an amino acid transporter that spans the membrane 14 times, and ion channels that span the membrane 6 times, e.g., K-channel KCNH2. All of these proteins have a similar feature: they span the membrane at least once. Many of these span the membrane multiple times. Proteins that span the membrane multiple times generally can not be removed from the lipid bilayer without destroying their structure. Anyone skilled in the art would understand that these proteins are difficult or impossible to isolate away from a lipid membrane while still retaining their structural integrity.

In addition, some complexes (e.g. homo and hetero-oligomers) interact only when in the lipid membrane and so retain their quaternary structure (formed by multiple subunits or proteins) only when in the lipid membrane. The lipoparticle of the invention encompasses incorporation of these proteins as well. In addition to these membrane proteins, which have been exemplified herein, other protein types and categories are encompassed in the invention and include, but are not limited to, the following: cytoplasmic domains of proteins (e.g., active conformations, G-protein coupling domains, kinase motifs of proteins such as EGF-receptor, and the like); intracellular proteins associated with an intracellular membrane (e.g., nuclear transporters, mitochondrial receptors, endoplasmic reticulum and Golgi membrane proteins); and multimeric complexes (e.g., dimers and trimers, viral envelope proteins, hetero-oligomers, and the like). More specifically, membrane proteins of the invention include, but are not limited to, GPCRs (e.g., CCR8, XCR1, CX3CR1), transporters (e.g., glucose transporter), ion channels (e.g., K-channel Kv1.3 tetramers), tetrameric Type II protein (e.g., DC-SIGN tetramers), constitutively active GPCRs (e.g., HHV8 ORF74), viral proteins (e.g., HIV gp160, hepatitis C E1-E2 Envelope protein, expressed on endoplasmic reticulum membrane).

Generation of the Enveloped Virus Vector of the Invention In essence, the method of making the enveloped virus vector/lipoparticle of the invention involves formation of a virus-like particle using a cell which comprises a cellular virus receptor protein. Hence, the method of making the enveloped virus vector of the invention requires expression of at least a competent portion of the genome of an enveloped virus in a cell which comprises a cellular virus receptor protein. The cellular virus receptor protein may be a normal component of the cell or it may be provided exogenously to the cell using, for example, known molecular biology techniques.

In one example of making the enveloped virus vector of the invention, at least a competent portion of the genome of an enveloped virus is provided to a producer cell which comprises a cellular virus receptor protein, and the producer cell is thereafter incubated under conditions which permit expression of the gene products encoded by the competent portion of the genome. These gene products include factors which facilitate packaging of the competent portion of the genome into a virus capsid-like particle, association of the capsid-like particle with the cell membrane, and budding of an enveloped virus-like particle comprising the cellular virus receptor protein from the cell, whereby the enveloped virus vector of the invention is thus generated.

In this example of making the enveloped virus vector of the invention, the identity of the producer cell which is used is not critical. However, the producer cell must comprise the cellular virus receptor protein or the cellular membrane protein of interest, and the competent portion of the genome must enable formation of virus-like particles when expressed in the producer cell.

The manner of providing the competent portion of the genome of the enveloped virus to the producer cell is also not critical. However, when the competent portion of the genome is expressed in the cell, the formation of at least one enveloped virus-like particle must be enabled. The competent portion of the genome may be provided in the form of, for example, the genome of an enveloped virus, a plasmid, or a non-circularized nucleic acid. The competent portion of the genome may be, but is not limited to, a single-stranded RNA molecule, a double-stranded RNA molecule, a single-stranded DNA molecule, a double-stranded DNA molecule, or an RNA-DNA hybrid molecule. The enveloped virus may be any enveloped virus, and is preferably a retrovirus. Preferred enveloped viruses are selected from the group consisting of HIV, Sly, RSV, and (ecotropic and amphotropic really refer to the Envelope protein of MLV, not the core) MLV.

Conditions which enable formation of the enveloped virus vector of the invention are well known in the art. These conditions may vary depending upon the properties of the producer cell and the enveloped virus used. A number of references exist which describe conditions which are useful for culturing particular enveloped viruses (*Fields Virology*, 3rd ed., Fields et al., eds., Lippincott-Raven Publishers, Philadelphia, Pa.). Particular non-limiting examples are provided herein of conditions which are useful to enable formation of the enveloped virus vector of the invention.

Conditions which enable formation of the enveloped virus vector of the invention include conditions which enable expression of the competent portion of the genome of the enveloped virus, conditions under which a cellular virus receptor protein is present in the membrane of the producer cell, and conditions which enable the formation of enveloped virus-like particles from the components of a producer cell which has been provided with the competent portion of the genome. Further details regarding processes by which enveloped viral particles are formed following provision to a cell of a competent portion of the genome of an enveloped virus have been described in the art, for instance by Wiley (1985, in *Virology*, Fields et al., ed., Raven Press, New York, 45-52).

Another example of making the enveloped virus vector of the invention, further comprises providing an additional component to the producer cell, Whereby, upon formation of the enveloped virus vector, the enveloped virus vector comprises the additional component. The additional component may be any molecule which can be provided to the cytoplasm or the membrane of the producer cell. By way of example, the additional component may be a nucleic acid, an antisense nucleic acid, a gene, a protein, a peptide, Vpr protein, an enzyme, an intracellular antagonist of HIV, a radionuclide, a cytotoxic compound, an antiviral agent, an imaging agent, or the like.

Inclusion of the additional component in the enveloped virus vector of the invention may be accomplished by directly coupling the additional component to the competent portion of the genome of the enveloped virus. For instance, if the competent portion of the genome is provided to the producer cell in the form of a plasmid, the plasmid may comprise a gene encoding an imaging agent, such as luciferase.

Inclusion of the additional component in the enveloped virus vector of the invention may also be accomplished by directly coupling the additional component to a nucleic acid encoding the cellular virus receptor protein. For example, if the cellular virus receptor protein is provided to the producer cell in the form of a DNA molecule encoding the same, an additional component comprising a protein may be provided to the producer cell by including the sequence of a gene encoding the protein in the DNA molecule, prior to provision thereof to the producer cell.

The additional component may also be provided directly to the membrane or the cytoplasm of the producer cell by, for example, including the additional component in the extracellular medium of the producer cell.

The producer cell need not normally comprise the desired cellular virus receptor protein or membrane protein of interest. Thus, in another example of making the enveloped virus vector of the invention, a producer cell is provided with at least a competent portion of the genome of an enveloped virus and a cellular virus receptor protein/membrane protein of interest, and is thereafter incubated under conditions which permit formation of an enveloped virus vector of the invention comprising the cellular virus receptor protein/membrane protein. This method, therefore, does not employ a producer cell which naturally comprises the cellular virus receptor protein or membrane protein of interest.

In this example of making the enveloped virus vector of the invention, the manner of providing the cellular virus receptor protein to the producer cell is not critical. By way of example, the cellular virus receptor protein may be provided to the producer cell in the form of a protein associated with the membrane portion of a membrane vesicle, a protein associated with a liposome, a protein associated with the membrane of a cell, a membrane-free solution of the protein, a solid protein, a protein associated with the envelope of an enveloped virus, a protein associated with the envelope of an enveloped virus vector of the invention, a nucleic acid, such as DNA or RNA, encoding the protein, a virus, which may be enveloped or non-enveloped, having a nucleic acid which encodes the protein, an enveloped virus vector having a nucleic acid which encodes the protein, or the like. Preferably, the cellular virus receptor protein is provided to the producer cell in the form of a DNA molecule encoding the protein, more preferably in the form of a plasmid. Methods for delivering proteins, membrane vesicles, liposomes, nucleic acids, and viruses to a cell are described in the literature. These methods may be easily adapted to the present situation.

The identity of the cellular virus receptor protein is not critical, except that it should be one which is cognate to a viral envelope protein which is displayed on the surface of a cell with which it is desired to fuse the enveloped virus vector, where applicable. The cellular virus receptor protein may be any protein which is cognate to a viral envelope protein. Preferably, the cellular virus receptor protein is cognate to a retroviral envelope protein, more preferably, it is cognate to a viral envelope protein of a virus selected from the group consisting of HIV, SIV, RSV, and ecotropic MLV. Also preferably, the cellular virus receptor protein is selected from the group consisting of CD4, CCR5, CXCR4, ICAM-1, ICAM-2, ICAM-3, CR3, CR4, CD43, CD44, CD46, CD55, CD59, CD63, CD71, a chemokine receptor, Tva, and MCAT-1. More preferably, the first virus receptor protein is selected from the group consisting of CD4, CCR5, CXCR4, Tva, and MCAT-1.

A plurality of cellular virus receptor proteins may be provided to the producer cell in the same manner as that in which a single cellular virus receptor protein is provided. When more than one cellular virus receptor protein are provided to the producer cell, it is preferred that one is CD4 and another is a chemokine receptor. More preferably, one is CD4 and another is CCR5 or CXCR4.

Further, in addition to the aforementioned proteins, the invention encompasses embedding any protein of interest in the lipoparticles of the invention. Not only can the lipoparticles comprise a chemokine coreceptor, e.g., CCR5, CXCR4, CD4, neuropilin, or MCAT-1, or other membrane protein, but the invention includes lipoparticles comprising any protein of interest, preferably a membrane component, that interacts with another protein. Such proteins include, but are not limited to, any of the G-protein coupled receptors (GCPRs), a transporter, an ion channel, a type I membrane protein, a type II membrane protein, and the like.

The skilled artisan would appreciate, based upon the disclosure provided herein, that the lipoparticle comprises a multiple membrane spanning protein which is not CD63. Moreover, the invention further includes a composition comprising a lipoparticle comprising a protein that spans a membrane at least once, where the lipoparticle is attached to a sensor surface. Such composition thus includes a protein spanning the membrane at least and can comprise various proteins some spanning the membrane once while other span the membrane at least twice. Such proteins can interact to form complexes or otherwise interact while present in the lipoparticle lipid bilayer.

In addition to a lipoparticle comprising a virus core, the present invention includes a lipoparticle comprising a bead core, also referred to as a proteoliposome, where the lipoparticle is attached to a sensor surface. A proteoliposome, as the term is used herein, comprises a synthetic bead, e.g., plastic, surrounded by a membrane as described by Mirzabekov et, al. Thus, the present invention is not limited to virus-based lipoparticles, but includes such lipoparticles as proteoliposomes.

The lipoparticle can comprise non-membrane proteins. More particularly, a lipoparticle can comprise water soluble proteins that interact with a membrane receptor of interest. For example, a lipoparticle comprising a GCPR can be made with or without G-proteins, the intracellular subunits (alpha, beta, gamma) that couple to the receptor and mediate signaling. These intracellular proteins can influence extracellular protein structure and can be important for formation of lipoparticles comprising complex membrane proteins that interact with soluble intracellular proteins.

Use of the Enveloped Virus Vector of the Invention
Targeted Vector

The enveloped virus vector of the invention may be used to deliver a composition to a target cell. This composition delivery method is particularly useful when it is desired to deliver a composition specifically to a cell which comprises a viral envelope protein on its surface. Specific examples of such a target cell include, but are not limited to, a cell infected with an enveloped virus, such as HIV, SIV, RSV, or ecotropic MLV. A target cell may also be a cell infected with another enveloped virus vector of the invention or a cell which has fused with an enveloped virus vector other than the enveloped virus vector of the invention.

The composition to be delivered to the target cell by the enveloped virus vector of the invention may be any composition which may be associated with the enveloped virus vector before, during, or after generation of the enveloped virus vector. Examples of such compositions include, but are not limited to, a nucleic acid, an antisense nucleic acid, a gene, a protein, a peptide, Vpr protein, an enzyme, an intracellular antagonist of HIV, a radionuclide, a cytotoxic compound, an antiviral agent, an imaging agent, and the like. The composition may be associated with the enveloped virus vector by generating the vector in a producer cell which comprises the composition, whereby, upon budding of the enveloped virus vector of the invention from the producer cell, the enveloped virus vector comprises the composition. The composition may also be associated with the enveloped virus vector by treating the vector with the composition after the vector has been made. Methods of associating a composition with an enveloped virus vector include electroporation, specific adhesion of the composition to a component of the enveloped virus vector such as an envelope protein thereof, and other methods known to one skilled in the art.

A particularly useful method of using the enveloped virus vector of the invention relates to delivering a composition to a human cell infected with HIV. Preferably, the HIV is HIV-1. Also preferably, the composition is a cytotoxic compound or an antiviral agent. The enveloped virus vector which is useful in this method comprises CD4, a cellular virus receptor protein for HIV-1, and either CCR5 or CXCR4, two other cellular virus receptor proteins for HIV-1. The composition may be, but is not limited to, an known anti-HIV agent, such as AZT, ddC, ddI, an HIV protease inhibitor, a cytotoxic agent, an enzyme, or a gene encoding an enzyme capable of activating small molecules in a cell, which activated small molecules are useful as cytotoxic or antiviral agents. Such enzymes include, but are not limited to, herpesvirus thymidine kinase, which is capable of phosphorylating gancyclovir, thereby generating phosphorylated gancyclovir which is a cytotoxic agent. Hence, the enveloped virus vector comprising the composition, e.g. gene encoding an enzyme, CD4, and either of CCR5 or CXCR4 specifically delivers the composition to human cells which are infected with HIV-1 and may thereby kill the cell or prevent virus replication in that cell. Any number of other potential antiviral or cytotoxic agents which have been described in the literature may be so delivered using the enveloped virus vector of the invention.

The enveloped virus vector useful for delivering a composition to a target cell may comprise a single cellular virus receptor protein or a plurality of cellular virus receptor proteins. By way of example, the enveloped virus vector may comprise a cellular virus receptor protein selected from the group consisting of CD4, CCR5, CXCR4, ICAM-1, ICAM-2, ICAM-3, CR3, CR4, CD43, CD44, CD46, CD55, CD59, CD63, CD71, a chemokine receptor, Tva, and MCAT-1. In preferred embodiments, the enveloped virus vector comprises Tva, MCAT-1, CD4, CCR5, CXCR4, both CD4 and CCR5, or both CD4 and CXCR4. However, the invention is not limited to these molecules. Indeed, the data disclosed herein demonstrating the successful incorporation of MCAT-1 into MLV (murine leukemia virus) lipoparticles, demonstrate that type 1 (i.e., single-spanning proteins), and not just multiple membrane spanning proteins such as GCPRs, can be embedded in the lipoparticles while preserving their native binding ability. Preservation of binding ability relative to the protein as typically present in the cell membrane can be assessed by functional assays, such as, but not limited to, the fusion assays disclosed herein, and also by using biosensor assays such as those exemplified herein.

The enveloped virus vector of the invention may be used to expand the host range or tissue tropism of an enveloped virus or vector. The host range and tissue tropism of an enveloped virus or vector is determined in part by the protein composition of the envelope surrounding the virus or vector. Thus, the enveloped virus vector may be used to provide a protein or another component to a target cell prior to production of another enveloped virus or vector using the same target cell. By way of example, a first enveloped virus vector may be used to provide a cellular protein to a cell. When a second enveloped virus vector or enveloped virus subsequently enters the cell, the cellular protein becomes a component of the second enveloped virus vector or the enveloped virus upon replication of the same within the cell. The cellular protein may be one which alters the tissue tropism of the second vector or virus thereby expanding the host range of that second vector or virus.

To alter the host range or tissue tropism of an enveloped virus or vector, a target cell is contacted with the enveloped virus vector of the invention, the envelope of which comprises a tropism determinant, preferably a cellular virus receptor protein or a viral envelope protein, wherein the enveloped virus or vector is capable of fusing with the target cell. Following fusion of the enveloped virus vector and the target cell, the membrane of the target cell comprises the tropism determinant provided by the enveloped virus vector of the invention. Subsequent use of the target cell to produce the enveloped virus or vector results in the inclusion of the tropism determinant in the envelope of the enveloped virus or vector, thereby altering the tissue tropism of the enveloped virus or vector.

Figure 7:
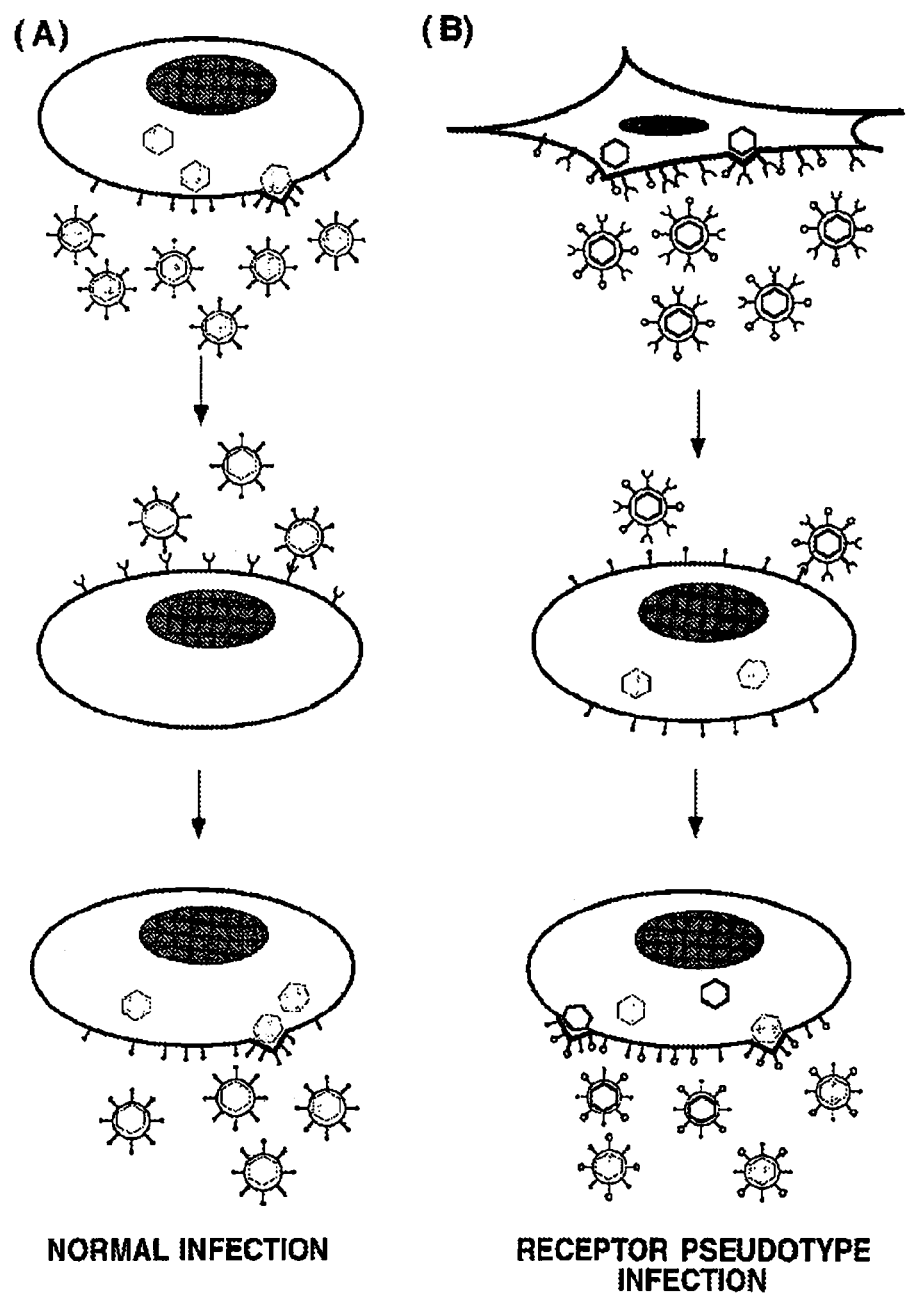
FIG. 7, comprising Panels A and B, is a pair of diagrams which depict infection of cells by enveloped viruses and assembly and budding of enveloped viruses. In Panel A, a normal cycle of cellular infection is depicted. In Panel B, a means of altering the tropism of an enveloped virus is depicted.

An aspect of the invention is illustrated in FIG. 7. The diagram in FIG. 7, Panel A, depicts normal infection of a cell (ellipse enclosing a filled ellipse) by enveloped viruses having envelopes (circles enclosing shaded hexagons) which comprise viral envelope proteins (lines extending from viral envelopes and each having a filled circle at the distal end thereof). In the upper image, virions assemble, bud from the cell, and incorporate viral envelope proteins into the envelope of the virion. In the center image, virions infect target cells that express a cellular virus receptor protein (lines extending from cell and each having a hemicircle at the distal end thereof). In the lower image, virions assemble, bud from the cell, and incorporate viral envelope glycoproteins into the envelope of the virion.

The diagram in FIG. 7, Panel B, depicts a method of altering the tropism of an enveloped virus. In the upper image, enveloped virus vectors (circles enclosing unshaded hexagons) assemble, bud from the first cell (irregular shaped body enclosing a filled ellipse), and incorporate into their envelopes both a first viral envelope protein (lines extending from viral envelopes and each having an open circle at the distal end thereof) and cellular virus receptor proteins (lines extending from the first cell and each having a hemicircle at the distal end thereof) cognate to a second viral envelope protein. In the center image, the enveloped virus vectors are capable of infecting a second cell (ellipse enclosing a filled ellipse) which is itself infected by an enveloped virus (circles enclosing shaded hexagons). The second cell express the second viral envelope protein (lines extending from the second cell and each having a filled circle at the distal end thereof) and the cellular virus receptor protein is capable of binding to these second viral envelope proteins. In the lower image, following infection of the second cell by enveloped virus vectors, altered enveloped viruses are assembled, bud from the second cell, and incorporate into their envelopes both the first viral envelope protein and the second viral envelope protein. Thus, the tropism of the altered enveloped virus differs from that of the original enveloped virus.

By way of example, the host range of an enveloped murine cytotoxic virus which is normally not capable of infecting any type of human cells may be altered such that the virus is capable of infecting HIV-infected human cells. To alter the cytotoxic virus, a target cell such as a murine T-cell which the cytotoxic virus is normally capable of infecting, is contacted with the enveloped virus vector of the invention. This enveloped virus vector comprises the cellular virus receptor proteins CD4 and CXCR4, and a viral envelope protein to which a cellular virus receptor protein of the target cell is cognate, wherein the enveloped virus vector is capable of fusing with the target cell. Following fusion, the target cell membrane comprises CD4 and CXCR4. Subsequent infection of the target cell by the murine virus and replication of the virus therein results in the production of a pseudotyped cytotoxic virus particle having CD4 and CXCR4. Infection of a human infected with HIV-1 with a pseudotyped cytotoxic virus comprising CD4 and CXCR4 results in death of HIV-1-infected human cells. Human cells which are not infected with HIV-1 are not killed, because they cannot be infected with the altered cytotoxic virus.

Other properties of an enveloped virus or virus vector having an envelope may be altered by including one or more additional components in the enveloped virus vector of the invention. Fusion of the enveloped virus vector with a target cell provides the additional component to the target cell. Subsequent use of the target cell to produce an enveloped virus or vector results in the inclusion of the additional component in the virus or vector. The selection of the additional component is dependent upon the alteration which is desired. Numerous components may be selected which are known in the art to affect a property of a virus in a desired manner. By way of example, the additional component may be selected from the group consisting of a nucleic acid, an antisense nucleic acid, a gene, a protein, a peptide, Vpr protein, an enzyme, an intracellular antagonist of HIV, a radionuclide, a cytotoxic compound, an antiviral agent, an imaging agent, and the like.

The enveloped virus vector of the invention may be used to render a cell susceptible to fusion with an enveloped virus or vector, wherein the cell is not normally susceptible to such fusion. Thus, it is possible to generate a non-human animal model of a viral disease of humans and to enable staged delivery of enveloped viral vectors to a human cell.

A non-human animal model of a human disease may be made by contacting a cell of the non-human animal with an enveloped virus vector comprising a cellular virus receptor protein which is cognate to a viral envelope protein of a human pathogenic enveloped virus, wherein the enveloped virus vector is capable of fusing with the cell of the nonhuman animal. Fusion of the vector and the cell provides the cell with the cellular virus receptor protein, whereby the cell becomes susceptible to infection by the human pathogenic enveloped virus. The non-human animal cell which becomes susceptible to infection by the human pathogenic enveloped virus may be used both in vitro or in vivo to investigate the disease mediated by the pathogenic virus without exposing a human subject to the virus.

By way of example, a murine model of HIV-1 infection may be generated by contacting a murine T-cell with an enveloped virus vector which comprises a viral envelope protein to which a murine cellular virus receptor protein normally found on the surface of the murine T-cell is cognate and a cellular virus receptor protein which is cognate to a viral envelope protein of HIV-1. By virtue of the interaction between the murine cellular virus receptor protein and the viral envelope protein of the vector, the vector is capable of fusing with the cell and thereby provides to the cell the cellular virus receptor protein which is cognate to a viral envelope protein of HIV-1. As a result, the murine T-cell is rendered susceptible to infection by HIV-1.

In a preferred method, the enveloped virus vector comprises a plurality of cellular virus receptor proteins, each of which is cognate to a viral envelope protein of HIV. For example, an enveloped virus vector comprising CD4 and a chemokine receptor such as, but not limited to, CCR5 and CXCR4, may be used.

Alternately, an analogous method may be used to render a non-human cell susceptible to infection by a non-human virus which is similar to a human pathogenic virus. The alternate method substitutes the non-human virus in place of the human pathogenic enveloped virus referred to herein. By way of example, a cell of a non-human animal may be rendered susceptible to infection by SIV, which is similar to HIV, using the methods described herein.

The enveloped virus vector of the invention may comprise both a cellular virus receptor protein and a viral envelope protein. Hence, the vector may be used to enable staged delivery of enveloped viral vectors to a cell. By way of example of such staged delivery, a single cell in a population of cells may be fused in a first stage with a first enveloped virus vector which comprises a first viral envelope protein and a first cellular virus receptor protein. Later, in a second stage, a second enveloped virus vector may be provided to the population of cells, which second vector comprises a second cellular virus receptor protein which is cognate to the first viral envelope protein, whereby the single cell fuses with the second enveloped virus vector, while the remainder of the cells in the population do not. Likewise, the second enveloped virus vector may further comprise a second viral envelope protein, and a third enveloped, virus vector comprising a third cellular virus receptor protein which is cognate to the second viral envelope protein may be fused with the single cell in a third stage. There is no theoretical limit to the number of such stages which may be performed using the methods described herein.

Staged delivery of enveloped virus vectors to a cell has numerous uses including, but not limited to, staged delivery of therapeutic agents wherein agents having relatively low toxicity are delivered in early stages while agents having greater toxicity are delivered in later stages to cells which were not suitably treated in the early stages. In addition, delivery of a gene to a cell may be accomplished wherein expression of the gene in the cell is desired for only a limited, period of time. The gene may be delivered to the cell in a first stage using an enveloped virus vector of the invention, and an agent which halts gene expression or which kills the cell to which the gene was delivered in the first stage may be delivered in a later stage using a second enveloped virus of the invention.

The enveloped virus vector of the invention may also be used to produce a cellular virus receptor protein to obtain quantities of the protein which can be easily purified, relative to purification of the protein from the physiological cellular source of the protein. To accomplish this, the enveloped virus vector of the invention is generated using any of the methods described herein. By separating the enveloped virus vector, which includes the cellular virus receptor protein, from the cells used to make or propagate the vector, the cellular virus receptor protein is obtained. Furthermore, because virus propagation may be performed on a large scale, propagation of the enveloped virus vector of the invention may be used to produce a large quantity of the cellular virus receptor protein. The vector may subsequently be separated from the producer cell, whereby a large quantity of the cellular virus receptor protein may be biochemically purified from the enveloped virus vector using ordinary biochemical and immunological technology to yield pure or substantially pure protein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As used herein, the term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

Study of Protein Interaction

The enveloped virus vector of the invention may also be used to ascertain whether a test protein is a viral envelope protein to which a particular cellular virus receptor protein is cognate. To accomplish this, a test cell is provided, comprising a control cell having the test protein in the outer membrane thereof. An enveloped virus vector is also provided, wherein the vector comprises the desired cellular virus receptor protein. The enveloped virus vector is contacted with the test cell, and the ability of the enveloped virus vector to fuse with the test cell is assessed. The ability of the enveloped virus vector to fuse with the test cell is an indication that the test protein is a viral envelope protein to which the certain cellular virus receptor protein is cognate.

The test protein may be provided to the test cell by infecting the test cell with an enveloped virus which comprises the test protein, by providing to the test cell a nucleic acid which encodes the test protein and which is capable of expression in the test cell, or by any other method known to one of skill in the art of molecular biology.

The test protein may be any protein. Preferably, the test protein is a membrane protein, more preferably a membrane protein present in the membrane of a cell infected with an enveloped virus. The test protein may also be a protein naturally present in the envelope of an enveloped virus.

The ability of the enveloped virus vector to fuse with the test cell may be assessed in any manner known to one of skill in the art. For example, immunological methods are well known in the art of detecting viral infection of a cell. Preferably, the enveloped virus vector further comprises an additional component, the presence of which component in the test cell may be easily determined. Non-limiting examples of such additional components include luciferase protein, a gene encoding luciferase protein, a radionuclide, and an imaging agent.

Indeed, protein-protein interaction can be assessed using methods of such interaction that do not require cell fusion as an indication of protein-protein interaction. As exemplified herein, such methods include, but are not limited to, contacting a virus lipoparticle comprising a test protein with a second protein, e.g., a potential ligand or a known ligand the interaction of which is being assessed or inhibited, and assessing the interaction between the two proteins. The skilled artisan would appreciate, based upon the disclosure provided herein, that the ligand, or potential ligand, can be any protein, membrane or otherwise, and that the ligand is also not limited to any particular protein. Thus, the ligand, or potential ligand, the lipoparticle is contacted with, i.e., the ligand, can include, among other proteins, the same protein, that is present on the lipoparticle, an antibody, a peptide, or a chemical compound that is not comprised of amino acids, such as, but not limited to, a carbohydrate, a lectin, a chemical low molecular weight substance. Such ligand encompasses those described in Doranz et al., 1997, J. Exp. Med. 186: 1395-1400.)

The term "ligand," as used herein, encompasses any protein or compound that can bind with a protein present in a lipoparticle. The ligand encompasses a protein or non-protein compound that can bind with a protein present in a lipoparticle.

"Lipoparticle," as used herein, means a small particle of about one nanometer to about a micrometer in size, comprising an external lipid bilayer further comprising a protein. The core, or interior, of the lipoparticle is not a crucial feature of the invention. Lipoparticles of the invention include, but are not limited to, a virus, e.g., a retrovirus (e.g., HIV, MIX, RSV, VSV, and the like), a vesicular stomatitis virus, and the like), a membrane-enveloped virus, and a proteoliposome (i.e., a lipid bilayer formed around a bead where the bilayer comprises a protein of interest). The protein-protein interaction can be assessed using any method either known in the art or to be developed for assessing protein-protein interaction. Such methods include, but are not limited to, using a microfluidic device. Preferably, the microfluidic device comprises a microchannel and/or a microwell.

Microfluidics is the miniaturization of biological separation and assay techniques to such a degree that multiple experiments can be accomplished on a miniature scale. Tiny quantities of solvent, sample, and reagents, typically in the micrometer or nanoliter range, are steered through narrow (typically micron scale) channels on the chip or placed within miniature wells, where they are mixed and analyzed by such techniques as electrophoresis, fluorescence detection, immunoassay, or indeed almost any classical laboratory method (Nature Biotechnology, "Microfluidics—downsizing large-scale biology," August 2001).

More preferably, the microfluidic device is a biosensor device. [Biosensor devices are designed to measure the interaction between biological molecules. Typically, biosensors measure direct interactions between a protein of interest and potential ligands (proteins, antibodies, peptides, small molecules) that may bind to it. Biosensors are typically highly sensitive and can work with and detect even very weak or very small quantity interactions. Biosensor devices have been constructed that consist of optical chips, fiber optics, spectrometer detectors, microchannel chips, nanowells, and microcantilevers. Even more preferably, the assay comprises using a biosensor device wherein the device is a surface plasmon resonance biosensor device.

The most commonly used optical biosensors (Biacore™) are based on surface plasmon resonance (SPR) that measures changes in refractive index at the sensor surface (see, e.g., Canziani et al., 1999, Methods. 19:253-269; Rich and Myszka, 2000, Curr. Opin. Biotechnol, 11:54-61.) Biacore's biosensor system measures interactions between the immobilized molecules on the surface of sensor chips and the molecules contained in a solution that passes over the surface under controlled flow conditions. The Biacore biosensor chip comprises a glass surface, coated with a thin layer of gold that provides the physical conditions required for SPR, which is the basis by which changes in mass, and therefore binding, on the sensor chip surface is detected. Gold-dextran sensor chips are further comprised of a dextran layer which covers the gold and is specifically designed to minimize non-specific binding and provide a favorable environment for interactions between biomolecules. SPR chips use microfluidic channels to deliver the sample on the chip in precise quantities and at precise times.

Optical detection technology with SPR measures changes in mass on the sensor chip surface (i.e. binding), with a sensitivity of less than a picogram. SPR biosensors are unique in their ability to quantify binding in real-time, thereby producing the following four data sets: 1) specificity of binding, 2) concentration, 3) kinetics (association and dissociation rates), and 4) affinity. Briefly, as exemplified elsewhere herein, the lipoparticle comprising a test protein is affixed onto a surface or solid support or substrate. The second protein is allowed to contact the lipoparticle and the interaction, if any, between the test protein and the second protein, which may be the same protein where homologous protein interaction is being assessed, is characterized using an instrument.

One skilled in the art would appreciate, based upon the disclosure provided herein, that the nature of the instrument, or the particular surface to which the lipoparticle is attached, are not crucial. That is, while a derivatized gold surface or a short carboxy detran matrix can be used to attach the lipoparticle thereto, the invention is in no way limited to these surfaces; instead, the invention includes any surface that can be used in a microfluidic device to assess the interaction of proteins. Such substrates include, but are not limited to, a wide plethora of biosensor "chips" that are commercially available, and others surfaces that are known in the art, or such surfaces as will be developed in the future.

Biosensor surfaces for other biosensor and microfluidic devices are composed of quartz glass (e.g. Caliper's Lab-Chips), Acrylic (Aclara's microfluidic chips), plastic (Gyros' compact disc microfluidics), plastic wells (Evotec's nanowells and Signature Bioscience's spectroscopy platform are relatively surface independent so standard 96-well plates made of polystyrene or polypropylene can be used), silver (CPWR biosensors use a silver instead of a gold surface), silicon (Protiveris' microcantilevers are composed of silicon), or glass fiber (Illumina's optical fiber biosensors). Each of these surfaces can, in turn, be modified for better coupling, lower background, increased signal, etc. Modifications of the biochip surface include attachment of dextran, PEGylation, coating with BSA, etc.

One instrument useful for assessing molecule interactions, e.g., an optical biosensor, can be used to detect any change in the refractive index at a sensor surface under various conditions. This allows the detection of interactions between molecules as detected by changes in the refractive index at the sensor surface. The change in the surface resonance indicates the interaction between binding partners, at least one of which is tethered, or otherwise attached, to the surface of the sensor. More particularly, one molecule is tethered, the other is flowed over through microchannel. If the flowed molecule attaches to the tethered molecule, a signal is detected.

Methods of attaching a lipoparticle to a sensor surface are well known in the art and are exemplified elsewhere herein. Moreover, the invention encompasses methods of attaching, including tethering, a lipoparticle to a surface for measuring interaction of a protein present in the lipoparticle with another protein. Such methods include, but are not limited to, activation of amino acid carboxyl groups, and the like. Other attachment technologies are also encompassed in the invention including a Biacore a class of chips, all designed to capture the protein of interest (in this instance, the entire lipoparticle) differently. One chip, the L1 chip, acts differently from the other commercially available chips in that it is hydrophobic so is designed to capture lipid vesicles by attracting the lipid to the chip surface and then "melting" lipid vesicles onto the chip surface so that the end result is that the L1 chip surface is covered by a bilayer of lipid with the protein of interest embedded in the bilayer. Such chips, and others known in the art or to be developed in the future, are included in the present invention.

The conditions used in the assay to assess protein interaction with a ligand are not a limiting factor. That is, a wide plethora of conditions for use in assays of binding interactions are known in the art and are not repeated herein. Further, the invention encompasses any assay conditions developed in the future. Preferably, the pH for attachment of the lipoparticle to a sensor surface is about 5.5. The skilled artisan would appreciate, based upon the disclosure provided herein, that the pH for attachment depends on the method of attachment used, and can be from about pH 4 to 10. The number of RU captured is proportional to the number of RU signal that is obtained, which is, in essence, the sensitivity and signal:noise specificity of detection of the assay. Typically, the procedures exemplified herein captured thousands (e.g. 2000-6000) of RU lipoparticle and obtained a signal of several hundred RU.

Preferably, the bound lipoparticle can withstand at least one regeneration cycle where bound ligands/analytes are removed without damaging the lipoparticles or the protein that they comprise. Regeneration conditions are well known in the art, or are disclosed herein. However, the invention is in no way limited to these or any other regeneration parameters, but encompasses any regeneration regimen known in the art or to be developed in the future, including, but not limited to, a brief pulse using a regeneration mixture comprising about equal parts of a pH 5 and a chaotropic solution.

The skilled artisan would understand, based upon the disclosure provided herein, that the invention can encompass a lipoparticle formed around a bead, e.g., a proteoliposome. Such lipoparticle/bead constructs are well known in the art and methods for the production of such constructs is set forth in, for instance, Mirzabekov et al. (2000, Nature Biotechnology 18: 649-654), and Babcock et al. (2001, *J. Biol. Chem.*) Briefly, proteoliposomes consist of nano- or micrometer sized beads that are surrounded by a lipid membrane bilayer that is embedded with membrane-bound receptors. To form proteoliposomes, the surface of nonporous magnetic beads is covalently conjugated with an antibody that recognizes a C-terminal epitope tag (e.g. FLAG) on the receptor of interest. The beads are used to capture detergent-solubilized receptor (expressed at high levels in a cell line), washed, and then mixed with detergent-solubilized lipid. During the removal of detergent by dialysis, the lipid bilayer membrane self-assembles around the beads and the receptor is returned to its native environment. Proteoliposomes are uniform in size, stable in a broad range of harsh conditions (high or low pH, extremes of ionic strength, ranges of temperature, 0-50° C.), and can be used in FACS and competition assays typically applied to cells. By using magnetic beads, proteoliposomes can be easily isolated and purified.

It was previously demonstrated that complex membrane-bound receptors (the GPCRs CCR5 and CXCR4) can be incorporated into proteoliposomes (e.g., Nature Biotechnology (2000) and J. Biol. Chem. (2001)). These proteoliposomes were used to select CCR5-specific antibodies from a recombinant phage display library and for binding to antibodies and proteins. The skilled artisan would appreciate, based upon the disclosure provided herein, that such proteoliposomes, comprising a membrane protein, can be attached to a sensor surface.

In a variation of this method, the test cell and a control cell are each contacted with the enveloped virus vector. The ability of the enveloped virus vector to fuse with the test cell is assessed, and the ability of the enveloped virus vector to fuse with the control cell is assessed. A greater ability of the enveloped virus vector to fuse with the test cell compared with the ability of the enveloped virus vector to fuse with the second control cell is an indication that the test protein is a viral envelope protein to which the particular cellular virus receptor protein is cognate.

In another variation of this method, a library comprising a plurality of nucleic acid-containing vectors is provided, each of which comprises a nucleic acid which corresponds to at least a portion of a viral nucleic acid, wherein when a vector selected from the library is provided to a control cell, any protein encoded by the nucleic acid of that vector is capable of expression in the control cell. Methods of making such vectors are well known to one skilled in the art of molecular biology and are described in such references as Sambrook et al. (1989, *Molecular Cloning: A Laboratory Manual*, Cold Spring Harbor Laboratory, New York). An individual vector is provided to a control cell and is expressed therein to generate a test cell. An enveloped virus vector comprising the particular cellular virus receptor protein is contacted with the test cell. If the nucleic acid encodes a viral envelope protein to which the particular cellular virus receptor protein is cognate, then the test cell is susceptible to fusion with the enveloped virus vector. The ability of the enveloped virus vector to fuse with the test cell thus indicates that the nucleic acid of the vector encodes a viral envelope protein to which the particular cellular virus receptor protein is cognate. The nucleic acid of the vector may subsequently be isolated, cloned, and characterized using techniques well known in the art.

The enveloped virus vector of the invention may further be used to ascertain whether a test protein is a cellular virus receptor protein which is cognate to a particular viral envelope protein. A test cell is provided, comprising a control cell having the particular viral envelope protein in the outer membrane. An enveloped virus vector is also provided, wherein the vector comprises the test protein in the envelope. The enveloped virus vector is contacted with the test cell, and the ability of the enveloped virus vector to fuse with the test cell is assessed. The ability of the enveloped virus vector to fuse with the test cell is an indication that the test protein is a cellular virus receptor protein which is cognate to the particular viral envelope protein.

The viral envelope protein may be provided to the test cell by infecting the test cell with an enveloped virus which comprises the particular viral envelope protein, by providing to the test cell a nucleic acid which encodes the particular viral envelope protein and which is capable of expression in the test cell, or by any other method known to one of skill in the art of molecular biology.

The enveloped virus vector may be made by any of the methods described herein for making an enveloped virus vector of the invention, by substituting the test protein in place of the cellular virus receptor protein or by substituting a nucleic acid encoding the test protein in place of the nucleic acid encoding the cellular virus receptor protein, as appropriate.

The test protein may be any protein. Preferably, the test protein is a membrane protein, more preferably a membrane protein present in the membrane of a cell susceptible to infection by an enveloped virus. The test protein may also be a protein present in the envelope of an enveloped virus or in a virus vector having a membrane envelope. More preferably a membrane protein that spans the membrane multiple times. Most preferably any receptor found on the surface of a cell or on the surface of intracellular organelles or intracellular membranes.

The ability of the enveloped virus vector to fuse with the test cell may be assessed in any manner known to one of skill in the art, as described herein.

In a variation of this method, the test cell and a control cell are each contacted with the enveloped virus vector. The ability of the enveloped virus vector to fuse with the test cell is assessed. The ability of the enveloped virus vector to fuse with the control cell is assessed. A greater ability of the enveloped virus vector to fuse with the test cell, compared with the ability of the enveloped virus vector to fuse with the second control cell, is an indication that the test protein is a cellular virus receptor protein which is cognate to the particular viral envelope protein.

In another variation of this method, a library comprising a plurality of recombinant enveloped virus vectors is provided, each of which vectors comprises a nucleic acid which corresponds to at least a portion of a cellular nucleic acid. When a producer cell is fused with a recombinant enveloped virus vector of the library, the nucleic acid is capable of expression in the producer cell. Methods of making such recombinant enveloped virus vectors are well known to one skilled in the art of molecular biology and are described in such references as Sambrook et al. (1989, *Molecular Cloning: A Laboratory Manual*, Cold Spring Harbor Laboratory, New York). An individual vector is fused with a producer cell in which the vector is capable of replication and the portion of the cellular nucleic acid is expressed, yielding a progeny vector. Thus, if the nucleic acid encodes a cellular virus receptor protein, the progeny vector comprises the cellular virus receptor protein in its envelope. An individual progeny vector is contacted with the test cell comprising the particular viral envelope protein, and the ability of the progeny vector to fuse with the test cell is assessed. The ability of the progeny vector to fuse with the test cell indicates that the cellular nucleic acid encodes a cellular virus receptor protein which is cognate to the particular viral envelope protein. The cellular nucleic acid which the progeny vector comprises may be isolated, cloned, and characterized using methods well known in the art.

By way of example, a test cell comprising EnvA, the viral envelope protein of RSV(A), may be used to identify whether a test protein is a cellular virus receptor protein which is cognate to EnvA. To accomplish this, a cellular genome obtained from a cell which is susceptible to infection by RSV(A) is cleaved to form cellular nucleic acids. Individual cellular nucleic acids are inserted into an enveloped virus vector of the invention which is capable of fusing with and replicating within a producer cell which is not susceptible to infection by RSV(A). The vector comprising the cellular nucleic acid is fused with a producer cell and replicated therein, yielding a progeny vector. The cellular nucleic acid, delivered to the producer cell via fusion with the vector, is expressed by the producer cell, whereby any membrane protein encoded by the cellular nucleic acid will be present in the envelope of the progeny vector. The progeny vector is contacted with the test cell, and the ability of the progeny vector to fuse with the test cell is an indication that the cellular nucleic acid encodes a cellular virus receptor protein which is cognate to EnvA.

The enveloped virus vector of the invention may be used to investigate the ability of a composition to affect the interaction between a viral envelope protein and a cellular virus receptor protein which is cognate to the viral envelope protein. To accomplish this, a cell is provided which comprises the viral envelope protein. An enveloped virus vector comprising a cellular virus receptor protein which is cognate to the viral envelope protein is contacted with the cell in the presence or absence of the composition, and the ability of the enveloped virus vector to fuse with the cell is assessed. A greater or lesser ability of the enveloped virus vector to fuse with the cell in the presence of the composition, relative to the ability of the enveloped virus vector to fuse with the cell in the absence of the composition, is an indication that the composition is capable of affecting the ability of the viral envelope protein and the cellular virus receptor protein to interact.

The cell may be prepared by infecting cells with a virus comprising the viral envelope protein, by providing the cell with a nucleic acid which encodes the viral envelope protein and which is capable of being expressed in the cell, or by any other method known to one of skill in the art of membrane protein biochemistry.

The enveloped virus vector may be prepared using any of the methods described herein. Preferably, the enveloped virus vector further comprises an additional component, the presence of which component in the cell may be easily determined. Non-limiting examples of such additional components include luciferase protein, a gene encoding luciferase protein, a radionuclide, and an imaging agent.

One skilled in the art would appreciate, based on the disclosure provided herein, that the lipoparticle can comprise any membrane protein, i.e., any protein that typically is associated with a membrane. Preferably, the lipoparticle comprises a multiple membrane spanning protein. That is, the protein spans the membrane at least twice. Such multiple membrane spanning proteins encompass a wide plethora of membrane proteins including, but not limited to, the 7 transmembrane receptor proteins (e.g., G-protein coupled receptor proteins, GPCRs, which include chemokine coreceptors), ion channels, transporters (such as amino acid transporter MCAT-1 and glucose transporter, and the like).

Further, one skilled in the art would understand, based upon the disclosure provided herein, that the invention includes a composition comprising a lipoparticle attached to a sensor surface further wherein the liposome comprises a membrane spanning protein. The membrane spanning protein encompasses any protein that spans the membrane at least once. The skilled artisan would appreciate, based upon the disclosure provided herein, that the lipoparticle of the invention can encompass a multiple membrane spanning protein that spans the membrane at least twice and is not CD63, and, when the lipoparticle is attached to a sensor surface, it can further comprise a membrane spanning protein that spans at least once.

Kits

The invention includes various kits which comprise a lipoparticle comprising a multiple membrane spanning protein, and/or compositions of the invention, an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for assessing the binding interaction of a membrane spanning protein with a ligand. The kit comprises a lipoparticle comprising membrane spanning protein, a ligand of the membrane protein, and a substrate to which the lipoparticle can be attached. The kit further comprises an applicator, which applicator can be used to attach the lipoparticle to the substrate and/or for applying the ligand such that the ligand is contacted with the lipoparticle comprising the membrane protein. Such an applicator includes, but is not limited to, a pipette, an injection device, a dropper, and the like.

One skilled in the art will understand that the kit includes a lipoparticle already attached to a substrate with or without the ligand being bound to the membrane protein. The substrate can then be examined using methods well known in the art to detect any change in the substrate mediated by or associated with the ligand binding with its cognate membrane receptor present in the lipoparticle.

Moreover, the kit comprises an applicator and an instructional material for the use of the kit. These instructions simply embody the examples provided herein.

The invention also includes a kit for identifying a potential ligand of a membrane protein. The kit comprises a lipoparticle comprising a membrane protein. The kit includes a kit where the lipoparticle is attached to a surface and further includes where a lipoparticle is provided separately from the surface, which is also provided in the kit. The kit further comprises a test ligand, or a plurality of such ligands, such as, but not limited to, a library of test ligands to be assessed for their ability to specifically bind with the membrane protein present in the lipoparticle.

The kit further comprises an applicator, where the applicator can be used to attach the lipoparticle to the surface and/or to apply the test ligand to the surface such that the test ligand can contact and bind with the lipoparticle bound to the surface.

The invention includes a kit for identifying a compound that affects binding between a ligand and a membrane protein receptor. The kit comprises a lipoparticle comprising a membrane protein and a surface to which the lipoparticle can be attached. The kit comprises where the lipoparticle and surface are provided separately or where the lipoparticle is provided already attached to the surface.

In one aspect, the surface includes a wide variety of sensor surfaces, such as, but not limited to, a wide plethora of biosensor chips that are known in the art or to be developed in the future.

Further, as more fully set forth elsewhere herein, the membrane protein encompasses a wide plethora of membrane spanning proteins that span the lipid bilayer at least once.

Moreover, the kit comprises an applicator and an instructional material for the use of the kit. These instructions simply embody the examples provided herein.

One skilled in the art would appreciate, based upon the disclosure provided herein, that the invention encompasses a kit where the lipoparticle is provided physically separated from a ligand and where the ligand is already bound with the lipoparticle. Similarly, the invention encompasses a kit where the lipoparticle is provided physically separated from the surface, as well as a kit where the lipoparticle is provided attached to the surface. Further, the skilled artisan would understand that the invention encompasses a kit with all possible permutations such that the ligand can be bound with the lipoparticle which is, in turn, attached to the surface, or each is provided separately, or any permutation thereof.

As more fully set forth elsewhere herein, the kit comprises a wide plethora of membrane spanning proteins, lipoparticles, and surfaces, and combinations thereof. Moreover, the kit comprises an applicator and an instructional material for the use of the kit. These instructions simply embody the examples provided herein.

DEFINITIONS

Certain terminology is used herein as follows.

The articles "a" and "an" are used herein to refer to one or to more than one (i.e., to at least one) of the grammatical object of the article. By way of example, "an element" means one element or more than one element.

By the term "applicator" as the term is used herein, is meant any device including, but not limited to, a hypodermic syringe, a pipette, and the like, for attaching a lipoparticle and/or composition of the invention to a surface, including a sensor surface. Further, the applicator can be used to contact a ligand and/or a test compound with a lipoparticle.

The term "enveloped virus vector" means an enveloped virus-like particle comprising at least one cellular virus receptor protein contained within the envelope of the particle, wherein the enveloped virus vector is capable of fusing with a target cell which comprises a viral envelope protein to which the cellular virus receptor protein is cognate.

The term "enveloped virus-like particle" means a composition of matter comprising a replication-competent or replication-incompetent virus surrounded by a lipid-containing virus envelope and at least one of a viral envelope protein and a cellular virus receptor protein, wherein the virus-like particle is incapable of replication in the absence of a cell.

The term "recombinant enveloped virus vector" means an enveloped virus vector comprising a nucleic acid which has been manipulated by any recombinant nucleic acid protocol known in the art (see, e.g. Sambrook, et al., 1989, In: *Molecular Cloning: A Laboratory Manual*, Cold Spring Harbor Laboratory, New York).

The term "enveloped virus" means a virus comprising an envelope.

The terms "envelope" and "viral envelope" mean the lipid-containing or lipoprotein-containing membrane which surrounds the virion of an enveloped virus or at least one component of such a virion.

The term "cellular virus receptor protein" means a protein which, in a normal cell, is encoded by the cell and, at least under certain conditions, is associated with the outer surface of the membrane of the cell, wherein the protein is capable of specifically interacting with a viral envelope protein of an enveloped virus to facilitate attachment of the virus to the cell. A cellular virus receptor protein is functional if it is located in the outer membrane of the cell and is oriented such that the portion of the cellular virus receptor protein which is capable of interacting with a viral envelope protein contacts the extracellular medium. A cellular virus receptor protein is also functional if it is located in the envelope of an enveloped virus or a virus vector having an envelope and it is oriented such that the portion of the cellular virus receptor protein which is capable of interacting with a viral envelope protein contacts the medium in which the virus or virus vector is suspended. A cellular virus receptor protein may be a full-length protein, as encoded by a normal cell, or may be a fragment thereof.

The term, "cellular," as it is used to refer to a virus receptor protein, means that the virus receptor protein is normally encoded by the cell and not viral DNA. However, the term also applies to a protein expressed by a recombinant virus wherein a cellular nucleic acid encoding the receptor protein has been inserted into the genome of the recombinant virus for expression therefrom. Furthermore, the term also applies when the protein is provided to a virus or a virus vector in the form of a protein or a peptide.

The tell "cellular chemokine receptor" means a protein, which, when expressed by a cell which normally encodes the chemokine receptor, is capable of interacting with a chemokine in the extracellular medium. By way of example, CCR5 is a chemokine receptor which, when expressed by a cell which naturally encodes CCR5, is capable of interacting with RANTES, MIP-1alpha, AND MIP-1beta.

The term "viral envelope protein" means a protein which, in a normal enveloped virus, is encoded by the genome of the virus and is associated with the envelope of the virus, wherein the protein is capable of specifically interacting with a cognate cellular virus receptor protein to facilitate attachment of the virus to a cell. Viral envelope proteins include, but are not limited to, glycoproteins. A viral envelope protein is functional if it is located in the envelope of an enveloped virus or a virus vector and is oriented such that the portion of the viral envelope protein which is capable of interacting with a cognate cellular virus receptor protein contacts the medium in which the virus or virus vector is suspended. A viral envelope protein is also functional if it is located in the outer membrane of a cell and is oriented such that the portion of the viral envelope protein which is capable of interacting with a cognate cellular virus receptor protein contacts the extracellular medium. A functional viral envelope protein may be a full-length protein, as synthesized during normal replication of a virus, or it may be a fragment thereof.

The term "retroviral envelope protein" means a viral envelope protein of a retrovirus.

A cellular virus receptor protein is "cognate" to a viral envelope protein if the cellular virus receptor protein is capable of interacting with the viral envelope protein and facilitating fusion of the membrane or envelope with which it is associated and the membrane or envelope with which the viral envelope protein is associated.

A cell and an enveloped virus or enveloped virus vector are "capable of fusing" if a protein of the cell and a protein of the virus or vector are capable of specifically interacting and facilitating the fusion of a membrane of the cell and the envelope of the virus or vector, whereby the contents of the envelope of the virus or vector and the contents of the membrane of the cell are combined.

The term "cell" means any type of living cell. Cells of both unicellular and multicellular organisms are included. Cells of multicellular organisms are preferred, and cells of animals are more preferred. Cells of vertebrates are still more preferred, and cells of mammals are even more preferred. Most preferably, the cells are human cells.

The term "virus-infected cell" means a cell which has been infected by a virus including, but not limited to, an enveloped virus, and which comprises a viral protein including, but not limited to, a viral envelope protein in its outer membrane.

The term "producer cell" means a cell in which an enveloped virus or an enveloped virus vector of the invention can be generated.

The term "target cell" means a cell with which fusion with an enveloped virus or an enveloped virus vector of the invention is desired. A target cell corresponding to the enveloped virus vector of the invention comprises a functional viral envelope protein to which the cellular virus receptor protein of the enveloped virus vector is cognate.

As used herein, an "instructional material" includes a publication, a recording, a diagram, or any other medium of expression which can be used to communicate the usefulness of the lipoparticle and/or composition of the invention in the kit for assessing protein binding, identifying ligands for a membrane protein, identifying a compound that affects a ligand binding with its cognate membrane receptor protein, and the like, as more fully recited elsewhere herein. Optionally, or alternately, the instructional material may describe one or more methods of using a lipoparticle of the invention. The instructional material of the kit of the invention may, for example, be affixed to a container which contains the lipoparticle and/or composition of the invention or be shipped together with a container which contains the lipoparticle and/or composition. Alternatively, the instructional material may be shipped separately from the container with the intention that the instructional material and the compound be used cooperatively by the recipient.

The term "host cell" means a ell which is susceptible to infection by an enveloped virus.

The term "test cell" means a cell which comprises at least one of a viral envelope protein, a cellular virus receptor protein, and a test protein.

The term "control cell" means a cell used in conjunction with a test cell, which is of the same cell type as the test cell, and Which does not comprise a viral envelope protein, a cellular virus receptor protein, or a test protein.

The term "test protein" means an unknown protein which may be a viral envelope protein, a cellular virus receptor protein, or neither of these.

The term "competent portion of the genome of an enveloped virus" means the portion of the genome of the enveloped virus which, when expressed in a cell, results in formation of at least one virus-like particle.

The term "host range" describes an organism or a group of organisms, the cells of which are susceptible to infection by an enveloped virus.

The term "tissue tropism" describes a tissue or a group of tissues of an organism, the cells of which are susceptible to infection by an enveloped virus.

The term "tropism determinant" means a component of an outer membrane of a cell or a component of an envelope of a virus, which component is involved in infection of the cell by the virus or is capable of affecting a second component which is involved in infection of the cell by the virus. Non-limiting examples of tropism determinants include a cellular virus receptor protein, a viral envelope protein, a protein which interacts with a cellular virus receptor protein, and a protein which interacts with a viral envelope protein.

The term "intracellular antagonist of HIV" means a composition of matter which, when provided to the interior of a cell infected with HIV, is capable of interfering with maintenance or replication of HIV or with integration of the HIV genome into the host cell genome.

The term "antiviral agent" means a composition of matter which, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, Retrovir® Glaxo Wellcome Inc., Research Triangle Park, N.C.) is an antiviral agent which is believed to prevent replication of HIV in human cells.

The term "imaging agent" means a composition of matter which, when provided to a cell, facilitates detection of the cell. Numerous imaging agents are known and described in the literature. By way of example, enzymes, such as beta-galactosidase, which are capable of catalyzing a reaction involving a chromogenic substrate may be provided to a cell. When the chromogenic substrate is reacted with the enzyme, the cell is detectable. In this sense, the enzyme is considered herein to be an imaging agent. Further by way of example, compounds, the presence of which may be directly detected, may be provided to a cell, such as compounds which emit gamma radiation or which fluoresce, which may be detected using an appropriate detection apparatus.

The term "antisense nucleic acid" means a nucleic acid polymer, at least a portion of which is complementary to a nucleic acid which is present in a cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

The term "cytotoxic compound" means a composition of matter which, when provided to a cell, is capable of killing the cell.

The term "library" means a plurality of nucleic-acid-containing vectors.

"A multiple membrane spanning protein," as the term is used herein, is a polypeptide that spans the cell membrane at least twice. That is, the peptide is typically present in a cell membrane where it spans the Lipid bilayer at least twice.

The term "non-human animal model of a human disease or disorder" means a non-human animal which has been rendered susceptible to infection by a human pathogenic enveloped virus and which, when so infected, exhibits a physiological condition which is analogous to a symptom exhibited by a human infected with the same virus. The term also means a non-human animal which is susceptible to infection by a non-human pathogenic enveloped virus. When the non-human animal is infected with the non-human pathogenic enveloped virus, the animal exhibits a pathology which is similar to the pathology of a human infected with the corresponding human pathogenic enveloped virus. By way of example, certain known species of monkeys are susceptible to infection by SIV, giving rise to a disease which is similar to that in humans infected with HIV.

The term "staged delivery of enveloped virus vectors" means sequential delivery to an organism of a plurality of enveloped virus vectors of the invention, wherein a first enveloped virus vector is capable of fusing with a cell of the organism, and wherein delivery of the first enveloped virus vector renders the cell susceptible to fusion with a second enveloped virus vector, which is subsequently delivered to the cell.

The term "pharmaceutically-acceptable carrier" means a chemical composition with which an enveloped virus vector of the invention may be combined for administering the vector to an animal, preferably to a human.

The invention is now described with reference to the following examples. These examples are provided for the purpose of illustration only and the invention should in no way be construed as being limited to these examples but rather should be construed to encompass any and all variations which become evident as a result of the teaching provided herein.

Example 1

An Enveloped Virus Vector Comprising CD4 and a Chemokine Receptor: a Gene Delivery Vector that Fuses with HIV- or SIV-Infected Cells The delivery to HIV- and SIV-infected cells of a gene encoding luciferase protein using the enveloped virus vector of the invention is described. The results presented herein exemplify a novel method to deliver antiviral genes directly to an HIV-1-infected cell in vivo and provides a novel treatment strategy to complement existing antiviral therapies. In addition, the method can be used to deliver a component of an enveloped virus vector to an HIV-infected cell. Furthermore, by substituting a viral envelope protein and a cellular virus receptor protein corresponding to any other enveloped virus, the methods exemplified herein may be applied to make and use an enveloped virus vector capable of fusing with cells infected with that other enveloped virus.

Co-expression of CD4 and an appropriate chemokine receptor is sufficient to render human and nonhuman cells susceptible to infection by HIV or SIV (analogous to FIG. 1, Panel A). In the results described herein, co-expression of CD4 and a chemokine receptor in the envelope of an enveloped virus vector was demonstrated to facilitate fusion of the enveloped virus vector with a cell infected with HIV or SIV (analogous to FIG. 1, Panel B).

An illustration of an aspect of the invention is depicted in FIG. 1. FIG. 1, Panel A is an illustration which depicts entry of HIV or SIV into a cell susceptible to infection by either virus. The circular entity having knobby projections represents the viral envelope of an HIV virion or an SIV virion, wherein the knobby projections represent viral envelope proteins. The pair of parallel lines which define a portion of a rectangle having rounded corners represents a portion of the membrane of a cell. The concave side of the cell membrane represents the interior face of the cell membrane, and the convex side of the cell membrane represents the exterior of the cell. CD4 embedded in the cell membrane is represented by a black entity which spans the cell membrane and has a single semi-circular end. A cytokine receptor protein is represented by a series of irregular lines, some of which span the cell membrane. Interaction among at least one viral envelope protein, CD4, and at least one cytokine receptor leads to fusion of the viral envelope and the cell membrane, whereby the contents of the viral envelope are delivered to the interior of the cell.

FIG. 1, Panel B is an illustration which depicts targeting of cells infected with HIV or SIV using an enveloped virus vector of the invention. In this panel, the representations are the same as those used in Panel A. However, in Panel B, the viral envelope proteins are present in the cell membrane, representing a cell which is infected with HIV or SIV. CD4 and a cytokine receptor are present in the envelope of the enveloped virus vector. Analogously to the situation depicted in Panel A, but in the opposite orientation, interaction among at least one viral envelope protein, CD4, and at least one chemokine receptor leads to fusion of the envelope of the enveloped virus vector and the cell membrane, whereby the contents of the envelope of the enveloped virus vector are delivered to the interior of the cell.

The materials and methods used in the experiments presented in Example 1 are now described.

The enveloped virus vector used in Example 1 comprised one or more of CD4 and a chemokine receptor. The enveloped virus vector was generated by providing to a producer cell line the HIV-1 provirus, NL-R$^-$E$^-$luc, which comprises a competent portion of the HIV-1 genome. NL-R$^-$E$^-$luc (Connor et al., 1995, Virology 206:935-944) is deficient for env and nef, two viral genes, the expression of which is known to reduce the amount of CD4 on the plasma membrane (Crise et al., 1990, J. Virol. 64:5585-5593; Jabbar et al., 1990, J. Virol. 64:6297-6304; Garcia et al., 1991, Nature 350:508-511; Mariani et al., 1993, Proc. Natl. Acad. Sci. USA 90:5549-5553; Benson et al., 1993, J. Exp. Med. 177:15614566; Aiken et al., 1994, Cell 76:853-864). NL-R$^-$E$^-$luc also comprises a luciferase reporter gene that facilitates detection and quantitation of the fusion of the enveloped virus vector with a target cell.

The enveloped virus vectors described in Example 1 were generated by transient cotransfection of approximately 5×10$^6$ producer cells using one or more of four plasmids. An enveloped virus vector comprising CD4 and a chemokine receptor was generated using 10 micrograms of plasmid pNL-R$^-$E$^-$luc (which comprises the NL-R$^-$E$^-$ luc provirus; Connor et al., 1995, Virology 206:935-944), 10 micrograms of plasmid pT4 (which comprises a gene encoding CD4; Littman et al., 1985, Cell 40:237-246), and 10 micrograms of either plasmid pLESTR/cDNA3 (which comprises a gene encoding CXCR4; Berson et al., 1996, J. Virol. 70:6288-6295) or plasmid pCKR5/cDNA3 (which comprises a gene encoding CCR5; Doranz et al., 1996, Cell 85:1149-1158). Other enveloped virus vectors were generated wherein the plasmid encoding CD4, the plasmid encoding a chemokine receptor, or both were omitted, and wherein an equivalent quantity of plasmid pcDNA3 (which is commercially available, e.g. from Invitrogen, Carlsbad, Calif.) was substituted for the omitted plasmid(s), so that a total of 30 micrograms of plasmid DNA per transfection was used in each case. Forty-eight hours post-transfection, transfected producer cells in culture were harvested, and enveloped virus vector was collected by passing the culture medium through a membrane having a pore size of 0.22 micrometer to remove producer cells. Preparations of enveloped virus vector were divided into aliquots, and the aliquots were stored at −80° C. Each preparation of enveloped virus vector was quantified using a commercial HIV-1 p24 assay (Dupont; Wilmington, Del.).

The producer cells used in Example 1 were QT6 cells, which are quail cells that lack both CD4 and chemokine receptors (Moscovici et al., 1977, Cell 11:95-103; Doranz, 1996, Cell 85:1149-1158). Enveloped virus vector preparations were normalized to achieve equivalent p24 levels among the preparations.

The ability of the enveloped virus vector to fuse with CEMx174 target cells which were chronically infected with HIV or SIV was assessed by contacting the vector with target cells as follows. Infected or non-infected target cells were transferred to 24-well plates. Each well contained approximately 5×10$^4$ target cells and an amount of an enveloped virus vector preparation corresponding to 10 nanograms of p24 for the preparation. The target cells and the enveloped virus vector were incubated overnight. The following day, 0.5 milliliter of fresh medium (comprising RPMI-1640 medium supplemented with 10% (v/v) fetal bovine serum, 100 units per milliliter penicillin, 100 micrograms per milliliter streptomycin, and 2 millimolar L-glutamine) was added to each well. Four days postinfection, cell cultures were harvested, pelleted, washed twice with phosphate-buffered saline (PBS), and the cells were lysed using 150 microliters of luciferase lysis buffer (Promega Corp.; Madison, Wis.). The amount of luciferase activity present in 20 microliters of lysate was assessed using commercially available reagents, according to the manufacturer's instructions (Promega Corp.; Madison, Wis.). Experiments were repeated at least twice in duplicate, and reported values represent the average of duplicate samples± the standard error of the mean (SEM).

Expression of SIV Viral Envelope Proteins

Target cells were chronically infected with SIVmac239 or SIVmac239/MT. SIVmac239/MT is a variant of SIVmac239 in which the cytoplasmic portion of the transmembrane envelope protein is modified by a tyrosine-to-cysteine substitution at amino acid position 721 and a premature stop codon is present at amino acid position 734. It has been demonstrated that another SIV viral envelope protein containing these substitutions exhibits markedly enhanced levels of expression on the plasma membrane of the cells infected therewith (Labranche et al., 1995, J. Virol. 69:5217-5227; Sauter et al., 1996, J. Cell Biol. 132:795-811). SIVmac239/MT was constructed by cloning the 475 nucleotide Nhe1-Bg12 fragment from pCPenv into the corresponding sites of pVP-2. To recover infectious virus, the resulting plasmid (p3'239/MT) and pVP-1 were digested with Sph1, ligated, and transfected into target cells. Supernatants were harvested, clarified by centrifugation for five minutes at 2,000×g, and SIVmac239/MT was obtained by filtration using a membrane having a pore diameter of 0.22 micrometer. Preparations of virus were divided into aliquots, and the aliquots were stored at −80° C.

The quantity of viral envelope protein α-SIV gp120 expressed on the surface of cells chronically infected with SIVmac239 or SIVmac239/MT was estimated by flow cytometry using a FACScan analyzer (Becton Dickenson). Pelleted cells were resuspended in ice-cold staining buffer which comprised PBS, 0.1% (w/v) bovine serum albumin, 0.02% (v/v) sodium azide, and mAb101.1, a monoclonal antibody which specifically recognizes α-SIV gp120 (Labranche et al., 1995, J. Virol. 69:5217-5227; Sauter et al., 1996, J. Cell Biol. 132:795-811). Following suspension, cells were incubated for 30 minutes at 4° C. with fluorescein isothiocyanate-conjugated F(ab)$_2$ goat anti-mouse immunoglobulin G. Cells were washed with PBS and fixed in 4% (v/v) paraformaldehyde prior to FACS analysis, Staining results did not appear to be epitope-dependent, since similar staining patterns were obtained using other primary antibodies (Labranche et al., 1995, J. Virol. 69:5217-5227; Sauter et al., 1996, J. Cell Biol. 132:795-811) directed against SIV gp41 (mAb 43.1) or gp120 (mAb 7D3 and mAb 5811).

Enveloped virus vectors were preincubated for two hours at 37° C. with either neutralizing monoclonal antibody α-CD4#19 (Endres et al., 1996, Cell 87:745-756) or antibody DL11, an isotyped matched control. Approximately 5×10⁴ CEMx174 cells Which were chronically infected with either HIV or SIV were added to each well of a 24-well plate. An enveloped virus vector which had been preincubated with one of the two antibodies was added to each well in an amount corresponding to 10 nanograms of p24 for the preparation, and the final concentration of antibody was maintained at 15 micrograms per milliliter in each well. The cells, vectors, and antibodies were incubated for three to four days at 37° C. Following incubation, cells were harvested, washed with PBS, lysed in 150 microliters of luciferase lysis buffer (Promega Corp., Madison Wis.), and the amount of luciferase activity in 20 microliters of lysate was assessed. In selected wells, the enveloped virus vector was not preincubated with α-CD4#19, and α-CD4#19 was not added to the well until sixteen hours after the cells and vector were mixed. Reported values represent the average of duplicate samples±SEM. Experiments were repeated twice in duplicate, and similar results were obtained in each experiment.

Monocyte-derived macrophages (MDM) were isolated from peripheral blood mononuclear cells of healthy seronegative donors and maintained in macrophage media as previously described (Collman et al., 1989, J. Exp. Med. 170: 11494163). Approximately 4×10⁵ MDM cells were cultured for eight days in individual wells of 24-well plastic tissue culture plates prior to infection of the MDM with HIV-1/89.6. No later than ten days postinfection, p24 antigen could be detected in MDM cultures which were infected with HIV, and extensive syncytia were present. Ten days postinfection, MDM were contacted with an enveloped virus vector. Following an additional four days of incubation at 37° C., luciferase activity was assessed in the MDM as described herein. Reported luciferase activity values represent the average of duplicate samples±SEM.

The results obtained in the experiments presented in Example 1 are now described.

Figure 2A:
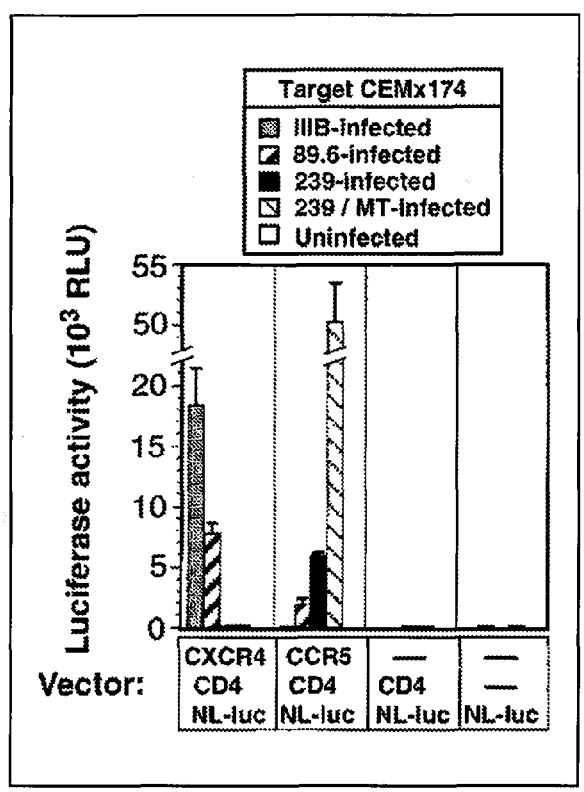
FIGS. 2A and 2B, is a pair of graphs depicting reporter gene activity as a function of the target cell and the virus which is used to deliver the reporter gene to target cells. The bar graph in FIG. 2A depicts luciferase activity measured in CEMx174 cells which were chronically infected with HIV or SIV and which were contacted with the enveloped virus vector indicated at the bottom of the graph. Because each enveloped virus vector used encoded luciferase, the level of luciferase detected corresponds to the ability of the vector to fuse with the cell. The graph in FIG. 2B depicts cell surface expression of viral envelope glycoprotein gp120 in CEMx174 cells which were infected with SIVmac239 or with SIVmac239/MT or which were not infected, as assessed by FACS.
Figure 2B:
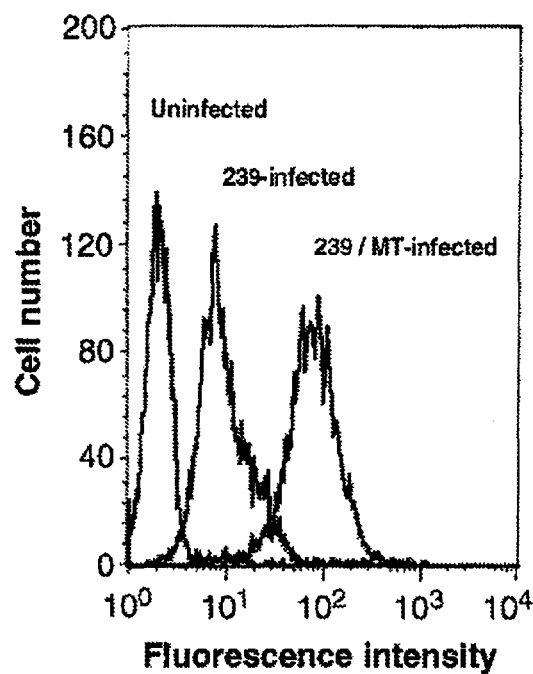

Enveloped virus vectors comprising CD4 and a chemokine receptor were evaluated for their ability to transduce HIV- and SIV-infected target cells. As depicted in FIG. 2, Panel A, an enveloped virus vector comprising CD4 and a particular chemokine receptor was able to transduce HIV- or SIV-infected cells in a manner that corresponded to whether the cellular virus receptor protein(s) were cognate to the viral envelope protein(s) which were expressed on the cells. Accordingly, an enveloped virus vector comprising CD4 and CXCR4 was able to fuse with CEMx174 cells which had been infected with HIV-1/IIIB or HIV-1/89.6, but was not able to fuse with cells which had been infected with SIVmac239. An enveloped virus vector comprising CD4 and CCR5 was able to fuse with CEMx174 cells which had been infected with SIVmac239 or HIV-1/89.6, but was not able to fuse with cells which had been infected with HIV-1/IIIB. None of the enveloped virus vectors comprising a cellular virus receptor protein were able to fuse with non-infected cells.

The amount of viral envelope protein expressed on infected CEMx174 cells significantly influenced the efficiency of fusion with enveloped virus vectors. Cells which were chronically infected with SIVmac239/MT, an engineered variant of SIVmac239, exhibited approximately 10-fold higher surface envelope protein expression, as assessed by FACS using gp120- and gp41-specific monoclonal antibodies (FIG. 2, Panel B). Cells infected with SIVmac239/MT also displayed markedly increased susceptibility to fusion with enveloped virus vectors which comprised CD4 and CCR5 (FIG. 2, Panel A).

These studies further demonstrate that an enveloped virus vector comprising a cellular virus receptor protein which is cognate to a viral envelope protein of HIV can be used to deliver the vector specifically to HIV-infected cells.

Effect of CD4 Availability

Figure 3A:
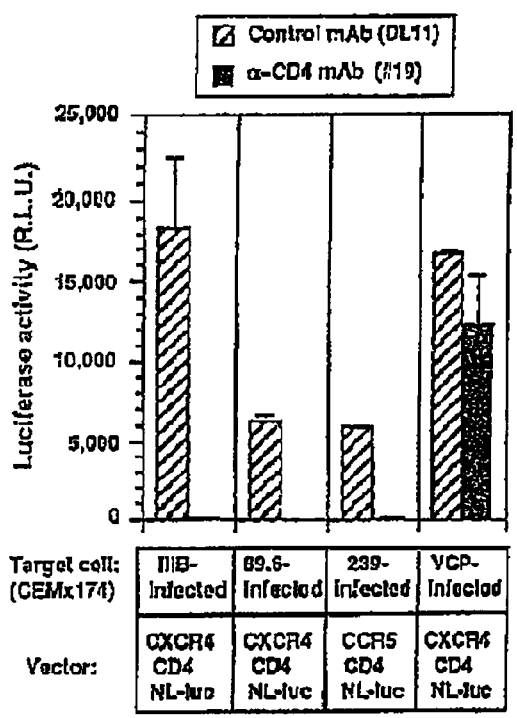
In FIG. 3A, the enveloped virus vector used in each experiment was pre-incubated with either α-CD4#19 antibody or a control antibody prior to mixing the vector with the cells. Luciferase activity levels assessed following transfection of cells with a vector incubated with α-CD4#19 antibody are represented by solid bars. Luciferase activity levels assessed following transfection of cells with a vector incubated with a control antibody are represented by striped bars.
Figure 3B:
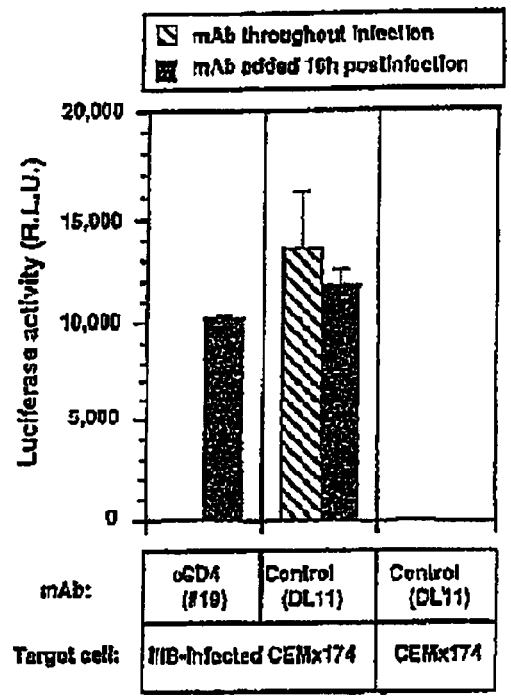

Studies were performed to evaluate the dependence upon the availability of CD4 of the ability of the vector to fuse with CEMx174 cells using enveloped virus vectors comprising CD4 and either CXCR4 or CCR5. As depicted in FIG. 3, Panel A, addition to the infection mixture of α-CD4#19, a monoclonal antibody specific for CD4 which has been demonstrated to block HIV and SIV infection of cells (Endres et al., 1996, Cell 87:745-756), completely inhibited fusion of HIV- or SIV-infected CEMx174 cells with enveloped virus vectors comprising CD4 and either CXCR4 or CCR5. Remarkably, α-CD4#19 minimally inhibited fusion of enveloped virus vectors comprising CD4 and CXCR4 with CEMx174 cells which had chronically infected by HIV-2/VCP, an HIV-2 variant demonstrated to utilize CXCR4 as a receptor in the absence of CD4 (Endres et al., 1996, Cell 87:745-756). Taken together, these results indicate that fusion of enveloped virus vectors with cells correlated with the amount of viral envelope protein on the cell surface and reflected the CD4 dependence of the virus with which the cells were infected.

The ability of enveloped virus vectors comprising CD4 and either CXCR4 or CCR5 to target HIV- or SIV-infected cells was consistent with a single round of entry. However, it was theoretically possible that following fusion of the vector with the cell, the NL-R⁻E⁻luc recombinant retrovirus vector replicated and was subsequently packaged with HIV or SW envelope glycoproteins expressed by the target cell to form infectious particles. If formed, these infectious particles could potentially infect CD4⁺ cells in a subsequent round of entry. To confirm that infection of target cells by such infectious particles did not occur, expression of the gag gene in the target cells was determined and the presence on the surface of the target cells of CD4 was assessed by fluorescence activated cell sorting (FACS). One hundred percent of target cells were infected, as determined by detection of intracellular gag gene products (Labranche et al., 1995, J. Virol. 69:5217-5227; Sauter et al., 1996, J. Cell Biol. 132:795-811). Furthermore, target cells expressed no detectable surface CD4, as assessed by FACS. Therefore, these cells were resistant to superinfection by any infectious particles that might have been formed. To further confirm that infection of target cells by infectious particles did not occur, α-CD4#19 antibody was added to the infection mixture sixteen hours after the initiation of incubation of the target cells with a recombinant retrovirus vector. The purpose of adding the antibody was to inhibit any superinfection which might involve CD4. As demonstrated by the results depicted in FIG. 3, Panel B, inhibition of fusion of the enveloped virus vector with the cells was apparent when α-CD4#19 antibody was added concurrently with the addition of vector, but not when α-CD4#19 antibody was added sixteen hours after the initiation of incubation of the cells with the vector. Taken together, these results indicate that a second round of infection did not occur in the target cells.

Fusion of the Enveloped Virus Vector with Monocyte-Derived Macrophages

Figure 4:
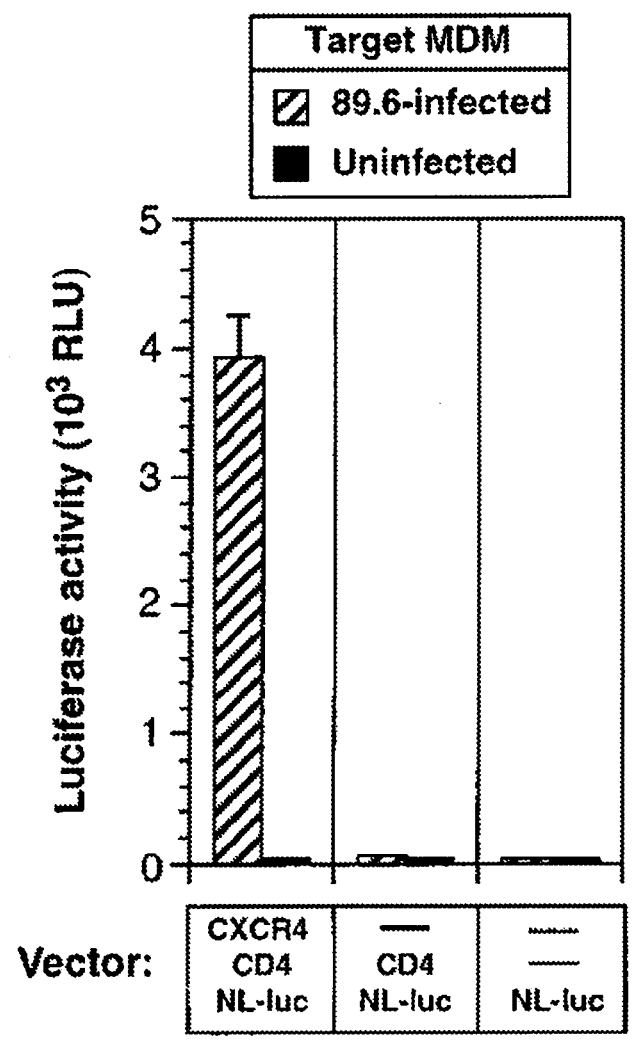
FIG. 4 is a graph depicting the level of luciferase activity measured following contact of non-infected and HIV-infected monocyte-derived macrophages (MDM) with enveloped virus vectors. Striped bars represent results obtained using non-infected MDM. Solid bars represent results obtained using HIV-1/89.6-infected MUM.

In order to demonstrate that the results obtained using CEMx174 cells are equally applicable to a primary cell type, the ability of an enveloped virus vector comprising CD4 and either CXCR4 or CCR5 to fuse with monocyte-derived macrophages which had been acutely infected with HIV was examined. An enveloped virus vector comprising CD4 and CXCR4 was able to fuse with MDM which had been acutely infected with HIV-1/89.6 (FIG. 4) and was unable to fuse with non-infected MDM. Furthermore, an enveloped virus vector comprising CD4, but not comprising CXCR4, was unable to fuse with MDM that had been acutely infected with HIV-1/89.6.

HIV-derived enveloped virus vectors offer a distinct advantage over enveloped virus vectors derived from avian or murine viruses with respect to targeting post-mitotic cells such as macrophages (Naldini et al., 1996, Science 272:263-267). Transduction of HIV-1-infected MDM may be enhanced if the enveloped virus vector further comprises Vpr protein (Connor et al., 1995, Virology 206:935-944; Naldini et al., 1996, Science 272:263-267).

The results presented in this Example demonstrate that an enveloped virus vector comprising CD4 and a cytokine receptor is an effective vehicle for delivering vector components, such as genes, directly and specifically to HIV- and SIV-infected cells, including non-dividing, post-mitotic cells. Furthermore, these results demonstrate that fusion resulting from the interaction between the HIV and SW envelope proteins and their cognate cellular virus receptor proteins is not dependent upon which protein is borne by the cell and which is borne by the vectors.

Figure 5A:
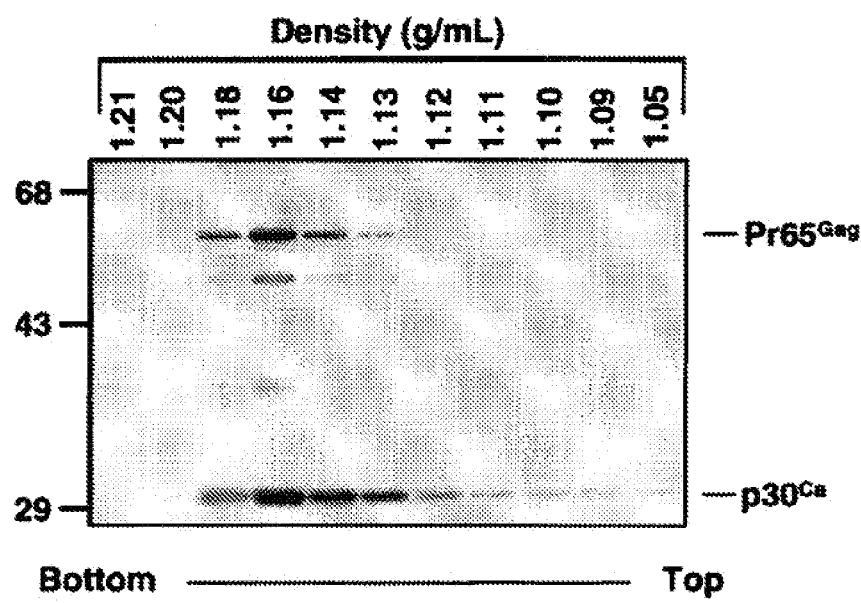
FIGS. 5A and 5B, is a pair of images depicting the results of Western blot analysis of proteins in fractions obtained from a density gradient sedimentation centrifuge tube. Virions obtained during preparation of MLV (Tva) were layered onto the solution in the centrifuge tube prior to centrifugation. Each lane in the images corresponds to a single density gradient fraction, and the density corresponding to the fraction is indicated at the top of each lane.
Figure 5B:
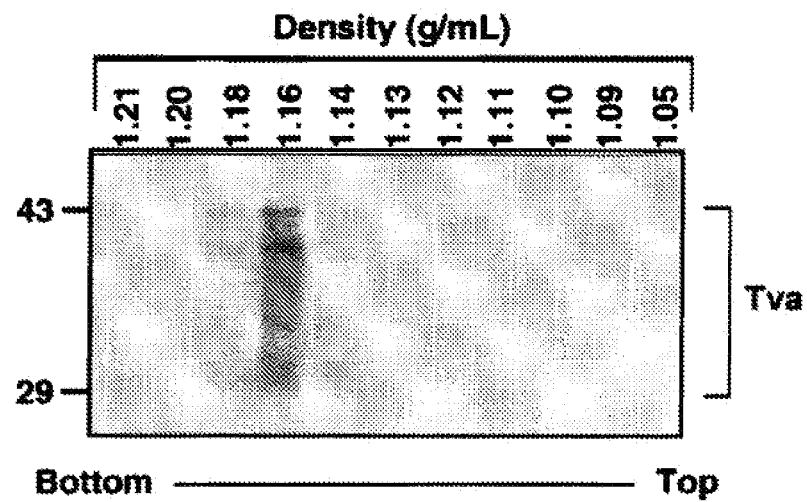

An enveloped virus vector comprising a cellular virus receptor protein can be used to deliver a vector component to HIV- and SIV-infected cells. In addition to providing a potential therapeutic strategy to target reservoirs of HIV-infected cells in patients, enveloped virus vectors comprising CD4 and a cytokine receptor also provide a convenient means for screening compounds for their ability to interfere with interactions between a cellular virus receptor protein and a viral envelope protein to which it is cognate. Because the orientation of the cellular virus receptor protein and the viral envelope protein have been reversed, this system permits identification of compounds which exert their inhibitory effects by true steric interference. Thus, compounds which exert their inhibitory effects by steric interference may be distinguished from compounds which, for example, induce receptor internalization or desensitization. In addition, reversing the orientation of interactions between a cell-encoded cellular virus receptor protein and a virus-encoded viral envelope protein to which it is cognate may be applied analogously with respect to any enveloped virus and can be used as a general approach to screen mammalian cells for cellular virus receptor proteins.

Example 2

Efficient Infection Mediated by an Enveloped Virus Vector Comprising a Cellular Virus Receptor Protein Methods which were used to make and use enveloped virus vectors comprising a cellular virus receptor protein are described in this Example. As described herein, these vectors were able to deliver a gene to the interior of a cell comprising a viral envelope protein to which the cellular virus receptor protein is cognate.

Many host cell surface proteins, including cellular virus receptor proteins, are capable of being incorporated into the envelope of an enveloped virus. To assess the functional significance of these cell-encoded proteins, murine leukemia virus vectors were produced, wherein the viruses comprised either the cellular virus receptor protein for Rous sarcoma virus (hereinafter, "RSV") or the cellular virus receptor protein for ecotropic murine leukemia virus (hereinafter, "MLV"). These receptor-pseudotyped murine leukemia viruses (hereinafter, "RPMLV"; an embodiment of the enveloped virus vector of the invention) efficiently infected cells which expressed a viral envelope protein to which the cellular virus receptor protein of the RPMLV was cognate.

RPMLV were constructed which comprised a cellular virus receptor protein. When the cellular virus receptor protein was Tva, the subgroup A RSV (hereinafter, "RSV(A)") receptor protein, the RPMLV was designated MLV(Tva). When the cellular virus receptor protein was MCAT-1, the ecotropic MLV receptor, the RPMLV was designated MLV(MCA'F). Tva interacts with EnvA, a viral envelope protein of RSV(A), and cells expressing Tva have no apparent requirement for additional factors or co-receptors to mediate infection of the cells by RSV(A) (Bates et al., 1993, Cell 74:1043-1051; Connolly et al., 1994, J. Virol. 68:2760-2764; Gilbert et al., 1994, J. Virol. 68:5623-5628). MCAT-1 is a multiple membrane spanning amino acid transport protein which has physical properties distinct from Tva. Cells expressing MCAT-1 do not appear to require additional factors or co-receptors to mediate infection of the cells by MLV.

MLV(Tva) was made by transiently co-transfecting $6\times10^6$ 293T cells using 15 micrograms of each of three plasmids as described (Soneoka et al., 1995, Nucl. Acids Res, 23:628-633). The three plasmids used for co-transfection were plasmid pCB6 0.95, which encodes the tva gene, plasmid pHit60, which encodes MLV gag-pol, and plasmid pHit111, an MLV packing genome which encodes a β-galactosidase reporter gene. Thirty-six hours post transfection, the medium comprising the transfected cells was harvested and clarified by centrifugation at 2,300×g to yield culture supernatant. The culture supernatant was divided into aliquots, and the aliquots were stored at −80° C. until they were used for infection assays.

Incorporation of Tva protein into the envelope of RPMLV was assessed by equilibrium density gradient centrifugation analysis of transiently-produced RPMLV particles. Culture supernatant was centrifuged for eighty-five minutes at 28,000 rotations per minute in an SW 28 rotor in a centrifuge tube containing a 20% (w/v) sucrose solution layered on top of a 60% (w/v) sucrose solution. Following this centrifugation, a virion suspension was retrieved from the portion of the centrifuge tube which contained the 20%/60% (w/v) sucrose interface. The virions were diluted and the suspension was centrifuged for fifty minutes at 41,000 rotations per minute in an SW41 rotor in a centrifuge tube containing a 20% (w/v) sucrose solution layered on top of a 60% (w/v) sucrose solution. Following this centrifugation, a second virion suspension was retrieved from the portion of the centrifuge tube which contained the 20%/60% (w/v) sucrose interface. The second virion suspension was diluted three-fold with PBS and layered on top of a 15%-45% (w/v) sucrose gradient in a gradient centrifuge tube. The gradient centrifuge tube was centrifuged for sixteen hours in an SW 41 rotor at 35,000 rotations per minute. Following this centrifugation, one milliliter fractions were collected from the gradient centrifuge tube. Each fraction was centrifuged for ten minutes at 55,000 rotations per minute in an SW55 rotor in a centrifuge tube containing a 20% sucrose solution layered on top of a 60% (w/v) sucrose solution. A third virion suspension was retrieved from the portion of the centrifuge tube which contained the 20%/60% (w/v) sucrose interface. The virions in the third virion suspension were then lysed using RIPA buffer. RIPA buffer comprises 140 millimolar NaCl, 10 millimolar Tris buffer adjusted to pH 8.0, 5 millimolar EDTA, 1% (w/v) sodium deoxycholate, 1% (v/v) Triton X-100, and 0.1% (v/v) sodium dodecyl sulfate. Suspension of virions in RIPA buffer is sufficient to lyse virions and solubilize virion proteins. The proteins in the lysed virion suspension were separated on a 12.5% (w/v) SDS-PAGE gel, transferred to nitrocellulose, and subjected to Western blot analysis using either anti-Gag antibody (Rong et al., 1997, J. Virol. 71:3458-3465) or anti-Tva antibody (Rong et al., 1995, J. Virol. 69:48474853). Western blot analysis of the SDS-PAGE-separated proteins of the lysed virion suspension revealed that MLV Gag proteins p30 and Pr65 co-sedimented with the multiple bands characteristic of Tva (FIG. 5). Furthermore, virions comprising Tva were recovered from sucrose gradient fractions corresponding to the density of intact MLV virions under these conditions (Young et al., 1990, Science 250:1421-1423; Jones et al., 1990, J. Virol. 64:2265-2279). In parallel experiments in which pHit60 was omitted from the transfection mixture, Tva was not recovered from fractions of the sucrose gradient corresponding to the density of intact MLV virions. These results demonstrated that Tva was incorporated into intact virions to produce MLV(Tva).

The ability of MLV(Tva) to infect cells was evaluated using cells chronically infected with RSV(A). Quail QT6 cells were infected with RCAS(A)AP, a replication-competent RSV vector comprising an alkaline phosphatase (AP) reporter gene. After several passages, all QT6 cells exhibited AP reporter phenotype and appeared to be chronically infected. When cells which had been infected with RCAS(A)AP were exposed to MLV(Tva), fusion of the cells with MLV(Tva) was observed. The MLV(Tva) preparation exhibiting a virus titer of $7 \times 10^2$ fusible units per milliliter was used as a stock suspension (Table 1). QT6 cells that had not been infected with RCAS(A)AP were not susceptible to fusion with MLV(Tva). These experiments demonstrate that expression of a viral envelope protein by cells infected with an enveloped virus renders them susceptible to infection by an enveloped virus vector comprising a cognate cellular virus receptor protein. Table 1. Cells expressing different forms of RSV Env protein were infected overnight with MLV(Tva), fixed, and examined for β-galactosidase activity thirty-six hours post-infection. Virus titer was determined by enumerating cells having β-galactosidase activity, and is expressed as fusible units per milliliter (FU/ml). The data shown is representative of multiple experiments.

|  | Virus Titer (FU/ml) | |
| --- | --- | --- |
|  | 293T Cells | QT6 Cells |
| Chronically infected target cells | | |
| uninfected | — | 0 |
| RSV(A) Infected | — | 700 |
| Transfected target cells | | |
| EnvA | 20,000 | 1,800 |
| EnvC | 0 | 0 |
| EnvA Cl⁻ | 18 | 0 |
| EnvA GPI | 0 | 0 |
| EnvA A34[A]Q35 | 22 | 3 |
| Mock | 0 | 0 |

In another set of experiments, cells transiently expressing various RSV viral envelope proteins and mutants thereof were used as targets for fusion with MLV(Tva). In these experiments, a vector comprising a nucleic acid which encoded one of the RSV envelope glycoproteins or mutants listed in Table 1 was used to transiently transfect $4 \times 10^5$ QT6 cells or $6 \times 10^5$ human 293T cells overnight using CaPO$_4$. The quantity of vector used was equivalent to 3 micrograms of expression plasmid DNA which comprised the env genes listed in Table 1. Transfected cells were contacted overnight with MLV(Tva) forty-eight hours post-transfection. Two days post-infection, the cells were fixed and stained for β-galactosidase activity. MLV(Tva) efficiently fused with both quail and human cells which were transfected with the vector encoding EnvA protein. Cells subjected to identical procedures, with the exception that no DNA was used to transfect the cells (denoted "Mock" in Table 1) were not susceptible to fusion with MLV(Tva). It has been reported that Tva binds specifically to subgroup A viral envelope proteins and does not mediate infection by other subgroups of RSV (Bates et al., 1993, Cell 74:10434051; Connolly et al., 1994, J. Virol. 68:2760-2764; Gilbert et al., 1994, J. Virol. 68:5623-5628). Consistent with these reports, transient expression of an RSV subgroup. C viral envelope protein (EnvC) did not render either quail or human cells susceptible to infection by MLV (Tva).

Although EnvA is competent to hind receptor in the absence of processing by a host cell, proteolytic cleavage of EnvA is required for maximal fusogenic activity (Freed et al., 1989, J. Virol. 63:4670-4675; McCune et al., 1988, Cell 53:55-67; Perez et al., 1987, J. Virol. 61:160944). RSV having an envelope comprising a cleavage deficient form of EnvA, EnvA CL⁻, had a fusible titer between four and five orders of magnitude lower than wild type RSV. Human 293T cells which were transfected with a vector encoding EnvA CL⁻ were susceptible to fusion with MLV(Tva) at a titer roughly three orders of magnitude lower than the titer at which 293T cells were transfected with wild type EnvA.

Viral envelope proteins anchored by a glycosylphosphatidylinositol (GPI) moiety bind to their cognate cellular virus receptor proteins, but do not mediate fusion of the cell membrane with the viral envelope, and allow only partial mixing of cell membrane and viral envelope lipids (Gilbert et al., 1994, J. Virol. 68:5623-5628; Kemble et al., 1994, Cell 76:383-391; Melikyan et al., 1995, J. Cell Biol. 131:679-691; Salzwedel et al., 1993, J. Virol. 67:5279-5288; Weiss et al., 1993, J. Virol. 67:7060-7066), Consistent with these observations, cells transfected with a vector encoding the GPI anchored mutant of EnvA (EnvA GPI) were not susceptible to fusion with MLV(Tva).

Another mutant EnvA protein, EnvA A34[A]Q35, contains an insertion in the putative fusion peptide of RSV envelope which dramatically reduces EnvA mediated fusion. Consistent with this property, both quail and human cells which were contacted with a vector encoding EnvA A34[A]Q35 were susceptible to fusion with MLV(Tva), but the titer in each, cell line was roughly three orders of magnitude lower than the titer of the enveloped virus vector comprising wild type EnvA.

The results of these experiments which assessed the susceptibility to fusion with MLV(Tva) of human and quail cells transiently expressing various RSV viral envelope proteins and mutants thereof are summarized in Table 1 and as follows. The experiments demonstrated that the presence on a cell of a viral envelope protein to which a cellular virus receptor protein is cognate is a critical requirement for fusion of the cell with an enveloped virus vectors which comprises the cellular virus receptor protein. Fusion of cells comprising a viral envelope protein with an enveloped virus vector comprising a cognate cellular virus receptor protein is at least sometimes mediated by interaction between the viral envelope protein and the cognate cellular virus receptor protein.

Transiently transfected human and quail cells and RSV (A)-infected quail cells express high levels of EnvA. In order to determine whether cells which express a low level of EnvA would be as efficiently fused with MLV(Tva) as cells which express high levels, 3T3EnvA cells, a NIH3T3 cell line which stably expresses EnvA (Gilbert et al., 1994, J. Virol. 68:5623-5628), were employed. Fusion of 3T3EnvA cells with MLV (Tva) was also efficient, the titer ranging from about $2 \times 10^3$ to about $5 \times 10^3$ FU/ml. Furthermore, the titer of MLV(Tva) using 3T3EnvA cells can be increased 40-fold to about $2 \times 10^5$ FU/ml by concentrating the suspension of MLV(Tva) (Burns et al., 1993, Proc. Natl. Acad. Sci, U.S.A. 90:8033-8037). The results of these experiments demonstrate that a high surface density of viral envelope protein on the target cell is not a prerequisite for efficient fusion of the cell with an enveloped virus vector comprising a cognate cellular virus receptor protein.

RPMLV having an envelope comprising Tva*, a nonfunctional mutant of Tva, (hereinafter "MLV(Tva*)") was produced. The amino acid sequence of Tva* differs from that of Tva at five amino acid residues. These five amino acid sequence differences abrogate the ability of Tva to bind to EnvA in the viral envelope of RSV or to facilitate EnvA-mediated infection of cells by RSV. MLV(Tva*) was produced as described in this Example except that a vector encoding Tva* was used in place of the vector encoding Tva. Western blot analysis of MLV(Tva*) virions which were isolated as described herein revealed that Tva* was incorporated into MLV virions to approximately the same degree as that to which Tva was incorporated into MLV virions following transient transfection. MLV(Tva*) was unable to infect 3T3EnvA cells. These results demonstrate that Tva, the RSV cellular virus receptor incorporated into MLV(Tva), was responsible for the infectivity of MLV(Tva).

Figure 6A:
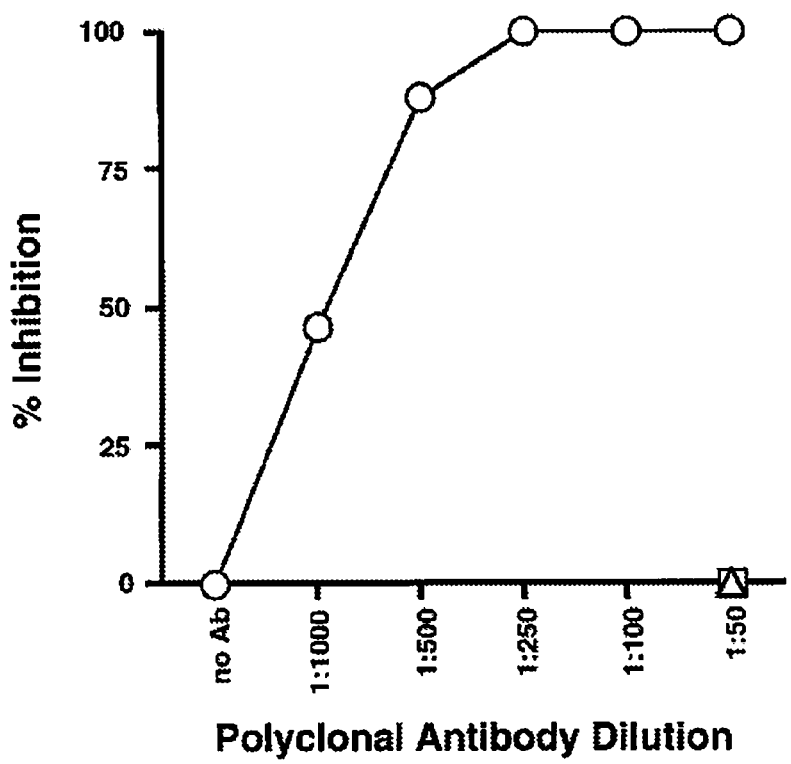
Figure 6B:
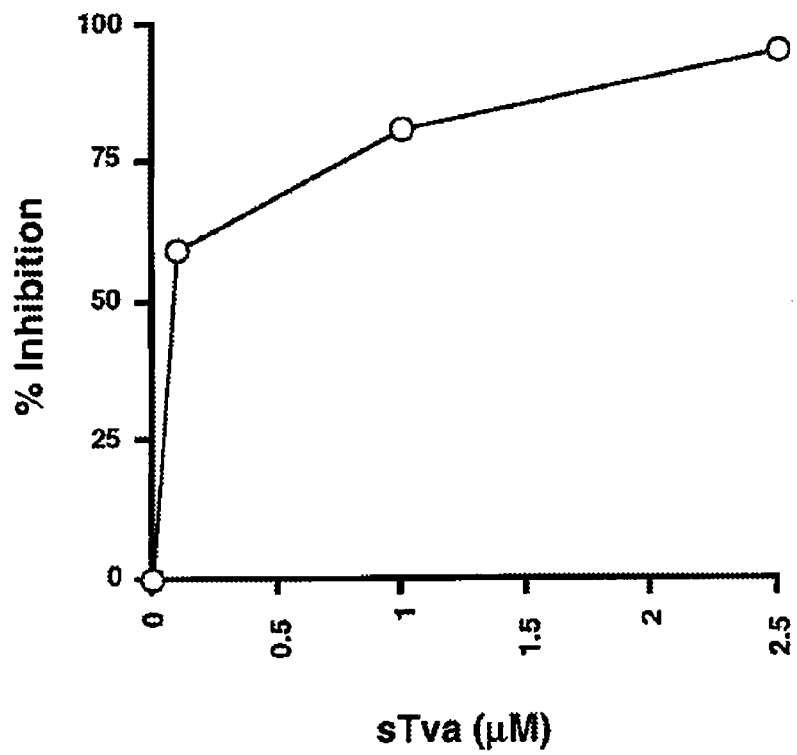

Anti-Tva rabbit polyclonal antiserum was raised using standard methods (see, e.g., Harlow et al., 1988, *Antibodies: A Laboratory Manual*, Cold Spring Harbor, N.Y.) which antiserum comprised antibodies which recognize and bind to Tva protein. MLV(Tva) was incubated with pre-selected dilutions of anti-Tva antiserum at 37° C. for thirty minutes. Following incubation of the mixture of a particular dilution of anti-Tva antiserum and MLV(Tva), 3T3EnvA cells were exposed to the mixture for four hours at 37° C. Following exposure of the 3T3EnvA cells to the mixture, the cells were washed twice with phosphate-buffered saline (PBS) and cultured in fresh medium comprising the same dilution of anti-Tva antiserum for forty-eight hours. The 3T3EnvA cells were then fixed and stained to detect β-galactosidase reporter gene expression. Percent inhibition of fusion was determined by comparing the proportion of cells having β-galactosidase activity to those not having such activity in two groups of cells: those treated with MLV(Tva) and those treated with MLV(Tva) which had been incubated with anti-Tva antisera. Fusion of 3T3EnvA cells with MLV(Tva) was inhibited in a dose-dependent manner by incubation of MLV(Tva) with anti-Tva antiserum (FIG. 6, Panel A).

In another experiment, 3T3EnvA cells were incubated for thirty minutes at 25° C. in medium comprising a pre-selected concentration of sTva, a soluble form of Tva RSV cellular virus receptor. Following incubation, the medium was removed and replaced with a second medium comprising the same concentration of sTva and MLV(Tva), and the 3T3EnvA cells were incubated in the second medium for four hours at 37° C. The cells were then washed twice with PBS and cultured in fresh medium for forty-eight hours. The 3T3EnvA cells were then fixed and stained to detect β-galactosidase reporter gene expression, an indicator of cell fusion with MLV(Tva). Percent inhibition of fusion was determined by comparing the proportion of cells having β-galactosidase activity to those not having such activity in two groups of cells: those treated with MLV(Tva) and those treated with MLV(Tva) after having been incubated with sTva. Fusion of 3T3EnvA cells with MLV(Tva) was inhibited by sTva in a competitive fashion when sTva was present in the medium before and during infection (FIG. 6, Panel B).

Taken together, the results obtained in experiments involving inhibition by anti-Tva antisera or by sTva of fusion of 3T3EnvA cells with MLV(Tva) demonstrate that the capacity of MLV(Tva) to fuse with cells comprising EnvA depends upon the presence in the envelope of MLV(Tva) of Tva.

RPMLV exhibits similar specificity and requirements for viral envelope protein and cellular virus receptor protein as RSV, except that the orientation of the proteins during binding and membrane fusion is reversed, the viral envelope protein being on the cell surface and the cellular virus receptor protein being on the surface of the viral particle. Furthermore, the fusible titers obtained using RPMLV are only one or two orders of magnitude lower than titer obtained using RSV or using Ebola viral envelope protein pseudotypes of MLV. The fact that infection of a host cell by RPMLV is efficient demonstrates that specific interaction between the viral envelope protein and core components of the virus is not required for uncoating of the virus and infection of the host cell.

The cellular MLV receptor, MCAT-1, is an amino acid transporter comprising multiple membrane-spanning domains and is structurally different from Tva (Albritton et al., 1989, Cell 57:659-666; Kim et al., 1991, Nature 352:725-728), A RPMLV comprising MCAT-1 was constructed and was designated MLV(MCAT).

MLV(MCAT) was made by cotransfecting 15 micrograms of each of three plasmids into $6 \times 10^6$ 293T cells overnight using $CaPO_4$ as described (Soneoka et al., 1995, Nucl. Acids Res. 23:628-633). The three plasmids used for co-transfection were plasmid pcDNA3 MCAT-1:Flu3, which comprises the gene encoding MCAT-1, plasmid pHit60, and plasmid pHit1.11. Thirty six hours post transfection, the medium in which the transfected cells were maintained was harvested and clarified by centrifugation at 2,300×g. Incorporation of MCAT-1 into MLV particles was confirmed by pelleting the particles by centrifuging a sample of the supernatant in an SW55 rotor for fifteen minutes at 55,000 rotations per minute in the presence of 30% (w/v) sucrose. Viral particles in the pellet were lysed using RIPA buffer, and the proteins therein were separated by 115% SDS-PAGE. The proteins which had been separated by PAGE were transferred to nitrocellulose and subjected to Western blot analysis using an anti-HA antibody, 12CA5, which specifically binds to MCAT-1 protein (see, e.g., Pelchen-Matthews et al., 1989, EMBO J. 8:3641-3649). Western blot analysis indicated that MCAT-1 had been incorporated into MLV particles. The supernatant was divided into aliquots, and the aliquots were stored at −80° C. until they were used for infection assays.

The ability of MLV(MCAT) to infect cells was evaluated using 293T cells which transiently expressed a fusion-competent form of MLV viral envelope protein. Titer of fusible units was in the range from about $10^3$ to about $10^4$ fusible units per milliliter. No fusion of cells and MLV(MCAT) was observed when mock transfected cells or 293T cells expressing either EnvA protein or amphotropic MLV viral envelope protein were used. These results demonstrate that MCAT-1 directs fusion of an enveloped virus vector comprising MCAT-1 specifically with cells which express MLV viral envelope protein. Furthermore, the specificity observed between MLV viral envelope protein and MCAT-1 is retained when the viral envelope protein is present in the membrane of a cell and cellular virus receptor protein is present in the envelope of an enveloped virus vector.

The results presented herein demonstrate that a cell which comprises a viral envelope protein are susceptible to fusion with an enveloped virus vector comprising a cognate cellular virus receptor protein. The results herein also demonstrate that the interaction between the cell and the vector is mediated by the interaction between the viral envelope protein and the cognate cellular virus receptor protein. To the extent that properties of the cell or of the vector or both do not interfere with the interaction between the viral envelope protein and the cognate cellular virus receptor protein, those properties may be varied. These results demonstrate that cellular membrane receptors can be incorporated into virions and retain their structural integrity as measured by functional ability to mediate fusion.

Example 3

Use of Virus Particles Comprising Host Cell Surface Protein to Assay Protein-Protein Interaction The HIV envelope (Env) protein mediates entry into cells by binding CD4 and an appropriate coreceptor, which triggers structural changes in Env that lead to fusion between the viral and cellular membranes. The major HIV-1 coreceptors are the seven transmembrane domain chemokine receptors CCR5 and CXCR4. The type of coreceptor used by a virus strain is an important determinant of viral tropism and pathogenesis, and virus-receptor interactions can be therapeutic targets. However, Envs from many virus strains interact with CXCR4 and CCR5 with low affinity such that direct study of this important interaction is difficult if not impossible using standard cell-surface binding techniques.

The data disclosed herein demonstrate a novel approach that makes it possible to study ligand binding to membrane proteins, including Env-coreceptor interactions, using a microfluidic device that detects intramolecular interactions—otherwise known as an optical biosensor. CCR5, CXCR4, and other membrane proteins were incorporated into retrovirus particles, which were purified and attached to the biosensor surface. Binding of conformationally sensitive antibodies as well as Env to these receptors was readily detected, demonstrating that the incorporated proteins retained their native structures. The equilibrium dissociation constant for the interaction between an Env derived from the prototype HIV-1 strain IIIB for CXCR4 was approximately 500 nM, explaining the difficulty in measuring this interaction using standard equilibrium binding techniques. Retroviral pseudotypes represent easily produced, stable, homogenous structures that can be used to present a wide array of single and multiple membrane-spanning proteins in a native lipid environment for biosensor studies, thus avoiding the need for detergent solubilization, purification, and reconstitution. The approach should have general applicability and can be used to correlate Env-receptor binding constants to viral tropism and pathogenesis.

The data disclosed herein demonstrate the development of a novel technique to study ligand binding to both topologically simple and complex transmembrane proteins using the optical biosensor by presenting these proteins on the surface of retroviral particles. The data disclosed herein demonstrate that a number of single-spanning proteins and 7™ domain chemokine receptors can be incorporated into virions, which can be easily purified and attached to the biosensor surface. Binding of antibodies and HIV-1 gp120 to these receptors exhibited appropriate specificity, and structural integrity of the receptors was maintained. Binding of a small-molecule inhibitor (ALX40-4C) was demonstrated by virtue of its ability to inhibit gp120 binding. The use of these retroviral pseudotypes in the optical biosensor eliminates the need to purify and reconstitute membrane proteins for ligand binding studies and provides a general experimental technique to characterize functionally important interactions with membrane proteins that would otherwise not be possible with standard equilibrium binding assays.

The materials and methods of this Example are as follows.

Proteins

HIV-1 HXBc2 and 8×gp120 were produced and purified by lectin chromatography (Hoffman et al., 1999, Proc. Natl. Acad. Sci. USA 96:6359-6364). The anti-gp120 mAb 17b was provided by J. Robinson (Tulane University, New Orleans) (Thali et al., 1993, J. Virol. 67:3978-3988 and Kwong et al., 1998, Nature (London) 393:648-659). mAbs CTC8 and #549 to CCR5 and mAbs R&D#8 and R&D#16 were provided by M. Tsang (R & D Systems) (Lee et al., 1999, J. Biol. Chem. 274:9617-9626). mAbs 4G10 and 7C11.1 to CXCR4 were a gift of C. Broder (Uniformed Services University of the Health Sciences, Bethesda) (Chabot et al., 2000 J. Virol. 74:4404-4413), anti-CXCR4 mAb 12G5 was described in Endres et al. (1996, Cell 87:745-756), and anti-CCR5 mAb 2D7 was from Research Diagnostics (Flanders, N.J.). ALX40-4C, a specific peptide inhibitor of CXCR4, was provided by Allelix (Salt Lake City). (Doranz et al., 1997, J. Exp. Med. 186:1395-1400). The murine antibody 9E10 was used for detection of the myc epitope (Evan et al., 1985, Mol. Cell, Biol. 5:3610-3616). Chick collapsin-1 containing a histidine tail was purified via nickel column chromatography (Koppel et al., 1997, Neuron 19:531-537).

Pseudotype Production, Purification, and Characterization

Murine leukemia virus (MLV) pseudotypes were produced by calcium phosphate-mediated transfection of 293T cells in 225-cm$^2$ flasks with a 3:1 ratio of receptor plasmid to pCGP, which encodes the MLV gag and pol genes. Four hours posttransfection, fresh media supplemented with 10 mM n-butyric acid was added to increase protein expression. 48 hours posttransfection, supernatant was harvested, and cell debris was removed by low speed centrifugation and 0.45 µm filtration. The supernatant was pelleted for 90 minutes in an SW28 rotor at 28,000 RPM through 20% sucrose/PBS and resuspended overnight in PBS. A second ultracentrifugation step through 20% sucrose/PBS was per-formed in an SW40 rotor at 40,000 RPM for 45 minutes, and the pellet was resuspended in 100 µl of 10 mM Hepes, pH 7.4. The pseudotypes were either stored at 4° C. or aliquoted and frozen at −20° C. MLV pseudotypes were analyzed for MLV gag and receptor expression by SDS-PAGE and Western blot. Pseudotypes were also analyzed by equilibrium density gradient ultracentrifugation using a 15-45% sucrose gradient at 35,000 RPM for 16 hours in a SW40 rotor. Particles were also examined by negative stain electron microscopy on carbon films after staining with uranyl acetate.

Attachment of Lipoparticles to Biosensor Surfaces

All attachments were performed in PBS running buffer using Bia2000 or BiaX optical biosensors (Biacore, Uppsala, Sweden) at 25° C. Lipoparticles, also referred to herein as "pseudotypes," were attached to a gold surface derivatized with a carboxylated alkane thiol (Biacore C1 chip) or a short carboxy-dextran matrix (Biacore F1 chip) following a 10-min activation of surface carboxyl groups using a 1:1 mixture of 1-ethyl-3-(3-dimethylaminopropyl)carbodiimide hydrochloride (EDC) (1 M) and N-hydroxysuccinimide (0.25 M) at 5 µl/min. Pseudotypes that had been mixed 1:1 with 0.1 M sodium acetate, pH 5.5, were injected manually until the desired level of response units (RU), usually between 2,000 and 6,000 RU, had been reached. Following attachment, the remaining surface carboxyl groups were quenched with 35 μl of 1 M ethanolamine, pH 8.5, at 5 μl/min.

Binding Experiments

Binding experiments were performed in DMEM with 0.1% Pluronic F127 (Sigma) or PBS without surfactants at 30 and at 25° C. unless otherwise noted. Importantly, every binding experiment performed included a reference surface containing an equivalent RU amount of MLV particles made with pcDNA3 or other receptor as a negative control. Analyte was removed following each binding interaction using duplicate 20-μl pulses of regeneration solution at 100 μl/min. Regeneration conditions varied for each ligand analyte pair and were optimized empirically to remove all bound protein and maintain surface activity using various combinations of pH 5 (0.15 M oxalic acid/0.15 $MH_3PO_4$/0.15 M formic acid/0.15 M malonic acid, pH 5), pH 9 (0.2 M ethanolamine/0.2 M $Na_3PO_4$/0.2 M glycine/0.2 M piperazine, pH 9), 1 M NaCl, 1 M $MgCl_2$, and chaotropic (0.46 M KCSN/1.83 M $MgCl_2$/0.92 M urea/L83 M guanidine HCl) solutions (Andersson et al., 1999, Anal. Chem. 71:2475-2481). Data analysis and fitting was performed with BIAEVALUATION 3.0 software.

The Results of the experiments disclosed in this example are as follows.

Receptor Incorporation and Characterization of MLV Lipoparticles

Figure 8:
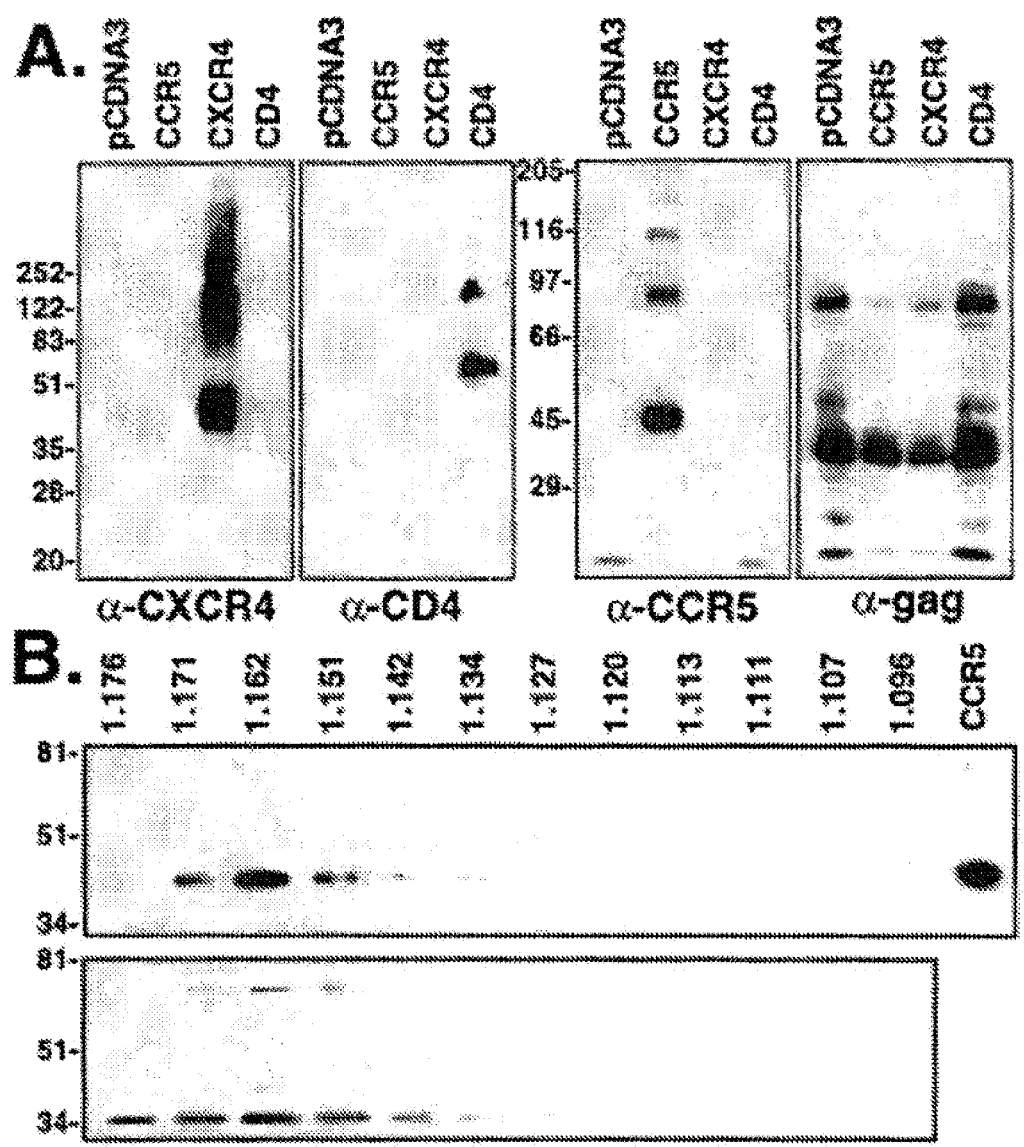
FIG. 8, comprising

Retroviruses can nonspecifically incorporate cell-surface membrane proteins into their lipid envelope as they bud from the plasma membrane (Young et al., 1990, Science 250:1421-1423, Balliet et al., 1998, J. Virol. 72:671-676 and Suomalainen et al., 1994, J. Virol. 68:4879-4889). To determine whether retroviral pseudotypes could be used to present membrane proteins in their native conformations for optical biosensor studies, different transmembrane proteins were transiently coexpressed with the structural proteins necessary to generate MLV particles in 293T cells. The media were collected, and virus particles were purified by ultracentrifugation and analyzed for the presence of the viral core protein (gag) and the desired membrane protein. The type I membrane protein CD4 and the 7TM chemokine receptors CCR5 and CXCR4 were incorporated into virus particles at readily detectable levels (FIG. 8A). The virus particles were judged pure by equilibrium gradient centrifugation (FIG. 8B) and negative stain electron microscopy, which revealed a homogenous population of vesicular structures with an average diameter of 105±29 nm.

Immobilization of MLV Lipoparticles to Biosensor Surfaces

To perform binding studies using the purified receptor-bearing MLV lipoparticles, virions were captured on a derivatized gold surface suitable for use in a Biacore optical biosensor. A number of sensor surfaces are available from Biacore, each with different surface properties. A standard coupling chemistry technique was used in which sensor surface carboxyl groups are activated with N-hydroxysuccinimide/EDC, permitting subsequent formation of covalent bonds with primary amines on the virion surface. The most frequently used sensor chip (CM5) contains a; 100 nM dextran hydrogel derivatized with carboxyl groups (Myszka et al., 1999 J. Mol. Recognit. 12:390-408).

Because viral particles are likely to be negatively charged and surface plasmon resonance decays exponentially as a function of distance from the biosensor surface, a carboxymethylated surface that lacks a dextran matrix (Biacore C1 chip) was used. About 4,000-6,000 RU of virus particles were reliably attached to the C1 chip but it was difficult to obtain robust attachment of MLV particles onto the CM5 surface. However, suitable attachment (4,000-6,000 RU) could be obtained on a sensor chip with a shorter dextran surface (Biacore F1 chip). The optimal pH for attachment of the pseudotypes was 5.5 for all surfaces and receptors. Following attachment, reductions in baseline were not observed with time or repeated regeneration, indicating that the particles were irreversibly linked to the sensor surface.

Antibody Binding Studies to MLV Lipoparticles Containing Chemokine Receptors.

Figure 9:
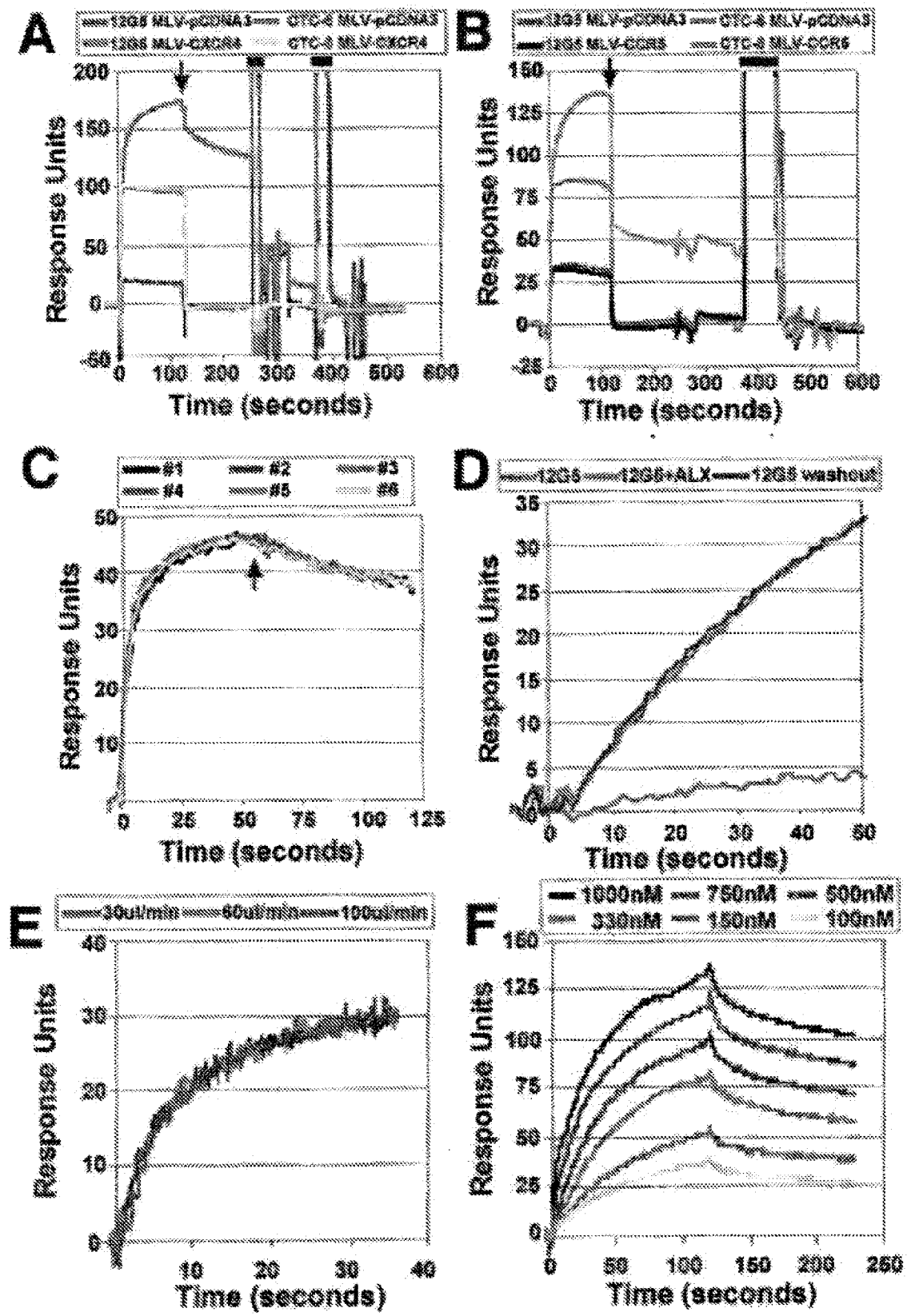
FIG. 9, comprising
Figure 10:
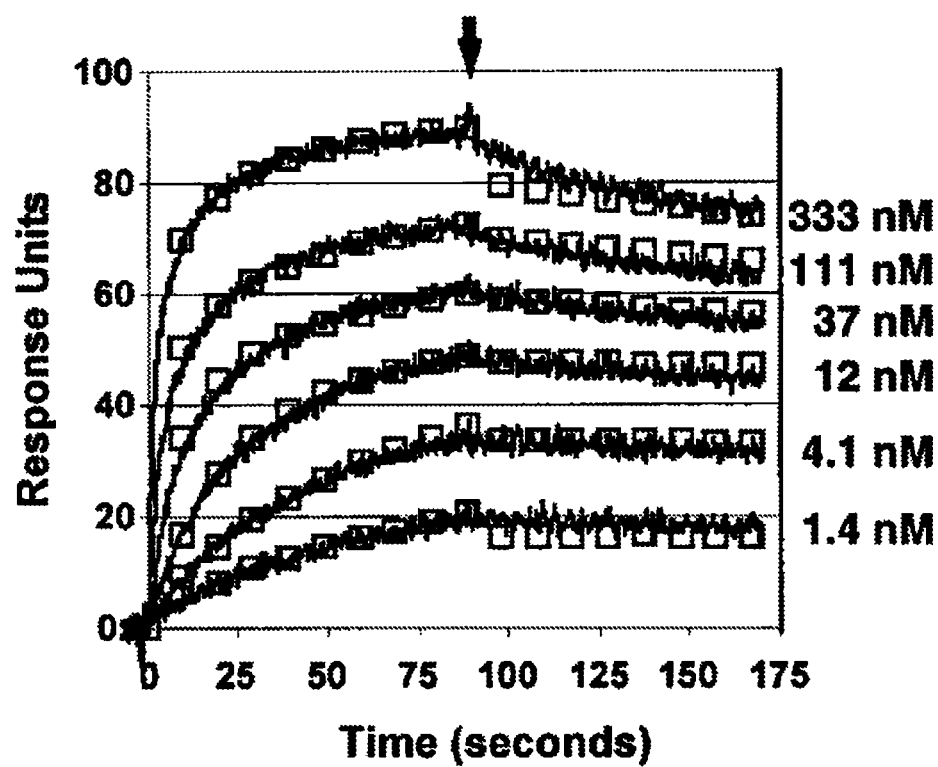
FIG. 10, is a graph depicting bivalent binding of 12G5 to MLV-CXCR4. Sensorgrams of 12G5 binding to MLV-CXCR4 are shown at different mAb concentrations, with the signals obtained from 12G5 binding to the MLV-pcDNA3 surface being subtracted. Binding was measured for 90 s and dissociation for 80 s before regeneration. Global analysis of the data using Biaevaluation 3.0 software was performed, and the boxes indicate the best fit of the data to a bimolecular interaction.

Equivalent amounts of MLV particles containing CCR5 (MLV-CCR5), CXCR4 (MLV-CXCR4), or no receptor (MLV-pcDNA3) were attached to the biosensor surface, and binding of specific antibodies was measured. The anti-CXCR4 antibody 12G5, which recognizes a conformational epitope in CXCR4 (Doranz et al., 1999, J. Virol. 73:2752-2761 and Brelot et al., 1997, J. Virol. 71:4744-4751), bound to MLV-CXCR4 and did not bind to MLV-CCR5 or MLV-pcDNA3 (FIG. 9A). The anti. CCR5 antibody CTC8, which recognizes a linear epitope on the N terminus of CCR5 (Lee et al., 1999, J. Biol. Chem. 274:9617-9626), bound to MLV-CCR5 and did not bind to MLV-pcDNA3 or MLV-CXCR4 (FIG. 9B). When PBS was washed across the sensor surface following injection of the antibodies, a typical dissociation curve was observed (arrows in FIGS. 9 A and B). Similar results were obtained with CCR5 mAbs #549 and 2D7 and CXCR4 mAbs 4G10, R&D#8, and R&D#16 to both linear and conformational epitopes. Mouse IgG and BSA showed minimal binding to any of the MLV particles on the F1 or C1 chips.

For retroviral lipoparticles to be successful vehicles for presenting membrane proteins on a biosensor surface, they should withstand multiple regeneration cycles in which bound analytes are removed without damaging either the particles or the receptors they contain. In this way, multiple binding experiments can be performed with a single surface, a prerequisite for the accurate determination of binding constants. The data disclosed herein demonstrate that a brief pulse with a regeneration mixture containing an equal proportion of pH5 and chaotropic solutions (Andersson et al., 1999, Anal. Chem. 71:2475-2481) efficiently removed 12G5 from MLV-CXCR4 particles, returning the signal to baseline (FIG. 9A, bars). A single injection of this regeneration buffer was also sufficient to remove CTC8 from MLV-CCR5 particles, again returning the signal to baseline (FIG. 9B, bar). Similar results were obtained with other CCR5 and CXCR4 antibodies.

The reproducibility and stability of the MLV particles to multiple binding and regeneration cycles is shown in FIG. 9C. Overlay plots from six sequential binding reactions on the same biosensor surface performed with 12G5 were virtually identical. Results with CTC8 were similar. These results indicate that the regeneration conditions removed antibody from the surface without damaging the MLV particles or altering receptor conformation. In fact, binding experiments were performed over the course of several days before significant decreases in the binding capacity of the MLV particles was observed on a given sensor chip. In addition, MLV particles were stored at −20° C. for at least several weeks before attachment and use in biosensor experiments.

As an additional specificity control, the ability of ALX40-4C, a small peptide inhibitor of CXCR4, to block 12G5 binding to MLV-CXCR4 particles (Doranz et al., 1997, J. Exp. Med. 186:1395-1400), was assessed. As shown in FIG. 9D, inclusion of ALX40-4C in the running buffer eliminated 12G5 binding to MLV-CXCR4 at a concentration (4 mM) similar to that needed to inhibit HIV-1 infection (Doranz et al., 1997, J. Exp. Med. 186:1395-1400). Furthermore, ALX40-4C could be washed out and full binding of 12G5 to MLV-CXCR4 restored (FIG. 9D). The ability of CTC8 to bind MLV-CCR5 was unaffected by the presence of ALX40-4C. The reversible ability of ALX40-4C to specifically prevent 12G5 binding to MLV-CXCR4 confirms the specificity of the lipoparticle system and also shows that this approach can be used to monitor binding of small molecules to membrane incorporated receptors.

Having shown that antibody binding to chemokine receptors on MLV pseudotypes was specific and highly reproducible, a series of experiments was performed to assess the kinetic constants of these interactions. Binding of 12G5 to CXCR4 particles at different flow rates ensured that ligand binding to the MLV particles was not diffusion-limited (FIG. 9E). Results were similar for CTC8 and other anti-CCR5 and anti-CXCR4 anti-bodies. Next, the binding of the mAbs CTC8 and 12G5 to the chemokine receptors CCR5 and CXCR4 was measured using a range of antibody concentrations (FIGS. 9F and 3), and the data were analyzed using BIAEVALUATION 3.0 software. Analysis of the binding curves for 12G5 indicated that the data were consistent with a bivalent interaction ($X^2$ 3.0 for 12G5 using the bivalent model with $R_{max}$ 88) but not with a 1:1 interaction ($X^2$ 36 for the same data analyzed by the 1:1 model).

These results are consistent with each 12G5 antibody binding two CXCR4 receptors on the MLV particle. Similar fitting results were obtained with CTC8 (FIG. 2F) and other anti-CCR5 and anti-CXCR4 antibodies. Because antibody binding to the chemokine receptors was bivalent, this will result in a higher apparent affinity, and the kinetics cannot be described with a simple interaction model. Thus, to accurately measure antibody-receptor binding constants using this technique, Fab fragments can be used (Myszka et al., 1999, J. Mol. Recognit. 12:279-284).

Binding Studies of HIV-1 gp120 to MLV Pseudotypes.

Direct binding of X4 gp120 proteins to CXCR4 has been difficult to measure (Doranz et al., 1999, J. Virol. 73:2752-2761). In addition, without wishing to be bound by any particular theory and although binding of gp120 subunits derived from R5X4 virus strains to CD4 can be easily detected, binding of these proteins to CCR5, CXCR4, or other coreceptors cannot, perhaps due to low affinity interactions (Doranz et al., 1999, J. Virol. 73:2752-2761, Baik et al., 1999, Virology 259:267-273 and Etemad-Moghadam et al., 2000, J. Virol. 74:4433-4440). It was reasoned that the real-time nature of the biosensor would make it possible to measure gp120-CXCR4 interactions more readily than traditional binding methods that rely on steady-state measurements. To simplify the binding interaction, a gp120 from a CD4-independent strain of HIV-1 termed 8×, which interacts directly with CXCR4 (Hoffman et al., 1999, Proc. Natl. Acad. Sci. USA 96:6359-6364), was used.

Figure 11:
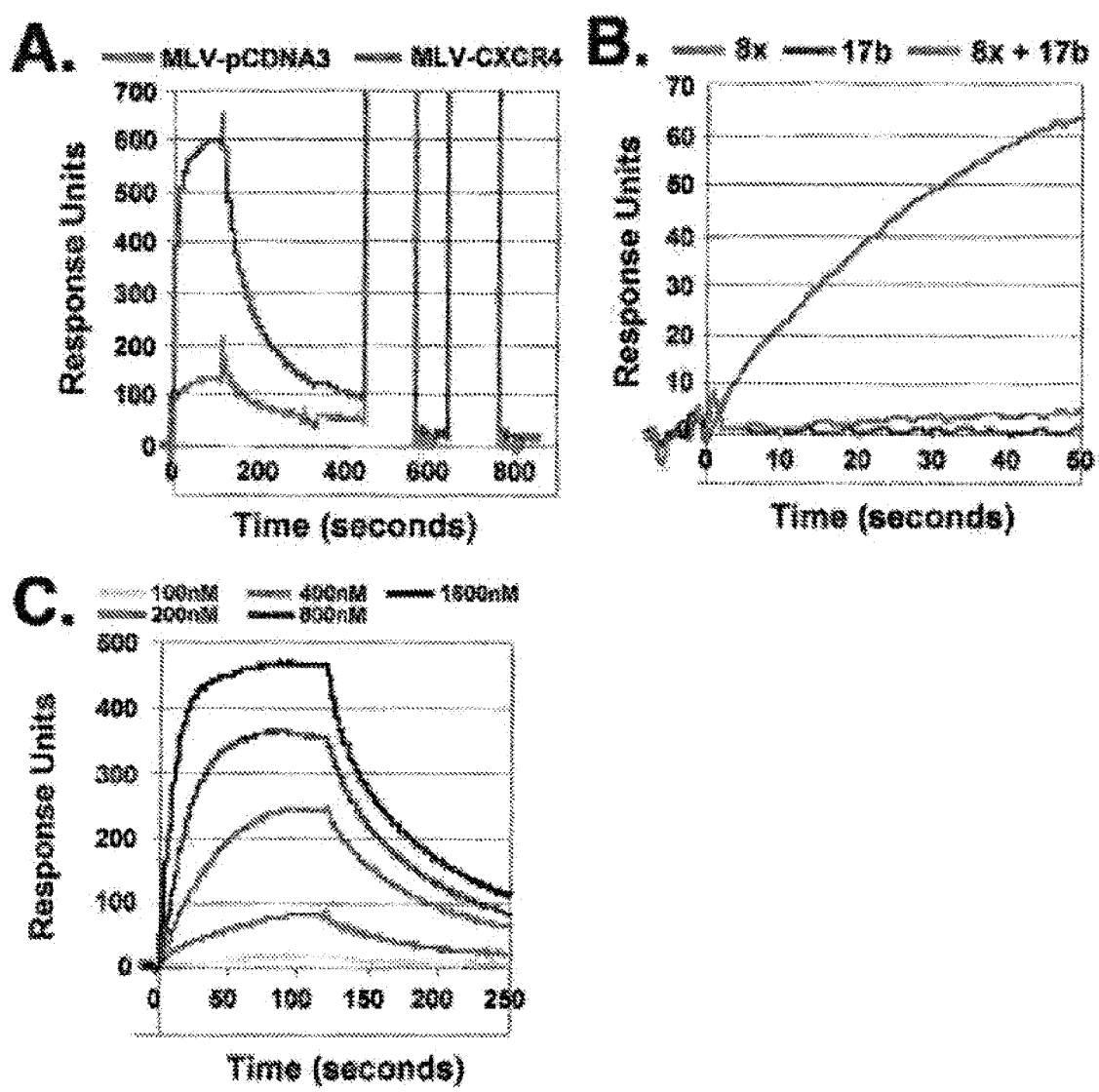
FIG. 11, comprising
Figure 12:
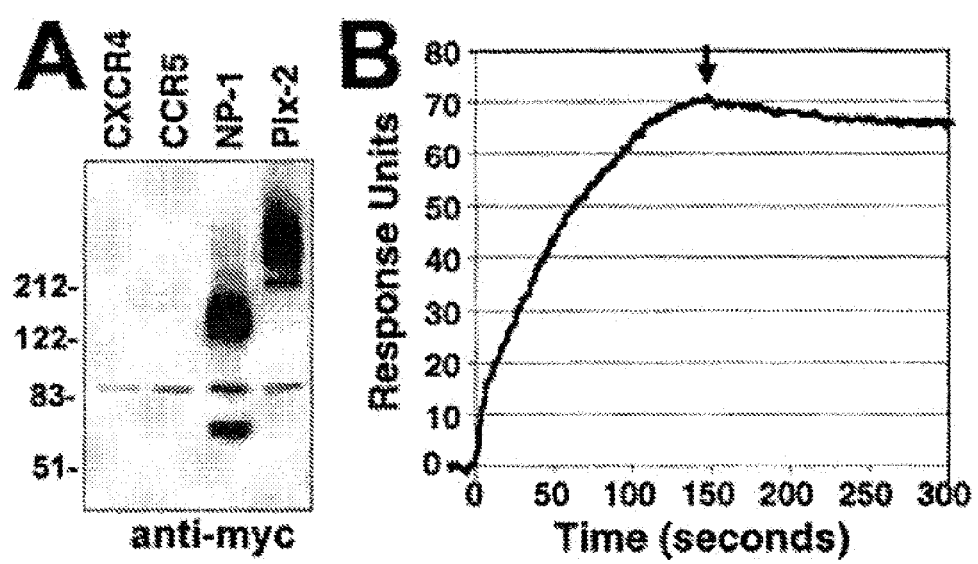
FIG. 12, comprising

Initial attempts to measure specific 8×gp120 binding to MLV-CXCR4 on a C1 chip in PBS running buffer were unsuccessful due to nonspecific binding associated with this highly glycosylated protein to the control surface. When the running buffer was changed from PBS to DMEM with 0.1% Pluronic F127, a surfactant previously shown to decrease the nonspecific binding of proteins to gold surfaces (Green et al., 1998, J. Biomed. Mater. Res. 42:165-471), specific binding of 8× to MLV-CXCR4 compared with MLV-pcDNA3 was detected (FIG. 11A). Binding of 8× could be prevented by the 17b antibody, which binds to the coreceptor binding site in gp120 (Kwong et al., 1998, Nature 393:648-659), confirming the specificity of this interaction (FIG. 12B). Similar results were obtained when binding studies were performed with 8× in PBS running buffer without Pluronic F127 on an F1 chip, which reduced, but did not completely eliminate, the nonspecific binding of Env.

Regeneration conditions (pH 5/chaotropic solution) used to remove 12G5 and other anti-CXCR4 antibodies also proved to be successful for stripping gp120 from MLV-CXCR4 (FIG. 11A). Multiple binding and regeneration cycles of 8× indicated that there was approximately a 2% loss in subtracted signal with each Env binding interaction. Without wishing to be bound by any particular theory, this may be related to irreversible removal of lipoparticles from the surface such as by lysis of the lipid membrane, inactivation of CXCR4 conformations involved in Env binding, or incomplete removal of Env from the sensor surface following regeneration.

When dose-response experiments with 8×gp120 were performed (FIG. 11C), the equilibrium dissociation constant was calculated to be 506±nM (from five independent experiments). The fast off-rate exhibited by 8×gp120 helps explain the difficulty experienced in measuring this interaction using standard equilibrium cell-surface binding assays, as all or most of the gp120 dissociates from CXCR4 by the time the washing steps are complete. Finally, the data disclosed herein demonstrate that specific binding of a CD4-dependent gp120 from the HXB strain of HIV-1 to MLV-CXCR4 was detected, but only when soluble CD4 was included in the running buffer so as to trigger the conformational changes in gp120 needed for coreceptor binding, further demonstrating that the lipoparticle construct preserves the biological structure and function of the protein embedded in the lipid bilayer of the construct.

Binding Studies with Other Membrane Proteins.

Having established retroviral pseudotyping as a way to construct lipoparticles in order to study binding interactions with a biosensor, we determined whether binding to other membrane proteins could be measured with this technique. Neuropilin-1 (NP-1) is a member of a related group of type 1 membrane proteins involved in axonal guidance in the developing nervous system. A family of protein ligands, termed collapsins, binds to NP-1 receptors on axons and triggers axonal repulsion and redirection (He et al., 1997, Cell 90:739-751). After determining that NP-1 and a similar protein, plexin-2, could be incorporated into MLV particles (FIG. 12A), we attached MLV-NP-1 to a biosensor surface and measured binding of collapsin-1. As shown in FIG. 12B, collapsin-1 specifically interacted with MLV-NP-1. These results indicate that a diverse group of membrane proteins can be incorporated and presented in MLV particles for binding studies in the optical biosensor.

Optical biosensor technology can be used to study molecular interactions in real time, making it possible to accurately measure kinetic and equilibrium binding constants (Canziani et al., 1999, Methods 19:253-269 and Rich et al., 2000, Curr. Opin. Biotechnol. 11:54-61). Whereas interactions between soluble molecules can be routinely measured, it has not been possible to present membrane proteins in their native, lipid environments on the sensor surface for a number of technical reasons. These problems can sometimes be circumvented by generating soluble ectodomain fragments of type and type II integral membrane proteins, but proteins that span the membrane multiple times or that exist as multimeric complexes are not as easily manipulated.

In principle, integral membrane proteins can be purified and reconstituted into artificial membranes that can be attached to the sensor surface. However, purification and reconstitution of membrane proteins is a laborious and empirically driven process, and thus far it has not been used successfully in an optical biosensor format with the exception of bacterial rhodopsin (Salmon et al., 1994, Biochemistry 33:13706-13711). As a result, entire classes of membrane proteins, such as seven transmembrane domain receptors, have not been studied using this technique. In the case of HIV, there are many instances in which standard equilibrium binding assays are not sufficiently sensitive to study in detail, or sometimes even detect, interactions between the viral Env protein and its 7™ coreceptors (Doranz et al., 1999, J. Virol. 73:2752-2761, Baik et al., 1999, Virology 259:267-273 and Etemad-Moghadam et al., 2000, J. Virol. 74:4433-4440).

Because HIV-coreceptor interactions are critically important determinants of viral tropism and pathogenesis, and because these receptors are important drug targets (Berger et al., 1999 Annu. Rev. Immunol. 17:657-700), this is a significant shortcoming. Therefore, lipoparticles were produced by taking advantage of the fact that retroviruses can incorporate cellular membrane proteins into their lipid envelopes during the process of budding from the cell surface. In effect, retroviral pseudotypes serve as model membrane vesicles that, due to the presence of the viral core, are homogeneous in size, easily purified, and stable. In addition, incorporation of a membrane protein into a retrovirus avoids the need for detergent solubilization, purification, and reconstitution. A significant number of cellular membrane proteins can be incorporated into retroviral pseudotypes, indicating that the approach described here should be broadly applicable.

A host of type I, type II, and multiple membrane-spanning cellular membrane proteins have been previously shown to be incorporated into retrovirus particles, including class I and class II MHC proteins, CD4, various ICAMs, a tetraspan protein (CD63), as well as multiple membrane-spanning proteins such as the murine cationic amino acid transporter, which functions as a receptor for the ecotropic murine leukemia virus (see, e.g., Balliet & Bates, 1998, J. Virol. 72:671-676, and references cited therein). For this approach to work in the optical biosensor format, the incorporated membrane proteins must retain their native conformation as has been demonstrated using the lipoparticles disclosed herein.

Studies in which viral receptors are incorporated into retroviral particles, enabling these particles to infect cells expressing the cognate viral Env glycoproteins, demonstrate this. For example, incorporation of CD4 and either CCR5 or CXCR4 into virus particles enables these virions to infect cells expressing R5 or X4 HIV-1 Env proteins, respectively (Endres et al., 1997, Science 278:1462-1464 and Schnell et al., 1997, Cell 90:849-857). Because the determinants on CD4 and CCR5 recognized by the viral Env protein are conformationally complex (Hoffman et al., 1998, AIDS 12, Suppl. A, S17-S26), these results indicate that the pseudotyped receptors retain their native conformation. In addition, this shows that at least two different proteins can be incorporated into a given virus particle (e.g., hetero or homo-oligomer complexes); it also shows that because membrane fusion is a cooperative process requiring multiple receptor binding events (Hernandez et al., 1996, Annu. Rev. Cell Dev. Biol. 12:627-661), multiple copies of each can be incorporated. In the case of HIV-1, it is estimated that six CCR5 molecules are needed to support membrane fusion (Kuhmann et al., 2000 J. Virol. 74:7005-7015) and that multiple CD4 molecules are also needed (Layne et al., 1990, Nature 346:277-279). The data disclosed herein support these conclusions in that the 7™ and type I membrane proteins studied herein retained their native conformations as judged by their abilities to bind a variety of conformationally sensitive ligands. The presence of bivalent interactions also suggests that there is lateral mobility in the retroviral membrane, providing further evidence that they are a good cell-surface surrogate.

The efficiency with which a protein can be pseudotyped into a virus particle can be influenced by the location and degree of expression and the nature of the cytoplasmic domain of the protein (Young et al., 1990, Science 250:1421-1423; Suomalainen et al., 1994, J. Virol. 68:4879-4889; Suomalainen et al., 1994, J. Virol. 68:4879-4889; and Henriksson et al., 2000, J. Virol. 73:9294-9302). A prerequisite for pseudotype formation with MLV is that the protein of interest be expressed on the cell membrane from which the virus buds. Potentially, viruses that bud from intracellular compartments can be used to incorporate cellular membranes that reside elsewhere in the cell. Alternatively, proteins retained in intracellular organelles can be retargeted to the cell surface and incorporated into, for instance, MLV particles by modifying retention or targeting motifs.

There is increasing evidence that some viruses selectively bud from the cell surface through detergent-insoluble lipid rafts (Nguyen et al., 2000, J. Virol. 74:3264-3272; Zhang et al., 2000, J. Virol. 74:4634-4644). Therefore, targeting proteins of interest to lipid rafts could, for some virus types, improve pseudotype formation. Once the protein is expressed at the proper location on the cell surface, incorporation efficiency is likely to be related to expression levels. Because high level expression is desirable, a transient expression system using a cell type that is easily transfectable as well as being capable of high levels of protein production was used. In excess of 100,000 CCR5 and CXCR4 molecules are expressed per cell using this approach (Lee et al., 1999, J. Biol. Chem. 274:9617-9626).

Lipoparticle formation can be improved by constructing chimeric molecules in which the cytoplasmic domain of a membrane protein is replaced with that of the retroviral Env protein, or any tag that links the surface molecule to the structural proteins of the virus (gag). Shortening a long cytoplasmic region can also improve protein incorporation into viral pseudotypes by reducing negative interactions between bulky cytoplasmic domains and retroviral gag protein (Henriksson et al., 2000, J. Virol. 73:9294-9302). A final factor to consider is the type of virus used. In addition to MLV, other viruses such as vesicular stomatitis virus, RSV, rabies viruses, and HIV can also be used to generate pseudotypes, providing additional options for packaging cellular membrane proteins into virus particles (Endres et al., 1997, Science 278:1462-1464 and Schnell et al., 1997, Cell 90:849-857).

The use of retroviral pseudotypes as membrane presentation vehicles, i.e., lipoparticles, will make it possible to study ligand interactions with many different cellular membrane proteins using microfluidic devices in general and optical biosensors in particular. This approach has important implications for drug discovery in which binding of small molecules to 7™ and other membrane receptors can be measured. The data disclosed herein demonstrate attachment of 4,000 to 6,000 RUs of virus particles allowed several hundred RUs of specific antibody binding to be obtained. This is considerably in excess of what is needed to obtain accurate kinetic measurements, as accurate responses can be measured well below 100 RU, and even below 10 RU in some cases (Myszka et al., 1999, J. Mol. Recognit. 12:279-284). Thus, the number of lipoparticles that should be bound to the sensor surface can be readily assessed and modified as required pursuant to the teachings provided herein or as would be understood by the skilled artisan armed with the teachings of the invention.

It has been demonstrated that it is possible to detect binding of low mass compounds using an optical biosensor (Markgren et al., 1999, Anal. Biochem. 265:340-350 and Strandh et al., 1998, J. Mol. Recognit. 11:188-190). Because the signal measured by the optical biosensor is proportional to mass, it is likely that improved attachment of retroviral pseudotypes will be needed to measure binding of small molecular weight compounds. Attachment of larger amounts of pseudotypes should be possible because the data disclosed herein demonstrates that the binding capacity of the surfaces used herein was low so as to minimize mass transport effects that could be associated with the high molecular weight ligands that were used herein (Myszka et al., 1999, J. Mol. Recognit. 12:279-284). It will be apparent to one skilled in the art based upon the disclosure provided herein, that an increase in signal (RU) can be readily obtained by increasing the number of receptors on each lipoparticle and/or by increasing the number of lipoparticles on the surface of a biosensor.

The ability to measure binding of small molecules to membrane receptors with an optical biosensor could make this a useful screening tool. Advantages of this approach include the fact that only a small amount of sample is needed and that the ligand does not have to be labeled. The ability of many compounds to bind a given receptor could be rapidly screened, making it possible to identify compounds with desirable association and dissociation kinetics, information not normally available from other screening methods. In the case of HIV-1, this approach should make it possible to directly measure some Env-receptor interactions, providing information on the relationship between Env-receptor affinity and viral tropism and pathogenesis, and also on how small molecule inhibitors interact with the major HIV coreceptors and block Env binding and viral infection.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of producing an antibody that binds to a multiple membrane spanning protein, the method comprising:

administering a virus-like particle comprising an enveloped virus core and a heterologous multiple membrane spanning protein to an animal under conditions to produce the antibody that binds to the heterologous membrane spanning protein; and isolating the antibody that binds to the heterologous multiple membrane spanning protein.

2. The method of claim 1, wherein the antibody is a monoclonal antibody.

3. The method of claim 1, wherein said heterologous multiple membrane spanning protein is capable of binding with a ligand under conditions wherein said ligand would bind with an otherwise identical protein present on a cell membrane.

4. The method of claim 1, wherein the enveloped virus core of the isolated virus-like particle is derived from a retrovirus.

5. The method of claim 1, wherein said enveloped virus core is selected from the group consisting of a murine leukemia virus, a human immunodeficiency virus, a rabies virus, a Rous sarcoma virus, and a vesicular stomatitis virus.

6. The method of claim 1, wherein the heterologous multiple membrane spanning protein is selected from the group consisting of a G-protein coupled receptor, a transporter protein, and an ion channel protein.

7. The method of claim 1, wherein said heterologous multiple membrane spanning protein is selected from the group consisting of CCR5, CXCR4, MCAT-1, CXCR2, CXCR3, mu-opoid receptor, and KCNH2 potassium channel protein.

8. The method of claim 1, wherein said heterologous multiple membrane spanning protein is a chemokine receptor.

9. The method of claim 1, wherein said heterologous multiple membrane spanning protein is an amino acid transporter.

10. The method of claim 1, wherein said heterologous multiple membrane spanning protein is a virus receptor protein.

11. The method of claim 1, wherein said heterologous multiple membrane spanning protein is a G-protein coupled receptor protein.

12. The method of claim 1, wherein said heterologous multiple membrane spanning protein is an ion-channel protein.

13. The method of claim 1, prior to administering the virus-like particle comprising the enveloped virus core and a heterologous multiple membrane spanning protein to the animal, preparing the isolated virus-like particle comprising an enveloped virus core and a heterologous multiple membrane spanning protein.

* * * * *